United States Patent
Yazaki et al.

[11] Patent Number: 5,910,498
[45] Date of Patent: Jun. 8, 1999

[54] PYRIDONECARBOXYLIC ACID DERIVATIVES OR SALTS THEREOF AND ANTIBACTERIAL AGENTS COMPRISING THE SAME AS ACTIVE INGREDIENT

[75] Inventors: Akira Yazaki; Jiro Yoshida; Yoshiko Niino; Yoshihiro Ohshita; Norihiro Hayashi; Hirotaka Amano; Yuzo Hirao; Yasuhiro Kuramoto, all of Hiroshima, Japan

[73] Assignee: Wakunaga Seiyaku Kabushiki Kaisha, Osaka, Japan

[21] Appl. No.: 08/817,603

[22] PCT Filed: Oct. 20, 1995

[86] PCT No.: PCT/JP95/02156

§ 371 Date: Jul. 8, 1997

§ 102(e) Date: Jul. 8, 1997

[87] PCT Pub. No.: WO96/12704

PCT Pub. Date: May 2, 1996

[30] Foreign Application Priority Data

Oct. 20, 1994 [JP] Japan .................... 6-255046
Jan. 30, 1995 [JP] Japan .................... 7-012673

[51] Int. Cl.⁶ .................. A61K 31/495; A61K 31/47; C07D 401/02; C07D 401/04
[52] U.S. Cl. ............... 514/255; 514/300; 514/312; 544/362; 544/363; 546/123; 546/156
[58] Field of Search ................. 546/123, 156; 544/362, 363; 514/255, 300, 312

[56] References Cited

U.S. PATENT DOCUMENTS 4,146,719  3/1979  Irikura ........................ 544/363

FOREIGN PATENT DOCUMENTS 53-141286  12/1978  Japan .
55-31042   3/1980   Japan .
57-46986   3/1982   Japan .
60-228479  11/1985  Japan .
62-135458  6/1987   Japan .

Primary Examiner—Bernard Dentz
Attorney, Agent, or Firm—Birch, Stewart, Kolasch & Birch, LLP

[57] ABSTRACT

The invention provides a pyridonecarboxylic acid derivative of the following general formula (1):

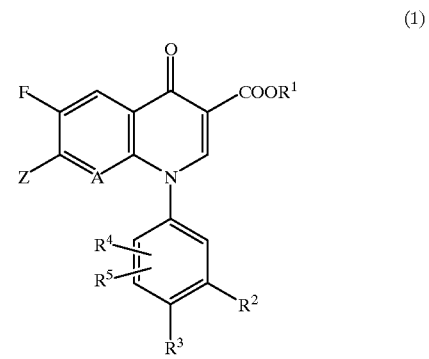

wherein $R^1$ is a hydrogen atom or carboxy protecting group, $R^2$ is a nitro or substituted or unsubstituted amino group, $R^3$ is a halogen atom, each of $R^4$ and $R^5$, which may be the same or different, is a hydrogen atom, halogen atom, lower alkyl group or lower alkoxy group, A is a nitrogen atom or —CX═ wherein X is a hydrogen atom, halogen atom, lower alkyl group or lower alkoxy group, and Z is a halogen atom or a saturated cyclic amino group which may have a substituent, or a salt thereof and an antibacterial agent comprising the same.

12 Claims, No Drawings ately easily
PYRIDONECARBOXYLIC ACID DERIVATIVES OR SALTS THEREOF AND ANTIBACTERIAL AGENTS COMPRISING THE SAME AS ACTIVE INGREDIENT This application is a 371 of PCT/JP95/02156 filed Oct. 20, 1995.

FIELD OF THE INVENTION

This invention relates to a novel pyridonecarboxylic acid derivative or salt thereof having improved antibacterial action and peroral absorption and an antibacterial agent comprising the same.

BACKGROUND ART

Among compounds having pyridonecarboxylic acid as a basic skeleton, many are known to be useful as synthetic antibacterial agents because they have superior antibacterial action and a broad antibacterial spectrum. Inter alia, norfloxacin (JP-A 141286/1978), enoxacin (JP-A 31042/1980), ofloxacin (JP-A 46986/1982), ciprofloxacin (JP-A 76667/1983), tosufloxacin (JP-A 228479/1985), etc. are widely used in clinical treatment as an infectious disease remedy.

These compounds, however, are still unsatisfactory in antibacterial activity, enteral absorption, metabolic stability and side effect, especially phototoxicity and cytotoxicity.

DISCLOSURE OF THE INVENTION

The present invention has been made under the above-mentioned circumferences and its object is to provide novel pyridonecarboxylic acid derivatives or salts thereof which are satisfactory in antibacterial action, enteral absorption, metabolic stability and side effects, especially phototoxicity and cytotoxicity, and an antibacterial agent comprising the same.

In view of the foregoing circumstances, the present inventors have carried out on extensive investigation with a view toward obtaining clinically improved synthetic antibacterial agents. As a result, it has been found that compounds represented by the formula (1) described below exhibit excellent antibacterial activities against gram negative and gram positive bacteria, are very low toxic, and are quite useful as synthetic antibacterial agents, leading to the completion of the invention.

More specifically, the present invention provides a pyridonecarboxylic acid derivative represented by the following general formula (1):

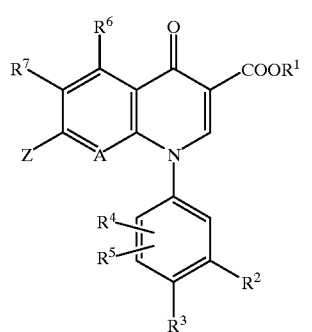

(1)

wherein $R^1$ is a hydrogen atom or carboxy protecting group, $R^2$ is a nitro or substituted or unsubstituted amino group, $R^3$ is a halogen atom, each of $R^4$ and $R^5$, which may be the same or different, is a hydrogen atom, halogen atom, lower alkyl group or lower alkoxy group, $R^6$ is a hydrogen atom, halogen atom, hydroxy group, lower alkyl group or amino group, $R^7$ is a hydrogen atom or halogen atom, A is a nitrogen atom or —CX= wherein X is a hydrogen atom, halogen atom, lower alkyl group or lower alkoxy group, and Z is a halogen atom or a saturated cyclic amino group which may have a substituent, or a salt thereof.

The present invention also provides an antibacterial agent comprising the pyridonecarboxylic acid derivative or salt thereof as an active ingredient.

BEST MODE FOR CARRYING OUT THE INVENTION

The present invention is described below in detail. In conjunction with the substituents in the pyridonecarboxylic acid derivative of general formula (1) according to the invention, the term "lower" means that the substituents have 1 to 7 carbon atoms, especially 1 to 5 carbon atoms when they have a chain structure and 3 to 7 carbon atoms when they are cyclic.

In general formula (1), the carboxy protecting group represented by $R^1$ is an ester residue of a carboxylic ester, for example, ester residues which are relatively easily cleaved to liberate a corresponding free carboxyl group. Exemplary groups are those groups which are eliminated by such treatment under moderate conditions as hydrolysis and catalytic reduction, for example, lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups having 7 to 11 carbon atoms such as benzyl group; and aryl groups having 6 to 14 carbon atoms such as phenyl group and naphthyl group, or those groups which are readily eliminated in a living body, for example, lower alkanoyloxy lower alkyl groups such as acetoxymethyl group and pivaloyloxymethyl group; lower alkoxycarbonyloxy lower alkyl groups such as methoxycarbonyloxymethyl group and 1-ethoxycarbonyloxyethyl group; lower alkoxy lower alkyl groups such as methoxymethyl group; lactonyl groups such as phthalidyl group; di-lower alkylamino lower alkyl groups such as 1-dimethylaminoethyl group; and (5-methyl-2-oxo-1,3-dioxol-4-yl)methyl group. It is especially preferred that $R^1$ is a hydrogen atom.

In the substituted amino group represented by $R^2$, the substituents include lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups having 7 to 11 carbon atoms such as benzyl group and 1-phenylethyl group; aryl groups having 6 to 14 carbon atoms such as phenyl group and naphthyl group; lower alkanoyl groups such as formyl group, acetyl group, propionyl group, butyryl group, and isobutyryl group; lower alkoxycarbonyl groups such as methoxycarbonyl group and ethoxycarbonyl group; aroyl groups having 7 to 15 carbon atoms such as benzoyl group and naphthoyl group; amino acid residues or oligopeptide residues such as glycyl, leucyl, valyl, alanyl, phenylalanyl, alanyl-alanyl, glycyl-valyl, and glycyl-glycyl-valyl, and amino acid residues or oligopeptide residues whose functional group is protected with a protective group conventionally used in peptide chemistry such as an acyl and lower aralkyl group, or cyclic amino groups. There may be contained one or two substituents which may be selected from the same or different types. It is expected that compounds protected with such an amino acid residue or peptide residue are improved in water solubility.

Preferably, $R^2$ is selected from an amino group, (lower alkyl)amino groups, di-(lower alkyl)amino groups, (lower alkanoyl)amino groups, amino acid-substituted amino groups, and oligopeptide-substituted amino groups. More preferably, $R^2$ is selected from an amino group, methylamino group, ethylamino group, dimethylamino group, formylamino group, glycyl-amino group, leucyl-amino group, valyl-amino group, alanyl-amino group, and alanyl-alanyl-amino group, with the amino group being most preferred.

Examples of the halogen atom represented by $R^3$, $R^4$, $R^5$, $R^6$, and $R^7$ include a fluorine atom, chlorine atom, bromine atom and iodine atom. Inter alia, fluorine or chlorine atom is preferred, with the fluorine atom being most preferred.

Examples of the lower alkyl group represented by $R^4$, $R^5$, $R^6$, and X include a methyl group, ethyl group, n-propyl group, i-propyl group, n-butyl group, i-butyl group, t-butyl group, pentyl group, hexyl group, and heptyl group, with the methyl group being most preferred. Examples of the lower alkoxy group represented by $R^4$, $R^5$, and X include a methoxy group, ethoxy group, n-propoxy group, n-butoxy group, and t-butoxy group.

A preferred combination of $R^4$ and $R^5$ is a combination of a halogen atom and a hydrogen atom. More preferably, $R^4$ is a fluorine atom or chlorine atom and $R^5$ is a hydrogen atom. Most preferably $R^4$ is a fluorine atom and $R^5$ is a hydrogen atom. It is especially preferred that $R^4$ is substituted at the para-position relative to $R^2$.

Examples of the halogen atom represented by X and Z include a fluorine atom, chlorine atom, bromine atom and iodine atom, with the fluorine atom and chlorine atom being especially preferred.

The compound of formula (1) has a naphthyridine skeleton when A represents a nitrogen atom and a quinoline skeleton when A represents —CX═. Compounds of formula (1) wherein A is a nitrogen atom and —CCl═ are especially preferred.

Where Z is a saturated cyclic amino group which may have a substituent, the cyclic amino group may contain in its ring one or more hetero atoms such as nitrogen atoms, oxygen atoms and sulfur atoms and carbonyl carbon and may be mono-, di- or tri-cyclic. Preferred monocyclic rings are 4 to 7-membered rings, preferred dicyclic rings are 7 to 11-membered rings, and preferred tricyclic rings are 9 to 15-membered rings. Examples of the cyclic amino group include saturated monocyclic 3 to 7-membered cyclic amino groups having one nitrogen atom such as aziridin-1-yl, azetidin-1-yl, pyrrolidin-1-yl, and piperidin-1-yl; saturated monocyclic 3 to 7-membered cyclic amino groups having two nitrogen atoms such as piperazin-1-yl and homopiperazin-1-yl; saturated monocyclic 3 to 7-membered cyclic amino groups having a hetero atom selected from oxygen and sulfur atoms in addition to a nitrogen atom such as oxazolidin-3-yl, morpholin-4-yl, thiazolidin-1-yl, and thiomorpholin-4-yl; saturated di- and tricyclic amino groups such as tetra-hydroquinolin-1-yl; and spiro and crosslinked, saturated 5 to 12-membered cyclic amino groups such as 2,8-diazaspiro[4.4]nonan-2-yl, 5-azaspiro[2.4]heptan-5-yl, 7-azabicyclo[2.2.1]heptan-7-yl, 2,8-diazabicyclo[4.3.0]nonan-8-yl, 5-methyl-2,5-diazabicyclo[2.2.1]heptan-2-yl, 2,5-diazabicyclo[2.2.1]heptan-2-yl, and 3,8-diazabicyclo[3.2.1]-octan-3-yl.

The atoms forming the ring of these saturated cyclic amino groups may have appropriate substituents. Examples of the substituent group include a hydroxyl group, lower alkyl groups, substituted or unsubstituted amino groups, substituted or unsubstituted amino lower alkyl groups, lower alkoxy groups, and halogen atoms.

Examples of the lower alkyl group which can be a substituent on the saturated cyclic amino group include those having 1 to 7 carbon atoms such as a methyl group, ethyl group, propyl group, butyl group, pentyl group, hexyl group, and heptyl group; examples of the lower alkoxy group include those having 1 to 7 carbon atoms such as a methoxy group, ethoxy group, and n-propoxy group; examples of the halogen atoms include a fluorine atom, chlorine atom, and bromine atom. Among the substituents on the saturated cyclic amino group, the substituted amino groups and substituted amino lower alkyl groups have substituents which are as described for $R^2$. Especially preferred examples of these substituted amino groups and substituted or unsubstituted amino lower alkyl groups include a methylamino group, ethylamino group, dimethylamino group, aminomethyl group, 1-aminoethyl group, 2-aminoethyl group, 1-amino-1-ethyl group, methylaminomethyl group, ethylaminomethyl group, dimethylaminomethyl group, glycyl-amino group, leucyl-amino group, valyl-amino group, alanyl-amino group, and alanyl-alanyl-amino group.

Preferred among these saturated cyclic amino groups are groups of the following formulae (a) and (b).

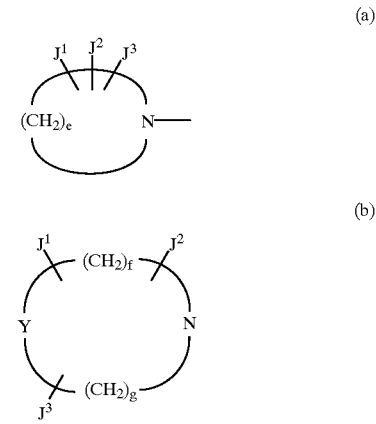

In the formulae, Y is an oxygen atom, sulfur atom or $NR^8$ wherein $R^8$ is a hydrogen atom or lower alkyl group, letter e is a number of 3 to 5, f is a number of 1 to 3, g is a number of 0 to 2, each of $J^1$, $J^2$ and $J^3$, which may be the same or different, is a hydrogen atom, hydroxyl group, lower alkyl group, amino lower alkyl group, amino group, lower alkyl amino group, lower alkoxy group or halogen atom.

Examples of the lower alkyl group, amino lower alkyl group, lower alkyl amino group, lower alkoxy group and halogen atom in formulae (a) and (b) are as described above for $R^2$ to $R^5$.

The cyclic amino groups of formula (a) are, for example, azetidin-1-yl, pyrrolidin-1-yl, and piperidin-1-yl groups and the cyclic amino groups of formula (b) are, for example, piperazin-1-yl group, morpholin-4-yl group, thiomorpholin-4-yl group, homopiperadin-1-yl group, N-thiazolidinyl group, and N-oxazolidinyl group. Among these, the cyclic amino groups of formula (a) are preferred, with the azetidin-1-yl and pyrrolidin-1-yl groups being especially preferred.

Especially preferred examples of the groups of formulae (a) and (b) are given below.

Included are 3-aminoazetidin-1-yl group, 3-methylaminoazetidin-1-yl group, 3-dimethylaminoazetidin-1-yl group, 3-aminomethylazetidin-1-yl group, 3-amino-2-methylazetidin-1-yl group, 3-amino-3-methylazetidin-1-yl group, 3-alanyl-aminoazetidin-1-yl group, 3-valyl-aminoazetidin-1-yl group, pyrrolidin-1-yl group, 3-hydroxypyrrolidin-1-yl group, 3,4-dihydroxypyrrolidin-1-yl group, 3-methoxypyrrolidin-1-yl group, 3-methylpyrrolidin-1-yl group, 3-hydroxy-4-methylpyrrolidin-1-yl group, 3-aminopyrrolidin-1-yl group, 3-methylaminopyrrolidin-1-yl group, 3-dimethylaminopyrrolidin-1-yl group, 3-ethylaminopyrrolidin-1-yl group, 3-diethylaminopyrrolidin-1-yl group, 3-aminomethylpyrrolidin-1-yl group, 3-amino-3-methylpyrrolidin-1-yl group, 3-amino-4-methylpyrrolidin-1-yl group, 3-amino-5-methylpyrrolidin-1-yl group, 3-methylamino-4-methylpyrrolidin-1-yl group, 3-dimethylamino-4-methylpyrrolidin-1-yl group, 3-ethylamino-4-methylpyrrolidin-1-yl group, 3-diethylamino-3-methylpyrrolidin-1-yl group, 3-diethylamino-4-methylpyrrolidin-1-yl group, 3-aminomethyl-4-methylpyrrolidin-1-yl group, 3-methylaminomethyl-4-methylpyrrolidin-1-yl group, 3-dimethylaminomethyl-4-methylpyrrolidin-1-yl group, 3-ethylaminomethyl-4-methylpyrrolidin-1-yl group, 3-(1-aminoethyl)-4-methylpyrrolidin-1-yl group, 3-(2-aminoethyl)-4-methylpyrrolidin-1-yl group, 3-amino-4-ethylpyrrolidin-1-yl group, 3-methylamino-4-ethylpyrrolidin-1-yl group, 3-dimethylamino-4-ethylpyrrolidin-1-yl group, 3-ethylamino-4-ethylpyrrolidin-1-yl group, 3-diethylamino-4-ethylpyrrolidin-1-yl group, 3-aminomethyl-4-ethylpyrrolidin-1-yl group, 3-methylaminomethyl-4-ethylpyrrolidin-1-yl group, 3-dimethylaminomethyl-4-ethylpyrrolidin-1-yl group, 3-amino-3-methylpyrrolidin-1-yl group, 3-methylamino-3-methylpyrrolidin-1-yl group, 3-dimethylamino-3-methylpyrrolidin-1-yl group, 3-amino-3,4-dimethylpyrrolidin-1-yl group, 3-amino-4,4-dimethylpyrrolidin-1-yl group, 3-amino-4,5-dimethylpyrrolidin-1-yl group, 3-amino-2,4-dimethylpyrrolidin-1-yl group, 3-methylamino-3,4-dimethylpyrrolidin-1-yl group, 2-methyl-3-aminopyrrolidin-1-yl group, 2-methyl-3-dimethylaminopyrrolidin-1-yl group, 3-amino-4-methoxypyrrolidin-1-yl group, 3-alanyl-aminopyrrolidin-1-yl group, 3-valyl-aminopyrrolidin-1-yl group, piperadin-1-yl group, 4-methylpiperadin-1-yl group, 3-methylpiperadin-1-yl group, 2-methylpiperadin-1-yl group, 3,4-dimethylpiperadin-1-yl group, 3,5-dimethylpiperadin-1-yl group, 3,3-dimethylpiperadin-1-yl group, 3,4,5-trimethylpiperadin-1-yl group, piperidin-1-yl group, 4-aminopiperidin-1-yl group, 4-dimethylaminopiperidin-1-yl group, 4-hydroxypiperidin-1-yl group, morpholin-4-yl group, 2-aminomethylmorpholin-4-yl group, 2-methylaminomorpholin-4-yl group, 2-dimethylaminomorpholin-4-yl group, thiomorpholin-4-yl group, homopiperadin-1-yl group, 4-methylhomopiperadin-1-yl group, N-thiazolidinyl group, and N-oxazolidinyl group.

More preferred combinations of $R^1$, $R^2$, $R^3$, $R^4$, $R^5$, $R^6$, $R^7$, A and Z in general formula (1) are such that $R^1$ is a hydrogen atom; $R^2$ is an amino group, (lower alkyl)amino, di-(lower alkyl)amino group, (lower alkanoyl)amino group, amino acid-substituted amino group or oligopeptide-substituted amino group; $R^3$ is a halogen atom; $R^4$ is a halogen atom; $R^5$ is a hydrogen atom; $R^6$ is a hydrogen atom; $R^7$ is a fluorine atom; A is a nitrogen atom, —CH= or —CCl=; and Z is a group of formula (a). Further preferably, $R^1$, $R^2$, $R^3$, $R^4$, $R^5$, $R^6$, $R^7$, A and Z are combined such that $R^1$ is a hydrogen atom; $R^2$ is an amino group; $R^3$ is a fluorine atom or chlorine atom; $R^4$ is a fluorine atom or chlorine atom (substituted at the para-position relative to $R^2$); $R^5$ is a hydrogen atom; $R^6$ is a hydrogen atom; $R^7$ is a fluorine atom; A is a nitrogen atom or —CCl=; and Z is a group of formula (a) wherein e=3 or 4.

The pyridonecarboxylic acid derivative or salt thereof (1) may form either an acid addition salt or a base addition salt. Included in the salts are chelate salts with boron compounds. Examples of the acid addition salt include (A) salts with mineral acids such as hydrochloric acid and sulfuric acid; (B) salts with organic carboxylic acids such as formic acid, citric acid, trichloroacetic acid, trifluoroacetic acid, fumaric acid, and maleic acid, and (C) salts with sulfonic acids such as methanesulfonic acid, benzenesulfonic acid, p-toluenesulfonic acid, mesitylenesulfonic acid, and naphthalenesulfonic acid. Examples of the base addition salt include (A') salts with alkali metals such as sodium and potassium, (B') salts with alkaline earth metals such as calcium and magnesium, (C') ammonium salts, and (D') salts with nitrogenous organic bases such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine, and N,N'-dibenzylethylenediamine. Exemplary boron compounds include boron halides such as boron fluoride and lower acyloxyboron compounds such as acetoxyboron.

The pyridonecarboxylic acid derivatives or salts thereof (1) can be present not only as non-solvates, but also as hydrates or solvates. Therefore, the compounds of the invention include all crystal forms and hydrates or solvates thereof.

The pyridonecarboxylic acid derivatives or salts thereof (1) can be present as optical active compounds. These optical active compounds are also involved in the compounds of the invention. Moreover, the compounds (1) can be present as different stereoisomers of cis and trans forms. These stereoisomers are also involved in the compounds of the invention.

The pyridonecarboxylic acid derivatives or salts thereof (1) are prepared by any desired method which complies with a particular type of substituent. One exemplary method is described below.

Procedure 1

Those compounds of general formula (1) wherein $R^1$ is a hydrogen atom or lower alkyl group and Z is a halogen atom are prepared, for example, by procedure 1 represented by the following reaction scheme.

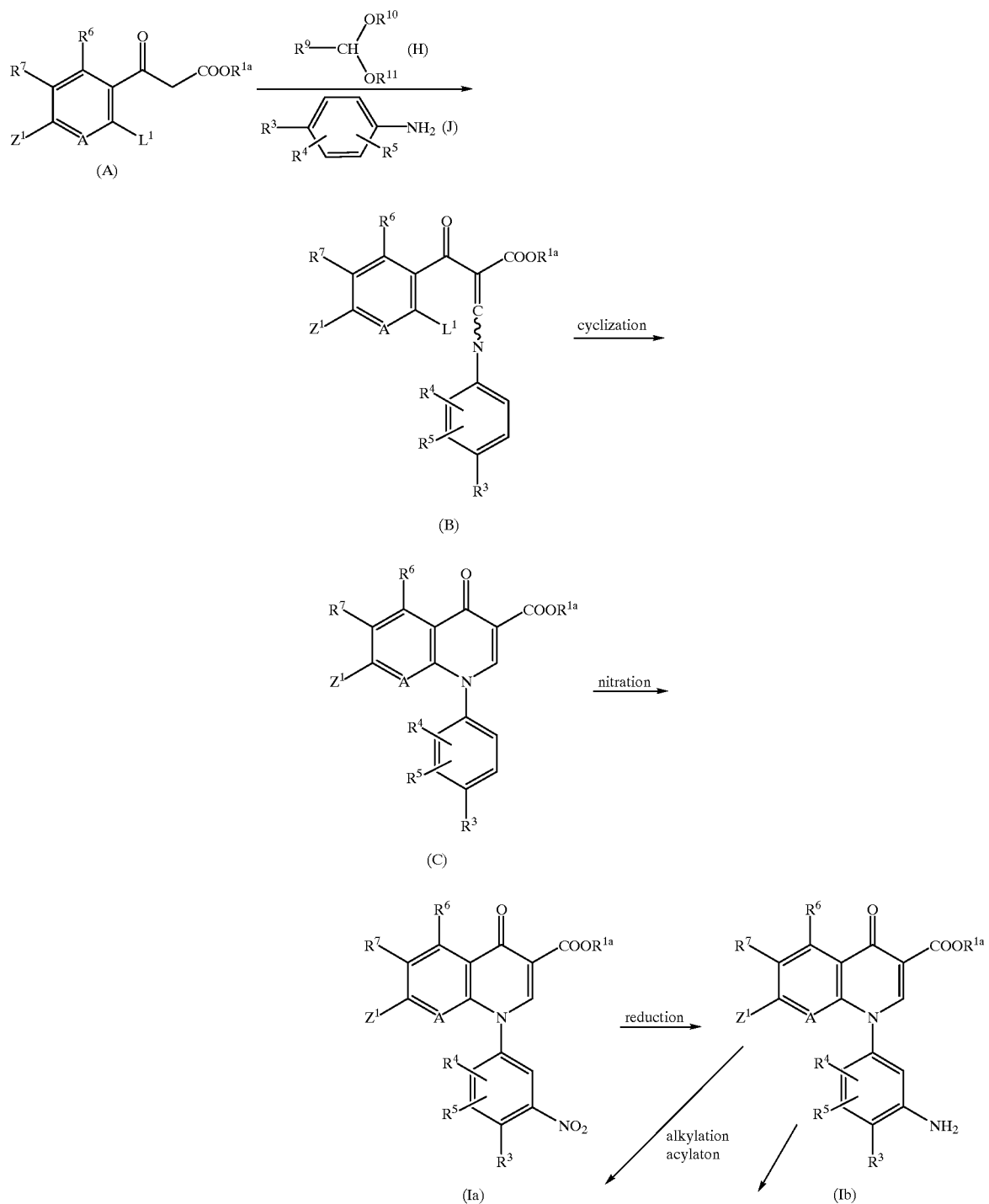

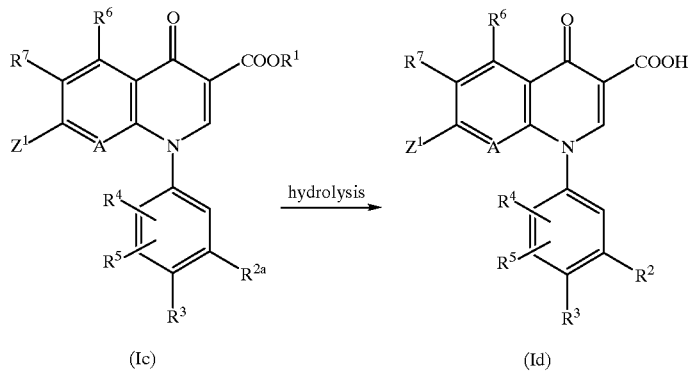

In the formulae, $R^{1a}$ is a lower alkyl group, $R^9$ is a lower alkoxy group or a group —$NR^{12}R^{13}$ wherein each of $R^{12}$ and $R^{13}$ is a lower alkyl group, each of $R^{10}$ and $R^{11}$ is a lower alkyl group, $L^1$ is a halogen atom, $Z^1$ is a halogen atom, $R^{2a}$ is a substituted amino group, $R^2$, $R^3$, $R^4$, $R^5$, $R^6$, $R^7$, and A are as defined above.

More particularly, inventive compound (1a)–(1d) is obtained by reacting a compound (A) with an ortho-formic ester (H) such as ethyl ortho-formate or methyl ortho-formate and then with a compound (J), then effecting cyclization reaction, and nitrating the resulting compound (C); inventive compound (1b) is obtained by reducing the compound (1a); inventive compound (1c) is obtained by alkylating or acylating the compound (1b); and inventive compound (1d) is obtained by hydrolyzing the compound (1c). The compound (1d) is also obtainable by hydrolyzing the compound (1b).

Reaction between compound (A) and ortho-formic ester (H) is generally carried out at 0 to 160° C., preferably 50 to 150° C. while the reaction time is generally 10 minutes to 48 hours, preferably 1 to 10 hours. The molar amount of ortho-formic ester (H) used is at least equal to, especially 1 to 10 times the molar amount of compound (A).

Reaction with compound (J) is carried out without a solvent or in a suitable solvent. Carboxylic anhydrides such as acetic anhydride are desirably added as reaction aids. Any desired solvent may be used herein insofar as it does not affect the reaction. Exemplary solvents include aromatic hydrocarbons such as benzene, toluene, and xylene; ethers such as diethyl ether, tetrahydrofuran, dioxane, monoglyme, and diglyme; aliphatic hydrocarbons such as pentane, hexane, heptane, and ligroin; halogenated hydrocarbons such as methylene chloride, chloroform, and carbon tetrachloride; aprotic polar solvents such as dimethylformamide and dimethylsulfoxide; and alcohols such as methanol, ethanol, and propanol. This reaction is generally carried out at 0 to 150° C., preferably 0 to 100° C. while the reaction time is generally 10 minutes to 48 hours. The molar amount of compound (J) used is at least equal to, especially 1 to 2 times the molar amount of compound (A).

Alternatively, compound (B) can be derived by reacting compound (A) with an acetal such as N,N-dimethylformamide dimethylacetal and N-dimethylformamide diethylacetal and then with compound (J). Any desired solvent may be used in the reaction with an acetal insofar as it does not affect the reaction, and exemplary solvents are as described above. The reaction is generally carried out at 0 to 150° C., preferably room temperature to 100° C. while the reaction time is generally 10 minutes to 48 hours, preferably 1 to 10 hours.

Compound (B) is subject to cyclization to yield compound (C). This reaction is carried out in the presence or absence of a basic compound in a suitable solvent. Any desired solvent may be used herein insofar as it does not affect the reaction. Exemplary solvents include aromatic hydrocarbons such as benzene, toluene, and xylene; ethers such as diethyl ether, tetrahydrofuran, dioxane, and monoglyme; halogenated hydrocarbons such as methylene chloride, chloroform, and carbon tetrachloride; alcohols such as methanol, ethanol, propanol, and butanol; and aprotic polar solvents such as dimethylformamide and dimethylsulfoxide. The basic compounds used herein include alkali metals such as metallic sodium and metallic potassium; metal hydrides such as sodium hydride and calcium hydride; inorganic salts such as sodium hydroxide, potassium hydroxide, sodium carbonate and potassium carbonate; alkoxides such as sodium methoxide, sodium ethoxide, and potassium t-butoxide; metal fluorides such as sodium fluoride and potassium fluoride; and organic bases such as triethylamine and 1,8-diazabicyclo[5.4.0]undecene (DBU). This reaction generally uses a reaction temperature of 0 to 200° C., preferably room temperature to 180° C. and generally completes in 5 minutes to 24 hours. The molar amount of the basic compound used may be at least equal to, preferably 1 to 2 times the molar amount of compound (B).

Compound (C) is subject to nitration to produce inventive compound (1a). For nitration, conventional methods used in the nitration of aromatic compounds are applicable. The nitrating agents include a mixed acid of nitric acid or a nitrate combined with sulfuric acid, and acetyl nitrate. The amount of mixed acid used in the reaction is 1 equivalent to greater excess of sulfuric acid and 1 equivalent to greater excess of nitric acid per equivalent of compound (C). The reaction is carried out, for example, by adding compound (C) to mixed acid. Preferably the reaction temperature is −10° C. to 80° C. and the reaction time is 5 minutes to 5 hours.

Compound (1b) can be obtained by reducing compound (1a).

For the reduction, conventional methods are applicable, for example, a dissolved metal reduction method using zinc, iron, tin, tin (II) chloride or the like in acidic solution, a reduction method using sulfides such as sodium sulfide, sodium hydrosulfide, and sodium dithionite, and a catalytic reduction method using platinum, Raney nickel, platinum black (Pt—C), palladium-carbon (Pd—C) or the like.

Compound (1d) wherein $R^1$ is a hydrogen atom can be obtained by hydrolyzing compound (1b) or if desired, by alkylating or acylating compound (1b) followed by hydrolysis.

For the hydrolysis, any reaction conditions used in conventional hydrolysis reaction are applicable. For example, hydrolysis is carried out in the presence of a basic compound such as sodium hydroxide, potassium hydroxide, sodium carbonate and potassium carbonate; a mineral acid such as hydrochloric acid, sulfuric acid, and hydrobromic acid; or an organic acid such as p-toluene-sulfonic acid, in a solvent including water, an alcohol such as methanol, ethanol, and propanol, an ether such as tetrahydrofuran and dioxane, a ketone such as acetone and methyl ethyl ketone, and acetic acid or a mixture of such solvents. This reaction is generally carried out at room temperature to 180° C., preferably room temperature to 140° C. while the reaction time is generally 1 to 24 hours.

The alkylation reaction to produce inventive compound (1c) may be carried out by reacting compound (1b) with an alkylating agent such as a dialkyl sulfate, alkyl iodide and alkyl bromide corresponding to a desired alkyl group, preferably in the presence of a base such as sodium carbonate and potassium carbonate in a solvent such as N,N-dimethylformamide and N-methylpyrrolidone at a temperature of room temperature to about 150° C. The alkylation reaction can also be carried out in the co-presence of a carbonyl compound corresponding to a desired alkyl group by a catalytic reduction method using platinum, Raney nickel, platinum black, and palladium-carbon. The acylation reaction can be carried out by any conventional methods used in acylating an amino group, for example, by reacting compound (1b) with an acyl chloride corresponding to a desired acyl group or acid anhydride in a solvent, for example, halogenated hydrocarbons such as methylene chloride, chloroform, carbon tetrachloride, and chlorobenzene; aromatic hydrocarbons such as benzene and toluene; ethers such as tetrahydrofuran and dioxane; aprotic polar solvents such as acetonitrile and N,N-dimethylformamide at 0° C. to room temperature or in the presence or absence of a base such as pyridine, picoline, N,N-dimethylaniline, N-methylmorpholine, dimethylamine, triethylamine, sodium carbonate, and potassium carbonate at −70 to 100° C., or by reacting with an acid such as formic acid and acetic acid or acid anhydride at room temperature to 150° C.

It is noted that a compound of general formula (1) wherein $R^6$ is an amino group is preferably obtained by starting with a compound (A) wherein $R^6$ is a halogen atom, carrying out the above-mentioned reactions to convert it into compound (1a), (1b), (1c) or (1d), and thereafter aminating the halogen atom.

Compound (1b) can also be synthesized by the following method.

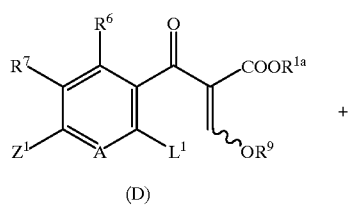

(D)

+

-continued

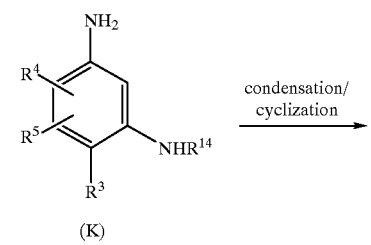

(K)

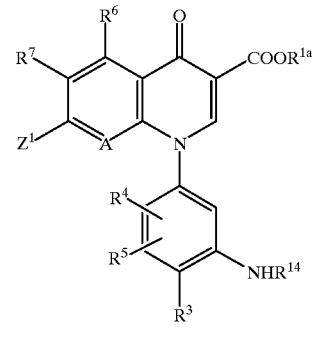

(L)

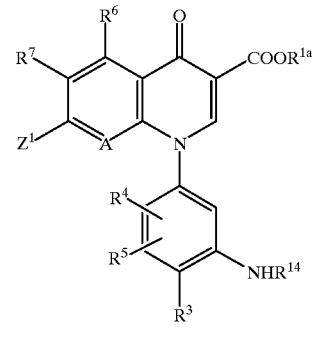

(Ib)

In the formulae, $R^{14}$ is an amino protecting group, $R^{1a}$, $R^3$, $R^4$, $R^5$, $R^6$, $R^7$, $R^9$, $L^1$, $Z^1$, and A are as defined above.

More particularly, compound (1b) can be obtained by reacting the above-mentioned compound (A) with an orthoformate (H) to form an acrylate (D), condensing and cyclizing the acrylate (D) with a phenylenediamine (K) to form a compound (L), and thereafter removing or deprotecting the amino protecting group.

The reactions for deriving compound (L) from compound (A) may be carried out under the same conditions as the above-mentioned reactions for deriving compound (C) from compound (A).

Deprotection of the amino protecting group (mainly an acyl group and carbamoyl group) is carried out by hydrolysis with an acid or alkali. The conditions are the same as the above-mentioned hydrolysis to compound (1b) or (1c).

Procedure 2

Those compounds of general formula (1) wherein Z is a saturated cyclic amino group which may have a substituent are prepared, for example, by procedure 2 represented by the following reaction scheme.

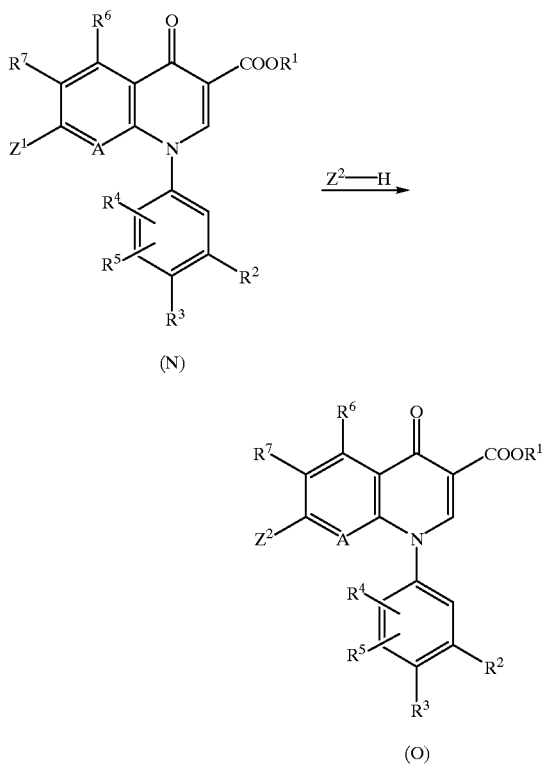

(N)

(O)

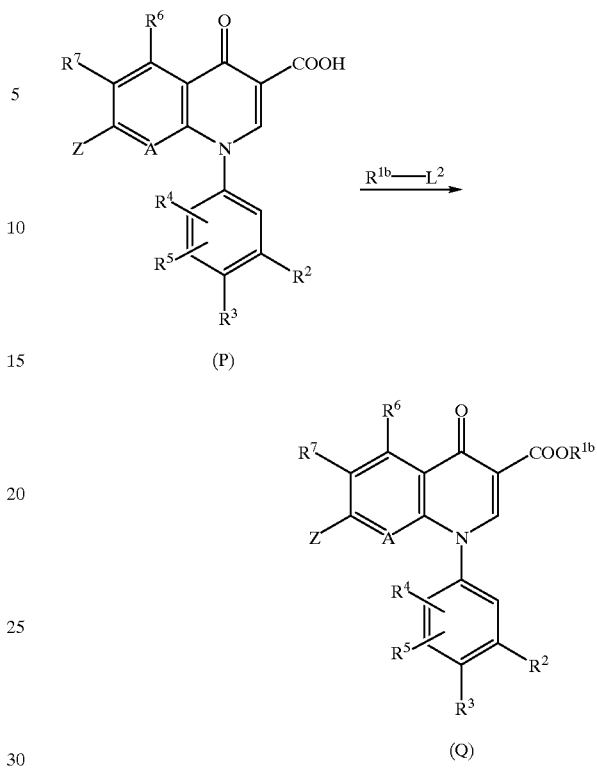

(P)

(Q)

In the formulae, $Z^2$ is a saturated cyclic amino group which may have a substituent, $R^1, R^2, R^3, R^4, R^5, R^6, R^7, Z^1$, and A are as defined above.

More particularly, compound (O) is obtained by aminating compound (N) with a compound represented by the formula: $Z^2$—H.

This reaction is carried out in a solvent which does not affect the reaction, for example, aromatic hydrocarbons such as benzene, toluene, and xylene; alcohols such as methanol and ethanol; ethers such as tetrahydrofuran, dioxane, and monoglyme; halogenated hydrocarbons such as methylene chloride, chloroform, and carbon tetrachloride; aprotic polar solvents such as dimethylformamide, dimethylsulfoxide, and N-methylpyrrolidone; acetonitrile and pyridine, optionally in the presence of a neutralizing agent such as sodium carbonate, calcium carbonate, sodium hydrogen carbonate, triethylamine, and 1,8-diazabicyclo[5.4.0]-undecene (DBU), at room temperature to 160° C. The reaction time is several minutes to 48 hours, preferably 10 minutes to 24 hours. The molar amount of compound $Z^2$—H used is at least equal to, especially 1 to 5 times the molar amount of compound (N). It is noted that where $R^1$ is a carboxy protecting group, it can be converted into a hydrogen atom by hydrolysis if desired.

Procedure 3

Those compounds of general formula (1) wherein $R^1$ is a carboxy protecting group are prepared, for example, by procedure 3 represented by the following reaction scheme.

In the formulae, $R^{1b}$ is a carboxy protecting group, $L^2$ is a halogen atom, $R^2$, $R^3$, $R^4$, $R^5$, $R^6$, $R^7$, A, and Z are as defined above.

More particularly, compound (Q) is obtained by reacting compound (P) with a halide $R^{1b}$—$L^2$. Examples of the solvent which can be used herein include aromatic hydrocarbons such as benzene and toluene; halogenated hydrocarbons such as methylene chloride and chloroform; aprotic polar solvents such as dimethylformamide and dimethylsulfoxide; and inert solvents such as acetonitrile. The reaction temperature is generally room temperature to about 100° C. This reaction is preferably carried out in the presence of a basic compound such as triethylamine, diisopropylethylamine, dicyclohexylamine, DBU, sodium carbonate, potassium carbonate, and sodium hydroxide.

Where the reactant compounds used in the aforementioned Procedures 1 to 3 contain a group which does not participate in the relevant reaction, such as amino, imino, hydroxy, mercapto or carboxyl group, it is acceptable to carry out reaction with that group protected and remove the protective group by a conventional technique after the completion of reaction. The protective group may be any of groups which can be removed without disrupting the structure of an inventive compound resulting from the reaction, and groups commonly used in the chemical fields of peptides, amino sugar, and nucleic acids are useful.

The starting compound (A) can be prepared by the methods described in the following literature or similar methods.

1) J. Heterocyclic Chem., 22, 1033 (1985)
2) Liebigs Ann. Chem., 29 (1987)
3) J. Med. Chem., 31, 991 (1988)
4) J. Org. Chem., 35, 930 (1970)
5) JP-A 246541/1987

6) JP-A 26272/1987

7) JP-A 145268/1988

8) J. Med. Chem., 29, 2363 (1986)

9) J. Fluorin Chem., 28, 361 (1985)

10) JP-A 198664/1988

11) JP-A 264461/1988

12) JP-A 104974/1988

13) EP-A 230948

14) JP-A 2823984/1990

15) Publication of the Japanese translation of International Patent Application No. 502452/1991

16) J. Het. Chem., 27, 1609 (1990)

The inventive compounds thus obtained are isolated and purified in a conventional manner. Depending on the isolating and purifying conditions, the compounds are obtained in the form of a salt, free carboxylic acid or free amine. Since these forms are interchangeable as desired, the inventive compound can be produced in the intended form.

The inventive compounds (1) or salts thereof can be formulated as an antibacterial agent with pharmaceutically acceptable carriers to form compositions suitable for parenteral administration such as injection, rectal administration and instillation, and oral administration in solid or liquid form.

The antibacterial agent composition of the invention for parenteral injections may take the form of an aqueous or nonaqueous solution, suspension or emulsion in pharmaceutically acceptable sterile water or nonaqueous solvent. Examples of the suitable nonaqueous carrier, diluent, solvent or vehicle include propylene glycol, polyethylene glycol, vegetable oils such as olive oil, and injectable organic esters such as ethyl oleate. Such compositions may further contain adjuvants such as antiseptic agents, humectants, emulsifiers and dispersants. The composition may be sterilized by passing through a bacteria-collecting filter, or by introducing a sterilizer as such or in the form of a sterile solid composition soluble in a certain amount of another sterile injectable medium.

In preparations for instillation, a solubilizer, preservative, isotonic agent, thickener or the like may be added to the inventive compound.

Solid preparations for oral administration include capsules, tablets, pills, powders, and granules. The solid preparation is generally formulated by mixing the inventive compound with at least one inert diluent such as sucrose, lactose and starch. In preparing such a preparation, an additional agent other than the inert diluent such as a lubricant (e.g., magnesium stearate) may also be used. In the case of capsules, tablets and pills, a buffer agent may be used. Tablets and pills may be covered with enteric coatings.

For liquid preparations for oral administration, there may be used inert diluents which are commonly used by those skilled in the art, for example, pharmaceutically acceptable water-containing emulsions, solutions, suspensions, syrups and elixirs. In the composition, adjuvants, for example, humectants, emulsifiers, suspending agents, sweeteners, seasoning agents and flavoring agents may also be blended in addition to the inert diluents. Preparations for rectal administration may preferably contain an excipient such as cacao butter or suppository wax in addition to the inventive compound.

The dose of the inventive compound (1) varies with the form of a compound to be administered, administration route, desired treating period and other factors although the daily dose is preferably about 0.1 to 1,000 mg/kg, especially about 0.5 to 100 mg/kg of adult. If desired, the daily dose may be administered in two to four portions.

Since the inventive compounds (1) and salts thereof have very high antibacterial activity, low phototoxicity and cytotoxicity, they can be widely used not only as human and animal medicines, but also as medicines for fish disease medicines, pesticides, food preservatives and the like. Moreover, the inventive compounds are expected to have antiviral activity, especially anti-human immunodeficiency virus (HIV) activity and thus believed effective for the prevention and treatment of aids.

Examples of the invention are given below together with reference examples by way of illustration and not by way of limitation.

REFERENCE EXAMPLE 1

Ethyl 7-chloro-6-fluoro-1,4-dihydro-4-oxo-1-(2,4,6-trifluorophenyl)-1,8-naphthyridine-3-carboxylate With ice cooling, 5 ml of a toluene solution containing 1.39 ml of 2,4,6-trifluoroaniline was added dropwise to 10 ml of a toluene solution containing 6.40 g of ethyl 2-(2,6-dichloro-5-fluoronicotinoyl)-3-ethoxyacrylate and stirred overnight at room temperature. The solvent was distilled off then to the residue, ethanol was added. The resulting crystals were collected by filtration and washed with diethyl ether, to give ethyl 2,6-dichloro-5-fluoronicotinoyl-3-(2,4,6-trifluorophenyl)aminoacrylate. To 9 ml of a N,N-dimethylformamide solution containing 2.0 g of ethyl 2,6-dichloro-5-fluoronicotinoyl-3-(2,4,6-trifluorophenylamino)acrylate was added 0.63 g of potassium carbonate. The solution was stirred for 90 minutes at room temperature. The reaction solution was poured into ice water, the precipitated solid was collected by filtration and washed with ethanol and diethyl ether, to give 1.38 g of the title compound.

Properties: colorless powder mp: 158–160° C.

$^1$H-NMR (CDCl$_3$) δ: 1.41 (t, J=7 Hz, 3H), 4.42 (q, J=7 Hz, 2H), 6.92–7.06 (m, 2H), 8.48 (d, J=11 Hz, 1H), 8.49 (S, 1H)

REFERENCE EXAMPLE 2

Ethyl 7-chloro-1-(2-chloro-4-fluorophenyl)-6-fluoro-1,4-dihydro-4-oxo-1,8-naphthyridine-3-carboxylate The title compound was obtained by the similar procedure as Reference Example 1 except that 2-chloro-4-fluoroaniline was used.

Properties: colorless powder mp: 177–178° C.

$^1$H-NMR (CDCl$_3$) δ: 1.41 (t, J=7 Hz, 3H), 4.41 (q, J=7 Hz, 2H), 7.23 (dd, J=3 Hz, 8 Hz, 1H), 7.36–7.51 (m, 2H), 8.49 (d, J=7 Hz, 1H), 8.49 (s, 1H)

REFERENCE EXAMPLE 3

Ethyl 1-(2-chloro-4-fluorophenyl)-6,7-difluoro-1,4-dihydro-4-oxoquinoline-3-carboxylate With ice cooling, 5 ml of a chloroform solution containing 1.2 ml of 2-chloro-4-fluoroaniline was added dropwise to 13 ml of a chloroform solution containing 2.46 g of ethyl 2-(2,4,5-trifluorobenzoyl)-3-ethoxyacrylate and stirred overnight at room temperature. The solvent was distilled off then to the residue, ethanol was added. The resulting crystals were collected by filtration and washed with diethyl ether, to give ethyl 2-(2,4,5-trifluorobenzoyl)-3-(2-chloro-4-fluorophenylamino)acrylate. To 15 ml of a N,N-dimethylformamide solution containing 3.00 g of ethyl 2-(2,4,5-trifluorobenzoyl)-3-(2-chloro-4-fluorophenylamino)acrylate was added 1.03 g of potassium carbonate. The solution was stirred for 90 minutes at room temperature. The reaction solution was poured into ice water, the precipitated solid was collected by filtration and washed with ethanol and diethyl ether, to give 2.74 g of the title compound.

Properties: colorless plates
mp: 220° C. (decomposed)
$^1$H-NMR (CDCl$_3$) δ: 1.40 (t, J=7 Hz, 3H), 4.39 (q, J=7 Hz, 2H), 6.54 (dd, J=6 Hz, 11 Hz, 1H), 7.46 (dd, J=3 Hz, 7 Hz, 1H), 7.56 (dd, J=5 Hz, 9 Hz, 1H), 7.50–7.64 (m, 2H), 8.25–8.38 (m, 1H), 8.34 (s, 1H)

REFERENCE EXAMPLE 4

Ethyl 7-chloro-1-(4-chloro-2-fluorophenyl)-6-fluoro-1,4-dihydro-4-oxo-1,8-naphthyridine-3-carboxylate The title compound was obtained by the similar procedure as Reference Example 1 except that 4-chloro-2-fluoroaniline was used.

Properties: colorless powder
mp: 216–218° C.
$^1$H-NMR (CDCl$_3$) δ: 1.41 (t, J=7 Hz, 3H), 4.40 (q, J=7 Hz, 2H), 7.34–7.45 (m, 3H), 8.47 (d, J=9 Hz, 1H), 8.55 (s, 1H)

REFERENCE EXAMPLE 5

Ethyl 7-chloro-6-fluoro-1-(4-fluoro-2-methylphenyl)-1,4-dihydro-4-oxo-1,8-naphthyridine-3-carboxylate The title compound was obtained by the similar procedure as Reference Example 1 except that 4-fluoro-2-methylaniline was used.

Properties: colorless powder
mp: 199–200° C.
$^1$H-NMR (CDCl$_3$) δ: 1.40 (t, J=7 Hz, 3H), 2.06 (s, 3H), 4.41 (q, J=7 Hz, 2H), 7.05–7.17 (m, 2H), 7.23 (d, J=5 Hz, 1H), 8.48 (d, J=7 Hz, 1H), 8.51 (s, 1H)

EXAMPLE 1

Ethyl 7-chloro-1-(2,4-difluoro-5-nitrophenyl)-6-fluoro-1,4-dihydro-4-oxo-1,8-naphthyridine-3-carboxylate To 8 ml of conc. sulfuric acid was added 2.00 grams of ethyl 7-chloro-1-(2,4-difluorophenyl)-6-fluoro-4-oxo-1,4-dihydro-1,8-naphthyridine-3-carboxylate. With ice cooling and stirring, to the solution was added 600 mg of potassium nitrate in portions. The solution was stirred at room temperature for 30 minutes to complete nitration. Then the reaction solution was poured into a stirred mixture of 150 ml of chloroform and 100 ml of ice water. After stirring at room temperature for 15 minutes, the reaction solution separated. The chloroform layer was dried over anhydrous magnesium sulfate and then concentrated in vacua. The precipitated crystals were dispersed in ethanol, collected by filtration and washed with ethanol and then with diisopropyl ether to give 2.08 g of the title compound.

Properties: colorless needles
mp: 256–257° C.
$^1$H-NMR (CDCl$_3$) δ: 1.41 (t, J=7 Hz, 3H), 4.42 (d, J=7 Hz, 1H), 7.37 (t, J=9 Hz, 1H), 8.35 (t, J=7 Hz, 1H), 8.49 (d, J=7 Hz, 1H), 8.54 (s, 1H)

EXAMPLE 2

7-chloro-6-fluoro-1-(2,4-difluoro-5-nitrophenyl)-1,4-dihydro-4-oxo-1,8-naphthyridine-3-carboxylic acid To 25 ml of conc. sulfuric acid was added 6.0 grams of 7-chloro-1-(2,4-difluorophenyl)-6-fluoro-4-oxo-1,4-dihydro-1,8-naphthyridine-3-carboxylic acid. With ice cooling and stirring, to the solution was added 5.0 g of potassium nitrate in portions. The temperature was slowly elevated to 80° C. at which stirring was continued for 2 hours. The reaction solution was allowed to cool, poured into 200 g of ice water, and allowed to stand overnight. The precipitate was collected by filtration, washed with distilled water, ethanol and diisopropyl ether, and air dried, to give 6.4 g of the title compound.

Properties: colorless powder
mp: 262–265° C.(decomposed)
$^1$H-NMR (CDCl$_3$) δ: 8.15 (t, J=11 Hz, 1H), 8.79 (d, J=7 Hz, 1H), 8.86 (t, J=8 Hz, 1H), 9.17 (s, 1H)

EXAMPLE 3

1-(2,4-difluoro-5-nitrophenyl)-6,7-difluoro-1,4-dihydro-4-oxoquinoline-3-carboxylic acid To 40 ml of conc. sulfuric acid was added 4 g of 1-(2,4-difluorophenyl)-6,7-difluoro-1,4-dihydro-4-oxoquinoline-3-carboxylic acid. Potassium nitrate (3.6 mg) was added in portions to the solution, which was stirred for 1 hour at room temperature. The reaction solution was poured into ice water and stirred overnight. The precipitated solid was collected by filtration and washed with water, ethanol and diethyl ether to give 4.2 g of the title compound.

Properties: pale yellow powder
mp: >270° C.
$^1$H-NMR (CDCl$_3$) δ:
7.70 (dd, J=6 Hz, 12 Hz, 1H), 8.21 (t, J=11 Hz, 1H), 8.36 (t, J=9 Hz, 1H), 8.93 (t, J=8 Hz, 1H), 9.10 (s, 1H)

EXAMPLE 4

Ethyl 1-(2,4-difluoro-5-nitrophenyl)-6,7-difluoro-1,4-dihydro-4-oxoquinoline-3-carboxylate To 40 ml of dichloroethane was added 4.2 g of 1-(2,4-difluoro-5-nitrophenyl)-6,7-difluoro-1,4-dihydro-4-oxoquinoline-3-carboxylic acid. With ice cooling, 7 g of oxalyl chloride was added dropwise. After the completion of addition, the solution was stirred for 2 hours at room temperature. Ethanol (15 ml) was added dropwise to the reaction solution, which was stirred overnight at room temperature. The reaction solution was concentrated in vacua, ethanol was added to the residue, and the solid was collected by filtration and washed with diethyl ether to give 3.7 g of the title compound.

Properties: pale yellow powder
mp: 165–173° C.
$^1$H-NMR (d$_6$-DMSO) δ: 2.74 (t, J=7 Hz, 3H), 4.37 (q, J=7 Hz, 2H), 7.47 (dd, J=10 Hz, 11 Hz, 1H), 8.11–8.24 (m, 2H), 8.72 (s, 1H), 8.93 (t, J=9 Hz, 1H)

EXAMPLE 5

1-(2,4-difluoro-5-nitrophenyl)-6,7,8-trifluoro-1,4-dihydro-4-oxoquinoline-3-carboxylic acid To 10 ml of conc. sulfuric acid was added 1.7 g of 1-(2,4-difluorophenyl)-6,7,8-trifluoro-1,4-dihydro-4-oxoquinoline-3-carboxylic acid. Potassium nitrate (1.5 g) was added in portions to the solution, which was heated at 60° C. and stirred overnight. The reaction solution was allowed to cool down, poured into ice water, and stirred overnight. The precipitated solid was collected by filtration and washed with water, ethanol and diethyl ether to give 1.7 g of the title compound.

Properties: pale yellow powder
mp: 245–255° C.
$^1$H-NMR ($d_6$-DMSO) δ: 8.17 (t, J=10 Hz, 1H), 8.26 (t, J=9 Hz, 1H), 8.97 (s, 1H), 9.00 (t, J=8 Hz, 1H)

EXAMPLE 6

Ethyl 1-(2,4-difluoro-5-nitrophenyl)-6,7,8-trifluoro-1,4-dihydro-4-oxoquinoline-3-carboxylate The title compound was obtained by the similar procedure as Example 4 except that 1-(2,4-difluoro-5-nitrophenyl)-6,7,8-trifluoro-1,4-dihydro-4-oxoquinoline-3-carboxylic acid was used.

Properties: colorless powder
mp: 210–217° C.
$^1$H-NMR ($d_6$-DMSO) δ: 1.27 (t, J=7 Hz, 3H), 4.26 (q, J=7 Hz, 2H), 8.07 (t, J=11 Hz, 1H), 8.16 (t, J=10 Hz, 1H), 8.64 (s, 1H), 9.00 (t, J=8 Hz, 1H)

EXAMPLE 7

7-chloro-6-fluoro-1,4-dihydro-4-oxo-1-(2,3,4-trifluoro-5-nitrophenyl)-1,8-naphthyridine-3-carboxylic acid To 10 ml of conc. sulfuric acid was added 890 mg of 7-chloro-6-fluoro-1,4-dihydro-4-oxo-1-(2,3,4-trifluorophenyl)-1,8-naphthyridine-3-carboxylic acid. Potassium nitrate (730 mg) was added in portions to the solution, which was stirred at room temperature for 2 days. The reaction solution was allowed to cool, poured into ice water, and stirred overnight. The precipitated solid was collected by filtration, washed with water, ethanol and diethyl ether to give 860 mg of the title compound.

Properties: yellow powder
mp: 216–221° C.
$^1$H-NMR ($d_6$-DMSO) δ: 8.72–8.84 (m, 2H), 9.11 (s, 1H)

EXAMPLE 8

Ethyl 7-chloro-6-fluoro-1,4-dihydro-4-oxo-1-(2,3,4-trifluoro-5-nitrophenyl)-1,8-naphthyridine-3-carboxylate The title compound was obtained by the similar procedure as Example 4 except that 7-chloro-6-fluoro-1,4-dihydro-4-oxo-1-(2,3,4-trifluoro-5-nitrophenyl)-1,8-naphthyridine-3-carboxylic acid was used.

$^1$H-NMR (CDCl$_3$) δ: 1.41 (t, J=7 Hz, 3H), 4.42 (q, J=7 Hz, 2H), 8.18–8.26 (m, 1H), 8.59 (d, J=8 Hz, 1H), 8.54 (s, 1H)

EXAMPLE 9

6,7-difluoro-1,4-dihydro-4-oxo-1-(2,3,4-trifluoro-5-nitrophenyl)-quinoline-3-carboxylic acid To 10 ml of conc. sulfuric acid was added 830 mg of 6,7-difluoro-1,4-dihydro-4-oxo-1-(2,3,4-trifluorophenyl)-quinoline-3-carboxylic acid. Potassium nitrate (710 mg) was added in portions to the solution, which was stirred at 100° C. for 3 days. The reaction solution was allowed to cool, poured into ice water, and stirred overnight. The precipitated solid was collected by filtration, washed with water, ethanol and diethyl ether to give 700 mg of the title compound.

Properties: pale yellow powder
mp: >215° C. (decomposed)
$^1$H-NMR ($d_6$-DMSO) δ: 7.76 (dd, J=6 Hz, 11 Hz, 1H), 8.37 (t, J=9 Hz, 1H), 8.85 (t, J=6 Hz, 1H), 9.07 (s, 1H)

EXAMPLE 10

Ethyl 6,7-difluoro-1,4-dihydro-4-oxo-1-(2,3,4-trifluoro-5-nitrophenyl)-quinoline-3-carboxylate The title compound was obtained by the similar procedure as Example 4 except that 6,7-difluoro-1,4-dihydro-4-oxo-1-(2,3,4-trifluoro-5-nitrophenyl)-quinoline-3-carboxylic acid was used.

Properties: colorless powder
mp: 106–115° C.
$^1$H-NMR (CDCl$_3$) δ: 1.27 (t, J=7 Hz, 3H), 4.24 (q, J=7 Hz, 2H), 7.53 (dd, J=6 Hz, 11 Hz, 1H), 8.16 (t, J=10 Hz, 1H), 8.69 (s, 1H), 8.83 (t, J=8 Hz, 1H)

EXAMPLE 11

Ethyl 7-chloro-6-fluoro-1,4-dihydro-4-oxo-1-(2,4,6-trifluoro-3-nitrophenyl)-1,8-naphthyridine-3-carboxylate The title compound was obtained by the similar procedure as Example 1 except that ethyl 7-chloro-6-fluoro-1,4-dihydro-4-oxo-1-(2,4,6-trifluorophenyl)-1,8-naphthyridine-3-carboxylate was used.

Properties: yellow powder
mp: 177–184° C.
$^1$H-NMR (CDCl$_3$) δ: 1.42 (t, J=7 Hz, 3H), 4.43 (q, J=7 Hz, 2H), 7.24 (t, J=11 Hz, 2H), 8.49 (s, 1H), 8.50 (d, J=10 Hz, 1H)

EXAMPLE 12

Ethyl 7-chloro-1-(2-chloro-4-fluoro-5-nitrophenyl)-6-fluoro-1,4-dihydro-4-oxo-1,8-naphthyridine-3-carboxylate The title compound was obtained by the similar procedure as Example 1 except that ethyl 7-chloro-1-(2-chloro-4-fluorophenyl)-6-fluoro-1,4-dihydro-4-oxo-1,8-naphthyridine-3-carboxylate was used.

Properties: colorless needles
mp: 237–242° C. (decomposed)
$^1$H-NMR (CDCl$_3$) δ: 1.41 (t, J=7 Hz, 3H), 4.40 (q, J=7 Hz, 2H), 7.62 (d, J=10 Hz, 1H), 8.19 (d, J=8 Hz, 1H), 8.50 (d, J=8 Hz, 1H), 8.55 (s, 1H)

EXAMPLE 13

Ethyl 1-(2-chloro-4-fluoro-5-nitrophenyl)-6,7-difluoro-1,4-dihydro-4-oxoquinoline-3-carboxylate The title compound was obtained by the similar procedure as Example 1 except that ethyl 1-(2-chloro-4-fluorophenyl)-6,7-difluoro-1,4-dihydro-4-oxoquinoline-3-carboxylate was used.

Properties: pale yellow needles
mp: 216–219° C.
¹H-NMR (CDCl₃) δ: 1.41 (t, J=7 Hz, 3H), 4.40 (q, J=7 Hz, 2H), 6.53 (dd, J=6 Hz, 12 Hz, 1H), 7.77 (d, J=11 Hz, 1H), 8.32 (s, 1H), 8.26–8.35 (m, 1H), 8.40 (d, J=7 Hz, 1H)

EXAMPLE 14

Ethyl 7-chloro-1-(4-chloro-2-fluoro-5-nitrophenyl)-6-fluoro-1,4-dihydro-4-oxo-1,8-naphthyridine-3-carboxylate The title compound was obtained by the similar procedure as Example 1 except that ethyl 7-chloro-1-(4-chloro-2-fluorophenyl)-6-fluoro-1,4-dihydro-4-oxo-1,8-naphthyridine-3-carboxylate was used.
Properties: colorless needles
mp: 219–221° C.
¹H-NMR (CDCl₃) δ: 1.41 (t, J=7 Hz, 3H), 4.40 (q, J=7 Hz, 2H), 7.62 (d, J=10 Hz, 1H), 8.19 (d, J=8 Hz, 1H), 8.50 (d, J=8 Hz, 1H), 8.55 (s, 1H)

EXAMPLE 15

Ethyl 7-chloro-6-fluoro-1-(4-fluoro-2-methyl-5-nitrophenyl)-1,4-dihydro-4-oxo-1,8-naphthyridine-3-carboxylate The title compound was obtained by the similar procedure as Example 1 except that ethyl 7-chloro-6-fluoro-1-(4-fluoro-2-methylphenyl)-1,4-dihydro-4-oxo-1,8-naphthyridine-3-carboxylate was used.
Properties: colorless powder
mp: 215–216° C.
¹H-NMR (CDCl₃) δ: 1.41 (t, J=7 Hz, 3H), 2.19 (s, 1H), 4.43 (q, J=7 Hz, 2H), 7.41 (d, J=8 Hz, 1H), 8.11 (d, J=7 Hz, 1H), 8.50 (s, 1H), 8.52 (d, J=8 Hz, 1H)

EXAMPLE 16

Ethyl 1-(3-amino-4,6-difluorophenyl)-7-chloro-6-fluoro-1,4-dihydro-4-oxo-1,8-naphthyridine-3-carboxylate Ethyl 7-chloro-6-fluoro-1-(2,4-difluoro-5-nitrophenyl)-1,4-dihydro-4-oxo-1,8-naphthyridine-3-carboxylate (3.0 g) was added to a mixture of 50 ml of dichloromethane, 30 ml of ethanol, and 2 ml of conc. hydrochloric acid together with 280 mg of 10% palladium on carbon whereupon hydrogenation was carried out overnight at room temperature. Pyridine (2 ml) was added to the reaction solution, which was concentrated in vacua. To the residue were added 80 ml of chloroform and 10 ml of distilled water. The chloroform layer was separated, dried over anhydrous magnesium sulfate and then concentrated in vacua. Ethanol (8 ml) was added to the residue whereupon the solution was allowed to stand at room temperature. The precipitate was collected by filtration and washed with ethanol and then with diisopropyl ether to give 1.95 grams of the title compound.
Properties: colorless powder
mp: 208–210° C.
¹H-NMR (d₆-DMSO) δ: 1.27 (t, J=7 Hz, 3H), 4.24 (q, J=7 Hz, 2H), 7.11 (t, J=8 Hz, 1H), 7.47 (t, J=10 Hz, 1H), 8.53 (d, J=8 Hz, 1H), 8.71 (s, 1H)

EXAMPLE 17

1-(3-amino-4,6-difluorophenyl)-7-chloro-6-fluoro-1,4-dihydro-4-oxo-1,8-naphthyridine-3-carboxylic acid To 0.6 g of ethyl 1-(3-amino-4,6-difluorophenyl)-7-chloro-6-fluoro-1,4-dihydro-4-oxo-1,8-naphthyridine-3-carboxylate was added 4 ml of a 3N hydrochloric acid/acetic acid mixture. The solution was heated at reflux for 2 hours. Distilled water (3 ml) was added to the solution, which was refluxed for 5 minutes. The precipitate was collected by filtration and washed with ethanol to give 0.54 g of the title compound.
Properties: yellow powder
mp: >270° C.
¹H-NMR (d₆-DMSO) δ: 5.46 (s, 2H), 7.00 (t, J=8 Hz, 1H), 7.43 (t, J=10 Hz, 1H), 8.76 (d, J=8 Hz, 1H), 8.97 (s, 1H)

EXAMPLE 18

Ethyl 1-(3-amino-4,6-difluorophenyl)-6,7-difluoro-1,4-dihydro-4-oxoquinoline-3-carboxylate Ethyl 1-(2,4-difluoro-5-nitrophenyl)-6,7-difluoro-1,4-dihydro-4-oxoquinoline-3-carboxylate (3.7 grams) was dissolved in 60 ml of acetic acid, to which was added 400 mg of 10% palladium on carbon. Under a hydrogen atmosphere, the solution was stirred for 2 days at room temperature. The catalyst was removed by a membrane filter and the filtrate was concentrated in vacua. Ethanol was added to the residue whereupon the solid was collected by filtration and washed with diethyl ether to give 2.9 g of the title compound.
Properties: yellow powder
mp: 198–205° C.
¹H-NMR (d₆-DMSO) δ: 1.28 (t, J=7 Hz, 3H), 4.23 (q, J=7 Hz, 2H), 5.52 (s, 2H), 7.01 (t, J=9 Hz, 1H), 7.19 (dd, J=6 Hz, 10 Hz, 1H), 8.14 (t, J=9 Hz, 1H), 8.54 (s, 1H)

EXAMPLE 19

1-(3-amino-4,6-difluorophenyl)-6,7-difluoro-1,4-dihydro-4-oxoquinoline-3-carboxylic acid Ethyl 1-(3-amino-4,6-difluorophenyl)-6,7-difluoro-1,4-dihydro-4-oxoquinoline-3-carboxylate (1 g) was added to 8 ml of acetic acid and 2 ml of hydrochloric acid. The solution was heated at reflux overnight. After cooling down, the solution was concentrated in vacua. Ethanol was added to the residue whereupon the solid was collected by filtration and washed with diethyl ether to give 830 mg of the title compound.
Properties: colorless powder
mp: >270° C.
¹H-NMR (d₆-DMSO) δ: 7.14 (t, J=9 Hz, 1H), 7.47 (dd, J=6 Hz, 10 Hz, 1H), 7.54 (t, J=10 Hz, 1H), 8.34 (t, J=10 Hz, 1H), 8.89 (s, 1H)

EXAMPLE 20

Ethyl 1-(3-amino-4,6-difluorophenyl)-6,7,8-trifluoro-1,4-dihydro-4-oxoquinoline-3-carboxylate Ethyl 1-(2,4-difluoro-5-nitrophenyl)-6,7,8-trifluoro-1,4-dihydro-4-oxoquinoline-3-carboxylate (2.2 g) was dissolved in 20 ml of methanol, 50 ml of acetic acid, and 10 ml of dichloroethane, to which was added 200 mg of 10% palladium on carbon. Under a hydrogen atmosphere, the solution was stirred overnight at room temperature. The catalyst was removed by a membrane filter and the filtrate was concentrated in vacua. Ethanol was added to the residue whereupon the solid was collected by filtration and washed with diethyl ether to give 1.12 g of the title compound.
Properties: yellow powder
mp: 187–196° C.

$^1$H-NMR (d$_6$-DMSO) δ: 1.28 (t, J=7 Hz, 3H), 4.22 (q, J=7 Hz, 2H), 5.49 (s, 2H), 7.11 (t, J=8 Hz, 1H), 7.42 (t, J=10 Hz, 1H), 8.05 (t, J=10 Hz, 1H), 8.46 (s, 1H)

EXAMPLE 21

1-(3-amino-4,6-difluorophenyl)-6,7,8-trifluoro-1,4-dihydro-4-oxoquinoline-3-carboxylic acid The title compound was obtained by the similar procedure as Example 19 except that ethyl 1-(3-amino-4,6-difluorophenyl)-6,7,8-trifluoro-1,4-dihydro-4-oxoquinoline-3-carboxylate was used.

Properties: colorless powder mp: 256–261° C.

$^1$H-NMR (d$_6$-DMSO) δ: 7.15–7.30 (m, 1H), 7.49 (t, J=10 Hz, 1H), 8.25 (t, J=8 Hz, 1H), 8.77 (s, 1H)

EXAMPLE 22

Ethyl 1-(3-amino-4,5,6-trifluorophenyl)-7-chloro-6-fluoro-1,4-dihydro-4-oxo-1,8-naphthyridine-3-carboxylate Ethyl 7-chloro-6-fluoro-1,4-dihydro-4-oxo-1-(2,3,4-trifluoro-5-nitrophenyl)-1,8-naphthyridine-3-carboxylate (780 mg) was dissolved in 5 ml of methanol and 10 ml of acetic acid, to which was added 80 mg of 10% palladium on carbon. Under a hydrogen atmosphere, the solution was stirred overnight at room temperature. The catalyst was removed by a membrane filter and the filtrate was concentrated in vacua. Ethanol was added to the residue whereupon the solid was collected by filtration and washed with diethyl ether to give 200 mg of the title compound.

Properties: brown powder mp: 165–174° C. (decomposed)

$^1$H-NMR (d$_6$-DMSO) δ: 1.29 (t, J=7 Hz, 3H), 4.26 (q, J=7 Hz, 2H), 5.82 (s, 2H), 8.55 (d, J=8 Hz, 1H), 8.75 (s, 1H)

EXAMPLE 23

1-(3-amino-4,5,6-trifluorophenyl)-7-chloro-6-fluoro-1,4-dihydro-4-oxo-1,8-naphthyridine-3-carboxylic acid Ethyl 1-(3-amino-4,5,6-trifluorophenyl)-7-chloro-6-fluoro-1,4-dihydro-4-oxo-1,8-naphthyridine-3-carboxylate (600 mg) was dissolved in 30 ml of methanol, 10 ml of acetic acid, and 30 ml of dichloroethane, to which was added 100 mg of 10% palladium on carbon. Under a hydrogen atmosphere, the solution was stirred overnight at room temperature. The catalyst was removed by a membrane filter and the filtrate was concentrated in vacua. To the residue were added 4 ml of acetic acid and 1 ml of hydrochloric acid. The solution was heated at 100° C. and stirred overnight. The reaction solution was concentrated in vacua whereupon diethyl ether was added to the residue. The solid was collected by filtration and washed with diethyl ether to give 160 mg of the title compound.

Properties: pale yellow powder mp: >242° C. (decomposed)

$^1$H-NMR (d$_6$-DMSO) δ: 6.87 (t, J=5 Hz, 1H), 7.76 (d, J=8 Hz, 1H), 9.02 (s, 1H)

EXAMPLE 24

Ethyl 1-(3-amino-4,5,6-trifluorophenyl)-6,7-difluoro-1,4-dihydro-4-oxoquinoline-3-carboxylate Ethyl 6,7-difluoro-1,4-dihydro-4-oxo-1-(2,3,4-trifluoro-5-nitrophenyl)quinoline-3-carboxylate (280 mg) was dissolved in 10 ml of ethanol, 5 ml of acetic acid, and 5 ml of dichloroethane, to which was added 30 mg of 10% palladium on carbon. Under a hydrogen atmosphere, the solution was stirred overnight at room temperature. The catalyst was removed by a membrane filter and the filtrate was concentrated in vacua. Ethanol was added to the residue whereupon the solid was collected by filtration and washed with diethyl ether to give 200 mg of the title compound.

Properties: yellow powder mp: 116–124° C.

$^1$H-NMR (d$_6$-DMSO) δ: 1.27 (t, J=7 Hz, 3H), 4.22 (q, J=7 Hz, 2H), 5.85 (s, 2H), 6.83 (t, J=8 Hz, 1H), 7.42 (dd, J=6 Hz, 12 Hz, 1H), 8.13 (t, J=10 Hz, 1H), 8.60 (s, 1H)

EXAMPLE 25

1-(3-amino-4,5,6-trifluorophenyl)-6,7-difluoro-1,4-dihydro-4-oxoquinoline-3-carboxylic acid The title compound was obtained by the similar procedure as Example 23 except that ethyl 1-(3-amino-4,5,6-trifluorophenyl)-6,7-difluoro-1,4-dihydro-4-oxoquinoline-3-carboxylate was used.

Properties: pale yellow powder mp: >211° C. (decomposed)

$^1$H-NMR (d$_6$-DMSO) δ: 5.91 (brs, 2H), 6.86 (t, J=7 Hz, 1H), 7.68 (dd, J=7 Hz, 11 Hz, 1H), 8.34 (t, J=9 Hz, 1H), 8.94 (s, 1H)

EXAMPLE 26

Ethyl 1-(3-amino-2,4,6-trifluorophenyl)-7-chloro-6-fluoro-1,4-dihydro-4-oxo-1,8-naphthyridine-3-carboxylate The title compound was obtained by the similar procedure as Example 16 except that ethyl 1-(2,4,6-trifluoro-3-nitrophenyl)-7-chloro-6-fluoro-1,4-dihydro-4-oxo-1,8-naphthyridine-3-carboxylate was used.

$^1$H-NMR (CDCl$_3$) δ: 1.40 (t, J=7 Hz, 3H), 4.40 (q, J=7 Hz, 2H), 6.83–7.04 (br, 2H), 7.22–7.35 (m, 1H), 8.48 (d, J=8 Hz, 1H), 8.50 (s, 1H)

EXAMPLE 27

1-(3-amino-2,4,6-trifluorophenyl)-7-chloro-6-fluoro-1,4-dihydro-4-oxo-1,8-naphthyridine-3-carboxylic acid The title compound was obtained by the similar procedure as Example 17 except that ethyl 1-(3-amino-2,4,6-trifluorophenyl)-7-chloro-6-fluoro-1,4-dihydro-4-oxo-1,8-naphthyridine-3-carboxylate was used.

Properties: pale yellow powder mp: 222–228° C.

$^1$H-NMR (d$_6$-DMSO) δ: 7.44 (t, J=11 Hz, 1H), 8.77 (d, J=8 Hz, 1H), 9.21 (s, 1H)

EXAMPLE 28

Ethyl 1-(3-amino-6-chloro-4-fluorophenyl)-7-chloro-6-fluoro-1,4-dihydro-4-oxo-1,8-naphthyridine-3-carboxylate The title compound was obtained by the similar procedure as Example 16 except that ethyl 1-(6-chloro-4-fluoro-3-nitrophenyl)-7-chloro-6-fluoro-1,4-dihydro-4-oxo-1,8-naphthyridine-3-carboxylate was used.

Properties: yellow powder mp: 206–208° C.

$^1$H-NMR (CDCl$_3$) δ: 1.41 (t, J=7 Hz, 3H), 4.40 (q, J=7 Hz, 2H), 6.86 (d, J=8 Hz, 1H), 7.26 (d, J=11 Hz, 1H), 8.48 (d, J=8 Hz, 1H), 8.49 (s, 1H)

EXAMPLE 29

1-(3-amino-6-chloro-4-fluorophenyl)-7-chloro-6-fluoro-1,4-dihydro-4-oxo-1,8-naphthyridine-3-carboxylic acid The title compound was obtained by the similar procedure as Example 17 except that ethyl 1-(3-amino-6-chloro-4-fluorophenyl)-7-chloro-6-fluoro-1,4-dihydro-4-oxo-1,8-naphthyridine-3-carboxylate was used.

Properties: pale yellow powder mp: 265–267° C.

$^1$H-NMR (d$_6$-DMSO) δ: 5.81 (s, 2H), 7.07 (d, J=8 Hz, 1H), 7.52 (d, J=11 Hz, 1H), 8.76 (d, J=7 Hz, 1H), 8.93 (s, 1H)

EXAMPLE 30

Ethyl 1-(3-amino-6-chloro-4-fluorophenyl)-6,7-difluoro-1,4-dihydro-4-oxoquinoline-3-carboxylate The title compound was obtained by the similar procedure as Example 16 except that ethyl 1-(6-chloro-4-fluoro-3-nitrophenyl)-6,7-difluoro-1,4-dihydro-4-oxoquinoline-3-carboxylate was used.

$^1$H-NMR (CDCl$_3$) δ: 1.39 (t, J=7 Hz, 3H), 4.38 (q, J=7 Hz, 2H), 6.65 (dd, J=5 Hz, 12 Hz, 1H), 6.91 (d, J=9 Hz, 1H), 7.31 (d, J=11 Hz, 1H), 8.28 (q, J=9 Hz, 16 Hz, 1H), 8.35 (s, 1H)

EXAMPLE 31

1-(3-amino-6-chloro-4-fluorophenyl)-6,7-difluoro-1,4-dihydro-4-oxoquinoline-3-carboxylic acid The title compound was obtained by the similar procedure as Example 19 except that ethyl 1-(3-amino-6-chloro-4-fluorophenyl)-6,7-difluoro-1,4-dihydro-4-oxoquinoline-3-carboxylate was used.

Properties: colorless powder mp: >270° C.

$^1$H-NMR (d$_6$-DMSO) δ: 5.91 (brs, 1H), 7.08 (d, J=8 Hz, 1H), 7.34 (dd, J=7 Hz, 11 Hz, 1H), 7.59 (d, J=12 Hz, 1H), 8.35 (t, J=11 Hz, 1H), 8.83 (s, 1H)

EXAMPLE 32

Ethyl 1-(3-amino-4-chloro-6-fluorophenyl)-7-chloro-6-fluoro-1,4-dihydro-4-oxo-1,8-naphthyridine-3-carboxylate The title compound was obtained by the similar procedure as Example 16 except that ethyl 1-(4-chloro-6-fluoro-3-nitrophenyl)-7-chloro-6-fluoro-1,4-dihydro-4-oxo-1,8-naphthyridine-3-carboxylate was used.

Properties: pale yellow powder mp: 200–202° C.

$^1$H-NMR (CDCl$_3$) δ: 1.40 (t, J=7 Hz, 3H), 4.40 (q, J=7 Hz, 2H), 6.82 (d, J=7 Hz, 1H), 7.29 (d, J=11 Hz, 1H), 8.47 (d, J=8 Hz, 1H), 8.55 (s, 1H)

EXAMPLE 33

1-(3-amino-4-chloro-6-fluorophenyl)-7-chloro-6-fluoro-1,4-dihydro-4-oxo-1,8-naphthyridine-3-carboxylic acid Ethyl 1-(3-amino-4-chloro-6-fluorophenyl)-7-chloro-6-fluoro-1,4-dihydro-4-oxo-1,8-naphthyridine-3-carboxylate (1.00 g) was dissolved in 10 ml of acetic acid, 10 ml of methanol and 20 ml of dichloroethane, to which was added a suspension of 132 mg of 10% palladium on carbon in 20 ml of acetic acid. Under a hydrogen atmosphere, the solution was stirred overnight. The palladium on carbon was removed by a membrane filter and 10% sodium hydroxide was added to the filtrate, which was extracted with chloroform. The organic layer was dried, and the solvent was distilled off. The solid was collected by filtration, to give 0.380 g of the title compound.

Properties: pale yellow powder mp: >270° C.

$^1$H-NMR (d$_6$-DMSO) δ: 5.76 (br, 2H), 7.03 (d, J=9 Hz, 1H), 7.57 (d, J=10 Hz, 1H), 8.78 (d, J=8 Hz, 1H), 9.00 (s, 1H)

EXAMPLE 34

Ethyl 1-(3-amino-4-fluoro-2-methylphenyl)-7-chloro-6-fluoro-1,4-dihydro-4-oxo-1,8-naphthyridine-3-carboxylate The title compound was obtained by the similar procedure as Example 16 except that ethyl 1-(4-fluoro-2-methyl-3-nitrophenyl)-7-chloro-6-fluoro-1,4-dihydro-4-oxo-1,8-naphthyridine-3-carboxylate was used.

Properties: pale yellow powder mp: 212–213° C.

$^1$H-NMR (CDCl$_3$) δ: 1.41 (t, J=7 Hz, 3H), 1.91 (s, 3H), 3.79–3.96 (br, 2H), 4.40 (q, J=7 Hz, 2H), 6.70 (d, J=8 Hz, 1H), 7.02 (d, J=11 Hz, 1H), 8.50 (d, J=11 Hz, 1H), 8.50 (s, 1H)

EXAMPLE 35

1-(3-amino-4-fluoro-2-methylphenyl)-7-chloro-6-fluoro-1,4-dihydro-4-oxo-1,8-naphthyridine-3-carboxylic acid The title compound was obtained by the similar procedure as Example 17 except that ethyl 1-(3-amino-4-fluoro-2-methylphenyl)-7-chloro-6-fluoro-1,4-dihydro-4-oxo-1,8-naphthyridine-3-carboxylate was used.

Properties: colorless powder mp: 274–279° C.

$^1$H-NMR (d$_6$-DMSO) δ: 1.84 (s, 3H), 6.95 (d, J=8 Hz, 1H), 7.19 (d, J=12 Hz, 1H), 8.75 (d, J=8 Hz, 1H), 8.79 (s, 1H)

EXAMPLE 36

Ethyl 7-chloro-1-(2,4-difluoro-5-formylaminophenyl)-6-fluoro-1,4-dihydro-4-oxo-1,8-naphthyridine-3-carboxylate Ethyl 7-chloro-6-fluoro-1-(2,4-difluoro-5-nitrophenyl)-4-oxo-1,4-dihydro-1,8-naphthyridine-3-carboxylate (3.5 g) was added to a mixture of 20 ml of dichloromethane, 10 ml of formic acid, and 0.3 ml of conc. hydrochloric acid together with 280 mg of 10% palladium on carbon whereupon hydrogenation was carried out at room temperature for 5 hours. Acetic anhydride (1.2 ml) was added to the reaction solution, which was allowed to stand for 1 hour at room temperature. After removal of the catalyst by filtration, the solution was concentrated in vacua. The precipitate was dispersed in ethanol, collected by filtration and washed with ethanol and then with diisopropyl ether to give 2.65 g of the title compound.

Properties: colorless powder mp: >270° C.

$^1$H-NMR (d$_6$-DMSO) δ: 1.28 (t, J=7 Hz, 3H), 4.25 (q, J=7 Hz, 2H), 7.77 (dd, J=10 Hz, 11 Hz, 1H), 8.35 (s, 1H), 8.45 (t, J=8 Hz, 1H), 8.54 (d, J=8 Hz, 1H), 8.77 (s, 1H)

EXAMPLE 37

7-chloro-1-(2,4-difluoro-5-formylaminophenyl)-6-fluoro-1,4-dihydro-4-oxo-1,8-naphthyridine-3-carboxylic acid In 1 ml of formic acid was dissolved 465 mg of 1-(3-amino-4,6-difluorophenyl)-7-chloro-6-fluoro-4-oxo-1,4-dihydro-1,8-naphthyridine-3-carboxylic acid. Acetic anhydride (0.2 g) was added to the solution, which was stirred at 60° C. for 1 hour. The solution was concentrated in vacua, 2 ml of ethanol was added to the residue, and the resulting solution was stirred at 60° C. for 2 hours. The precipitate was collected by filtration and washed with ethanol and then with diisopropyl ether to give 450 mg of the title compound.

Properties: colorless powder mp: >270° C.

$^1$H-NMR (d$_6$-DMSO) δ: 3.46 (brs, 1H), 7.78 (dd, J=10 Hz, 11 Hz, 1H), 8.35 (s, 1H), 8.50 (t, J=8 Hz, 1H), 8.76 (d, J=8 Hz, 1H), 9.08 (s, 1H)

EXAMPLE 38

Ethyl 7-chloro-1-(2,4-difluoro-5-formylmethylaminophenyl)-6-fluoro-1,4-dihydro-4-oxo-1,8-naphthyridine-3-carboxylate Ethyl 7-chloro-1-(2,4-difluoro-5-formylaminophenyl)-6-fluoro-1,4-dihydro-4-oxo-1,8-naphthyridine-3-carboxylate (500 mg) was added to 2.5 ml of N,N-dimethylformamide together with 500 mg of potassium carbonate and 1.5 g of methyl iodide. The solution was stirred at 50° C. for 1 hour. After 40 ml of chloroform and 150 ml of distilled water were added, the organic layer was separated, dried over anhydrous magnesium sulfate, and then concentrated in vacua. The precipitate was dispersed in ethanol, collected by filtration and washed with ethanol and then with diisopropyl ether to give 455 mg of the title compound.

Properties: colorless crystals mp: 264–267° C.

$^1$H-NMR (CDCl$_3$) δ: 1.41 (t, J=7 Hz, 3H), 3.34 (s, 3H), 4.42 (q, J=7 Hz, 2H), 7.27 (t, J=10 Hz, 1H), 7.39 (t, J=7 Hz, 1H), 8.35 (s, 1H), 8.49 (d, J=7 Hz, 1H), 8.56 (s, 1H)

EXAMPLE 39

Ethyl 1-(3-t-butoxycarbonylamino-2,4-difluorophenyl)-7-chloro-6-fluoro-1,4-dihydro-4-oxo-1,8-naphthyridine-3-carboxylate Using 0.2 g of 10% palladium on carbon, 2.0 g of N-(t-butoxycarbonyl)-2,6-difluoro-3-nitroaniline was hydrogenated in 20 ml of methanol at room temperature for 3 days. After the catalyst was filtered off, the filtrate was directly added to 20 ml of a dichloromethane solution containing 0.5 mmol/ml of ethyl 2-(2',6'-dichloro-5-fluoronicotinoyl)-3-ethoxyacrylate. The solution was concentrated in vacua, 2.5 g of anhydrous potassium carbonate and 10 ml of N,N-dimethylformamide were added to the residue, and the resulting solution was stirred at 90° C. for 30 minutes. The solution was allowed to cool down and combined with 100 ml of chloroform and 400 ml of distilled water. The solution was separated, the chloroform layer was washed twice with 400 ml of distilled water, dried over anhydrous magnesium sulfate and then concentrated in vacua. Ethanol (1 ml) was added to the concentrate, which was allowed to stand. The residue was subject to chromatography using 150 g of silica gel (eluting solution: chloroform–chloroform/methanol=7.5/1). A precipitate from a fraction corresponding to a main product was dispersed in ethanol and collected by filtration to give 575 mg of the title compound.

Properties: colorless crystals mp: 128–131° C.

$^1$H-NMR (CDCl$_3$) δ: 1.40 (t, J=7 Hz, 3H), 1.51 (s, 9H), 4.40 (q, J=7 Hz, 2H), 6.11 (s, 1H), 7.16 (t, J=11 Hz, 1H), 7.30 (t, J=7 Hz, 1H), 8.48 (d, J=7 Hz, 1H), 8.54 (s, 1H)

EXAMPLE 40

1-(3-amino-2,4-difluorophenyl)-7-chloro-6-fluoro-1,4-dihydro-4-oxo-1,8-naphthyridine-3-carboxylic acid Ethyl 1-(3-t-butoxycarbonylamino-2,4-difluorophenyl)-7-chloro-6-fluoro-1,4-dihydro-4-oxo-1,8-naphthyridine-3-carboxylate (500 mg) was added to 8 ml of a mixture of 3N hydrochloric acid and acetic acid, which was stirred and heated at reflux for 3.5 hours. After 16 ml of distilled water was added, the reaction solution was heated at reflux for 10 minutes, then allowed to cool down, and combined with 80 ml of chloroform and 10 ml of distilled water. The solution was separated, the chloroform layer was concentrated in vacua. The precipitate was dispersed in ethanol, collected by filtration, and washed with ethanol and then with diisopropyl ether to give 295 mg of the title compound.

Properties: yellow powder mp: 244–248° C. (decomposed)

$^1$H-NMR (CDCl$_3$) δ: 4.04 (s, 1H), 6.64 (dt, J=5 Hz, 8 Hz, 1H), 7.02 (ddd, J=2 Hz, 8 Hz, 10 Hz, 1H), 8.52 (d, J=7 Hz, 1H), 8.87 (s, 1H)

EXAMPLE 41

1-(3-benzoylamino-4,6-difluorophenyl)-7-chloro-6-fluoro-1,4-dihydro-4-oxo-1,8-naphthyridine-3-carboxylic acid 1-(3-amino-4,6-difluorophenyl)-7-chloro-6-fluoro-4-oxo-1,4-dihydro-1,8-naphthyridine-3-carboxylic acid (310 mg) was added to 920 mg of N,N-dimethylformamide together with 220 mg of benzoic anhydride, which was stirred at 70° C. for 2 hours and at 100° C. for 2.5 hours. The reaction solution was combined with 50 ml of chloroform and 150 ml of distilled water. The solution was separated, the chloroform layer was dried over anhydrous magnesium sulfate and concentrated in vacua. Ethanol (6 ml) was added to the residue, which was allowed to stand. The precipitate was collected by filtration and washed with ethanol and then with diisopropyl ether to give 184 mg of the title compound.

Properties: pale brown powder mp: 260–263° C.

$^1$H-NMR (d$_6$-DMSO) δ: 7.53–7.68 (m, 3H), 7.80 (t, J=10 Hz, 1H), 7.98 (d, J=8 Hz, 2H), 8.11 (t, J=7 Hz, 1H), 9.09 (s, 1H), 10.40 (s, 1H)

EXAMPLE 42

Ethyl 7-chloro-1-(2,4-difluoro-5-methylaminophenyl)-6-fluoro-1,4-dihydro-4-oxo-1,8-naphthyridine-3-carboxylate Ethyl 1-(5-amino-2,4-difluorophenyl)-7-chloro-6-fluoro-4-oxo-1,4-dihydro-1,8-naphthyridine-3-carboxylate (500 mg) was added to a mixture of 10 ml of 1,2-dichloroethane, 5 ml of methanol and 0.5 ml of acetic acid together with 100 mg of 37% formalin. Using 0.08 g of 10% palladium on carbon, hydrogenation was carried out for 16 hours. After the catalyst was filtered off, the filtrate was concentrated in vacua. The residue was dissolved in 50 ml of chloroform, washed with an aqueous solution of 50% sodium carbonate, dried over anhydrous magnesium sulfate, and then concentrated in vacua. The residue was subject to chromatography using 20 g of silica gel (eluting solution: chloroform) to give 150 mg of the title compound.

Properties: pale yellow needles mp: 226–231° C.

$^1$H-NMR (CDCl$_3$) δ: 1.41 (t, J=7 Hz, 3H), 2.89 (s, 3H), 4.41 (q, J=7 Hz, 2H), 6.64 (t, J=7 Hz, 1H), 7.02 (dd, J=9 Hz, 11 Hz, 1H), 8.47 (d, J=7 Hz, 1H), 8.59 (s, 1H)

EXAMPLE 43

7-chloro-1-(2,4-difluoro-5-methylaminophenyl)-6-fluoro-1,4-dihydro-4-oxo-1,8-naphthyridine-3-carboxylic acid Ethyl 7-chloro-1-(2,4-difluoro-5-methylaminophenyl)-6-fluoro-4-oxo-1,4-dihydro-1,8-naphthyridine-3-carboxylate (150 mg) was added to 1 ml of a mixture of 3N hydrochloric acid and acetic acid (1/1, vol/vol), which was stirred and heated at reflux for 2 hours. After 5 ml of distilled water was added, the reaction solution was heated at reflux for a further 10 minutes and then allowed to cool down. The precipitate was dispersed in ethanol, collected by filtration, and washed with ethanol and then with diisopropyl ether to give 70 mg of the title compound.

Properties: yellow crystals mp: 250–252° C.

$^1$H-NMR (d$_6$-DMSO) δ: 2.69 (d, J=5 Hz, 3H), 5.90 (brs, 1H), 7.01 (t, J=8 Hz, 1H), 7.46 (t, J=11 Hz, 1H), 8.76 (d, J=8 Hz, 1H), 8.99 (s, 1H)

EXAMPLE 44

Ethyl 1-(2,4-difluoro-5-methylaminophenyl)-6,7-difluoro-1,4-dihydro-4-oxoquinoline-3-carboxylate The title compound was obtained by the similar procedure as Example 42 except that ethyl 1-(3-amino-4,6-difluorophenyl)-6,7-difluoro-1,4-dihydro-4-oxoquinoline-3-carboxylate was used.

Properties: yellow powder mp: 208–216° C.

$^1$H-NMR (d$_6$-DMSO) δ: 1.28 (t, J=7 Hz, 3H), 2.72 (d, J=4 Hz, 3H), 4.23 (q, J=7 Hz, 2H), 5.94–6.04 (m, 1H), 7.04 (t, J=8 Hz, 1H), 7.19 (dd, J=4 Hz, 10 Hz, 1H), 7.52 (t, J=10 Hz, 1H), 8.14 (t, J=10 Hz, 1H), 8.55 (s, 1H)

EXAMPLE 45

1-(2,4-difluoro-5-methylaminophenyl)-6,7-difluoro-1,4-dihydro-4-oxoquinoline-3-carboxylic acid The title compound was obtained by the similar procedure as Example 43 except that ethyl 1-(2,4-difluoro-5-methylaminophenyl)-6,7-difluoro-1,4-dihydro-4-oxoquinoline-3-carboxylate was used.

Properties: brown powder mp: >164° C. (decomposed)

$^1$H-NMR (d$_6$-DMSO) δ: 2.71 (s, 3H), 6.01 (brs, 1H), 7.05 (t, J=8 Hz, 1H), 7.39–7.51 (m, 1H), 7.53 (t, J=10 Hz, 1H), 8.34 (t, J=9 Hz, 1H), 8.90 (s, 1H)

EXAMPLE 46

Ethyl 7-chloro-1-(3-dimethylamino-4,6-difluorophenyl)-6-fluoro-1,4-dihydro-4-oxo-1,8-naphthyridine-3-carboxylate Ethyl 1-(3-amino-4,6-difluorophenyl)-7-chloro-6-fluoro-4-oxo-1,4-dihydro-1,8-naphthyridine-3-carboxylate (500 mg) was added to a mixture of 10 ml of 1,2-dichloroethane, 5 ml of methanol and 0.5 ml of acetic acid together with 500 mg of 37% formalin. Using 0.08 g of 10% palladium on carbon, hydrogenation was carried out 64 hours. After the catalyst was filtered off, the filtrate was concentrated in vacua, to give the title compound.

Properties: yellow powder mp: 158–163° C.

$^1$H-NMR (CDCl$_3$) δ:

1.41 (t, J=7 Hz, 3H), 2.88 (s, 6H), 4.41 (q, J=7 Hz, 2H), 6.85 (t, J=7 Hz, 1H), 7.04 (dd, J 9 Hz, 12 Hz, 1H), 8.47 (d, J=7 Hz, 1H), 8.57 (s, 1H)

EXAMPLE 47

7-chloro-1-(3-dimethylamino-4,6-difluorophenyl)-6-fluoro-1,4-dihydro-4-oxo-1,8-naphthyridine-3-carboxylic acid The entire amount of ethyl 7-chloro-1-(3-dimethylamino-4,6-difluorophenyl)-6-fluoro-4-oxo-1,4-dihydro-1,8-naphthyridine-3-carboxylate obtained in Example 46 was added to 4 ml of a mixture of 3N hydrochloric acid and acetic acid (1/1, vol/vol), which was stirred and heated at reflux for 2 hours. The reaction solution was allowed to cool down and concentrated in vacua. The precipitate was dispersed in ethanol, collected by filtration, and washed with ethanol and then with diisopropyl ether to give 295 mg of the title compound.

Properties: pale yellow powder mp: 244–247.0° C.

$^1$H-NMR (d$_6$-DMSO) δ: 2.79 (s, 6H), 7.41 (t, J=8 Hz, 1H), 7.57 (dd, J=10 Hz, 13 Hz, 1H), 8.77 (d, J=8 Hz, 1H), 9.04 (s, 1H)

EXAMPLE 48

1-(3-amino-4,6-difluorophenyl)-7-[(3S)-3-aminopyrrolidin-1-yl]-6-fluoro-1,4-dihydro-4-oxo-1,8-naphthyridine-3-carboxylic acid To 6,500 mg of N,N-dimethylformamide were added 1,300 mg of 1-(3-amino-4,6-difluorophenyl)-7-chloro-6-fluoro-4-oxo-1,4-dihydro-1,8-naphthyridine-3-carboxylic acid, 600 mg of (3S)-3-aminopyrrolidine, and 1,000 mg of triethylamine. The solution was stirred at 90° C. for 1 hour. The reaction solution was allowed to cool down, combined with 25 ml of ethanol, heated at reflux for 5 minutes, and allowed to cool down. The precipitate was collected by filtration and washed with ethanol and then with diisopropyl ether to give 1,410 mg of the title compound.

Properties: pale brown powder mp: 260–266° C. (decomposed)

$^1$H-NMR (d$_6$-DMSO) δ: 1.81 (m, 1H), 2.06 (m, 1H), 5.36 (brs, 2H), 6.97 (t, J=8 Hz, 1H), 7.35 (t, J=10 Hz, 1H), 8.06 (d, J=13 Hz, 1H), 8.69 (s, 1H)

EXAMPLE 49

1-(3-amino-4,6-difluorophenyl)-7-[(3S)-3-aminopyrrolidin-1-yl]-6-fluoro-1,4-dihydro-4-oxo-1,8-naphthyridine-3-carboxylic acid triethylamine salt To 1,000 mg of N,N-dimethylformamide were added 220 mg of 1-(3-amino-4,6-difluorophenyl)-7-chloro-6-fluoro-4- oxo-1,4-dihydro-1,8-naphthyridine-3-carboxylic acid, 210 mg of (3S)-3-aminopyrrolidine dihydrochloride, and 400 mg of triethylamine. The solution was stirred at 90° C. for 1.5 hours. The reaction solution was allowed to cool down, combined with 10 ml of ethanol, heated at reflux for 5 minutes, and allowed to cool down. The precipitate was collected by filtration and washed with ethanol and then with diisopropyl ether to give 220 mg of the title compound.

Properties: pale brown powder mp: 245–249° C. (decomposed)

$^1$H-NMR (d$_6$-DMSO) δ: 1.06 (t, J=7 Hz, 9H), 1.66 (m, 1H), 1.92 (m, 1H), 3.44 (q, J=7 Hz, 6H), 5.35 (s, 2H), 6.96 (t, J=8 Hz, 1H), 7.35 (t, J=10 Hz, 1H), 8.02 (d, J=13 Hz, 1H), 8.66 (s, 1H)

EXAMPLE 50

1-(3-amino-4,6-difluorophenyl)-7-[(3S)-3-aminopyrrolidin-1-yl]-6-fluoro-1,4-dihydro-4-oxo-1,8-naphthyridine-3-carboxylic acid dihydrochloride In 2.5 ml of 6N hydrochloric acid was dissolved 100 mg of 1-(3-amino-4,6-difluorophenyl)-7-[(3S)-3-aminopyrrolidin-1-yl]-6-fluoro-1,4-dihydro-4-oxo-1,8-naphthyridine-3-carboxylic acid. The solution was concentrated in vacua. Ethanol was added to the residue. The precipitate was crushed, collected by filtration and washed with ethanol and then with diisopropyl ether to give 97 mg of the title compound.

Properties: pale brown powder mp: 246–250° C. (decomposed)

$^1$H-NMR (d$_6$-DMSO) δ: 2.09 (m, 1H), 2.22 (m, 1H), 7.03 (brt, 1H), 7.39 (t, J=10 Hz, 1H), 8.12 (d, J=12 Hz, 1H), 8.30 (brs, 2H), 8.72 (s, 1H)

EXAMPLE 51

1-(3-amino-2,4-difluorophenyl)-7-[(3S)-3-aminopyrrolidin-1-yl]-6-fluoro-4-oxo-1,4-dihydro-1,8-naphthyridine-3-carboxylic acid formic acid salt A mixture of 200 mg of 1-(3-amino-2,4-difluorophenyl)-7-[(3S)-3-aminopyrrolidin-1-yl]-6-fluoro-4-oxo-1,4-dihydro-1,8-naphthyridine-3-carboxylic acid and 200 mg of formic acid was stirred for about one minute, combined with 200 mg of ethanol and stirred at 90° C. for one minute. The solution was combined with 2 ml of ethanol, stirred at the same temperature for a further 2 minutes, and allowed to stand. The precipitate was collected by filtration and washed with ethanol and then with diisopropyl ether to give 154 mg of the title compound.

Properties: pale brown powder mp: 223–226° C.

$^1$H-NMR (d$_6$-DMSO) δ: 1.75 (m, 1H), 2.00 (m, 1H), 5.36 (s, 2H), 6.96 (t, J=8 Hz, 1H), 7.35 (t, J=11 Hz, 1H), 8.04 (d, J=12 Hz, 1H), 8.26 (s, 1H), 9.68 (s, 1H)

EXAMPLE 52

1-(3-amino-2,4-difluorophenyl)-7-[(3S)-3-aminopyrrolidin-1-yl]-6-fluoro-4-oxo-1,4-dihydro-1,8-naphthyridine-3-carboxylic acid p-toluenesulfonic acid salt To 300 mg of N,N-dimethylformamide were added 100 mg of 1-(3-amino-2,4-difluorophenyl)-7-[(3S)-3-aminopyrrolidin-1-yl]-6-fluoro-4-oxo-1,4-dihydro-1,8-naphthyridine-3-carboxylic acid and 55 mg of p-toluenesulfonic acid hydrate. The mixture was stirred for about 5 minutes. The homogenized solution was combined with 8 ml of diisopropyl ether, stirred, and allowed to stand. The supernatant was removed by decantation. The remainder was combined with 1 ml of ethanol, heated at reflux for 2 minutes, and allowed to cool down. The precipitate was collected by filtration and washed with ethanol and then with diisopropyl ether to give 120 mg of the title compound.

Properties: pale brown powder mp: 270° C.

$^1$H-NMR (d$_6$-DMSO) δ: 2.02 (m, 1H), 2.24 (m, 1H), 2.28 (s, 3H), 3.89 (m, 1H), 5.37 (brs, 2H), 6.96 (t, J=7 Hz, 1H), 7.11 (d, J=8 Hz, 2H), 7.35 (dt, J=2 Hz, 12 Hz, 1H), 7.47 (d, J=8 Hz, 2H), 7.95 (brs, 2H), 8.13 (d, J=12 Hz, 1H), 8.72 (s, 1H)

EXAMPLE 53

1-(3-amino-4,6-difluorophenyl)-6-fluoro-1,4-dihydro-7-(3-hydroxypyrrolidin-1-yl)-4-oxo-1,8-naphthyridine-3-carboxylic acid To 550 mg of N,N-dimethylformamide were added 150 mg of 1-(3-amino-4,6-difluorophenyl)-7-chloro-6-fluoro-4-oxo-1,4-dihydro-1,8-naphthyridine-3-carboxylic acid, 100 mg of 3-hydroxypyrrolidine, and 100 mg of triethylamine. The solution was stirred at 70° C. for 30 minutes. The reaction solution was combined with 8 ml of diisopropyl ether, stirred, and allowed to stand. The supernatant was removed by decantation. To the remainder was added 2 ml of ethanol. The precipitate was collected by filtration and washed with ethanol and then with diisopropyl ether to give 156 mg of the title compound.

Properties: colorless powder mp: 251–253° C.

$^1$H-NMR (d$_6$-DMSO) δ: 1.56 (m, 1H), 1.70–1.95 (m, 3H), 2.58–2.96 (m, 4H), 4.16 (m, 1H), 4.30 (brs, 1H), 5.35 (s, 2H), 6.95 (t, J=8 Hz, 1H), 7.36 (t, J=10 Hz, 1H), 8.01 (d, J=13 Hz, 1H), 8.59 (s, 1H)

EXAMPLE 54

1-(3-amino-4,6-difluorophenyl)-7-[(3S,4S)-3-amino-4-methylpyrrolidin-1-yl]-6-fluoro-1,4-dihydro-4-oxo-1,8-naphthyridine-3-carboxylic acid The title compound was obtained by the similar procedure as Example 48 except that (3S,4S)-3-amino-4-methylpyrrolidine dihydrochloride was used.

Properties: pale brown powder $^1$H-NMR (d$_6$-DMSO) δ: 0.93 (d, J=7 Hz, 3H), 2.17 (m, 1H), 5.35 (s, 2H), 6.97 (t, J=8 Hz, 1H), 7.36 (t, J=10 Hz, 1H), 7.99 (d, J=12 Hz, 1H), 8.65 (s, 1H)

EXAMPLE 55

1-(3-amino-4,6-difluorophenyl)-7-[(3R,4R)-3-amino-4-methylpyrrolidin-1-yl]-6-fluoro-1,4-dihydro-4-oxo-1,8-naphthyridine-3-carboxylic acid The title compound was obtained by the similar procedure as Example 48 except that (3R,4R)-3-amino-4-methylpyrrolidine dihydrochloride was used.

Properties: pale brown powder mp: 214–217° C.

$^1$H-NMR (d$_6$-DMSO) δ: 0.93 (d, J=7 Hz, 3H), 2.17 (m, 1H), 5.36 (s, 2H), 6.96 (t, J=8 Hz, 1H), 7.36 (t, J=10 Hz, 1H), 7.99 (d, J=12 Hz, 1H), 8.65 (s, 1H)

EXAMPLE 56

1-(3-amino-4,6-difluorophenyl)-7-[(3S,4R)-3-amino-4-methylpyrrolidin-1-yl]-6-fluoro-1,4-dihydro-4-oxo-1,8-naphthyridine-3-carboxylic acid The title compound was obtained by the similar procedure as Example 48 except that (3S,4R)-3-amino-4-methylpyrrolidine dihydrochloride was used.

Properties: pale brown powder
mp: 234–240° C.
$^1$H-NMR (d$_6$-DMSO) δ: 0.98 (d, J=7 Hz, 3H), 1.93 (m, 1H), 3.03 (m, 1H), 5.36 (s, 2H), 6.97 (t, J=8 Hz, 1H), 7.37 (t, J=10 Hz, 1H), 8.04 (d, J=12 Hz, 1H), 8.68 (s, 1H)

EXAMPLE 57

1-(3-amino-4,6-difluorophenyl)-7-[(3R,4S)-3-amino-4-methylpyrrolidin-1-yl]-6-fluoro-1,4-dihydro-4-oxo-1,8-naphthyridine-3-carboxylic acid The title compound was obtained by the similar procedure as Example 48 except that (3R,4S)-3-amino-4-methylpyrrolidine dihydrochloride was used.

Properties: pale brown powder
mp: 237–241° C.
$^1$H-NMR (d$_6$-DMSO) δ: 0.98 (d, J=6 Hz, 3H), 1.93 (m, 1H), 3.02 (m, 1H), 5.37 (s, 2H), 6.97 (t, J=8 Hz, 1H), 7.37 (t, J=10 Hz, 1H), 8.03 (d, J=13 Hz, 1H), 8.67 (s, 1H)

EXAMPLE 58

1-(3-amino-4,6-difluorophenyl)-7-(3-amino-4,4-dimethylpyrrolidin-1-yl)-6-fluoro-1,4-dihydro-4-oxo-1,8-naphthyridine-3-carboxylic acid The title compound was obtained by the similar procedure as Example 48 except that 3-amino-4,4-dimethylpyrrolidine dihydrochloride was used.

Properties: pale brown powder
mp: 267–269° C. (decomposed)
$^1$H-NMR (d$_6$-DMSO) δ: 0.86 (s, 3H), 0.95 (s, 3H), 2.88–3.05 (m, 1H), 5.36 (s, 2H), 6.97 (t, J=8 Hz, 1H), 7.38 (t, J=10 Hz, 1H), 8.02 (d, J=13 Hz, 1H), 8.66 (s, 1H)

EXAMPLE 59

1-(3-amino-4,6-difluorophenyl)-7-[3-(N-ethylaminomethyl)-pyrrolidin-1-yl]-6-fluoro-1,4-dihydro-4-oxo-1,8-naphthyridine-3-carboxylic acid The title compound was obtained by the similar procedure as Example 48 except that 3-(N-ethylaminomethyl)-pyrrolidine dihydrochloride was used.

Properties: pale brown powder
mp: 235–244° C. (decomposed)
$^1$H-NMR (d$_6$-DMSO) δ: 1.01 (t, J=7 Hz, 3H), 1.61 (m, 1H), 1.98 (m, 1H), 2.32 (m, 1H), 2.54 (q, J=7 Hz, 2H), 5.34 (s, 2H), 6.96 (t, J=8 Hz, 1H), 7.35 (t, J=10 Hz, 1H), 8.02 (d, J=12 Hz, 1H), 8.67 (s, 1H)

EXAMPLE 60

1-(3-amino-4,6-difluorophenyl)-7-[(3S)-3-aminopyrrolidin-1-yl]-6-fluoro-1,4-dihydro-4-oxoquinoline-3-carboxylic acid To 1 ml of dimethylsulfoxide were added 29 mg of 3S-(−)-aminopyrrolidine and 68 mg of triethylamine. The mixture was stirred for 10 minutes, 80 mg of 1-(3-amino-4,6-difluorophenyl)-6,7-difluoro-1,4-dihydro-4-oxoquinoline-3-carboxylic acid was added thereto, and the solution was heated and stirred at 100° C. for 2 hours. The reaction solution was allowed to cool down, diethyl ether was added thereto, and the supernatant was removed. Ethanol was added to the residue. The solid was collected by filtration and washed with diethyl ether to give 76 mg of the title compound.

Properties: colorless powder
mp: 213–221° C. (decomposed)
$^1$H-NMR (d$_6$-DMSO) δ: 1.62–1.76 (m, 1H), 1.88–2.06 (m, 1H), 3.08 (brs, 1H), 5.53 (s, 2H), 5.92 (d, J=8 Hz, 1H), 7.03 (t, J=8 Hz, 1H), 7.50 (t, J=11 Hz, 1H), 7.85 (d, J=14 Hz, 1H), 8.61 (s, 1H)

EXAMPLE 61

1-(3-amino-4,6-difluorophenyl)-7-[(3S,4S)-3-amino-4-methylpyrrolidin-1-yl]-6-fluoro-1,4-dihydro-4-oxoquinoline-3-carboxylic acid The title compound was obtained by the similar procedure as Example 60 except that (3S,4S)-3-amino-4-methylpyrrolidine was used.

Properties: brown powder
mp: 196–202° C.
$^1$H-NMR (d$_6$-DMSO) δ: 0.95 (d, J=7 Hz, 3H), 2.20 (brs, 1H), 5.53 (s, 2H), 5.88 (d, J=5 Hz, 1H), 7.02 (m, 1H), 7.50 (t, J=9 Hz, 1H), 7.85 (d, J=14 Hz, 1H), 8.60 (s, 1H)

EXAMPLE 62

1-(3-amino-4,6-difluorophenyl)-6-fluoro-1,4-dihydro-4-oxo-7-(pyrrolidin-1-yl)quinoline-3-carboxylic acid The title compound was obtained by the similar procedure as Example 60 except that pyrrolidine was used.

Properties: colorless powder
mp: 264–268° C. (decomposed)
$^1$H-NMR (d$_6$-DMSO) δ: 1.89 (brs, 4H), 5.52 (s, 2H), 5.97 (d, J=8 Hz, 1H), 7.03 (t, J=8 Hz, 1H), 7.49 (t, J=10 Hz, 1H), 7.85 (d, J=14 Hz, 1H), 8.62 (s, 1H)

EXAMPLE 63

1-(3-amino-4,6-difluorophenyl)-7-[(1S,6S)-2,8-diazabicyclo-[4.3.0]nona-8-yl]-6-fluoro-1,4-dihydro-4-oxoquinoline-3-carboxylic acid The title compound was obtained by the similar procedure as Example 60 except that (1S,6S)-2,8-diazabicyclo[4.3.0]nonane was used.

Properties: colorless powder
mp: 226–233° C. (decomposed)
$^1$H-NMR (d$_6$-DMSO) δ: 1.53–1.81 (m, 4H), 2.63 (brs, 1H) 2.88 (brs, 1H), 3.51 (m, 2H), 3.83 (brs, 2H), 5.57 (s, 2H), 5.97 (d, J=8 Hz, 1H), 7.05 (t, J=9 Hz, 1H), 7.51 (t, J=10 Hz, 1H), 7.92 (d, J=14 Hz, 1H), 8.65 (s, 1H)

EXAMPLE 64

1-(3-amino-4,6-difluorophenyl)-7-[(3S)-3-aminopyrrolidin-1-yl]-6,8-difluoro-1,4-dihydro-4-oxoquinoline-3-carboxylic acid The title compound was obtained by the similar procedure as Example 60 except that 1-(3-amino-4,6-difluorophenyl)-6,7,8-trifluoro-1,4-dihydro-4-oxoquinoline-3-carboxylic acid was used.

Properties: brown powder
mp: 204–210° C. (decomposed)
$^1$H-NMR (d$_6$-DMSO) δ: 1.67 (m, 1H), 1.95 (m, 1H), 5.42 (s, 2H), 7.08 (m, 1H), 7.37 (t, J=10 Hz, 1H), 7.78 (d, J=14 Hz, 1H), 8.45 (s, 1H)

EXAMPLE 65

1-(3-amino-4,6-difluorophenyl)-7-(3-hydroxypyrrolidin-1-yl)-6,8-difluoro-1,4-dihydro-4-oxoquinoline-3-carboxylic acid The title compound was obtained by the similar procedure as Example 60 except that 3-hydroxypyrrolidine was used.
Properties: pale yellow powder
mp: 144–152° C. (decomposed)
$^1$H-NMR (d$_6$-DMSO) δ: 1.81 (m, 2H), 3.79 (m, 1H), 4.29 (brs, 1H), 5.00 (s, 1H), 5.44 (s, 2H), 7.09 (t, J=8 Hz, 1H), 7.39 (t, J=10 Hz, 1H), 7.80 (d, J=14 Hz, 1H), 8.47 (s, 1H)

EXAMPLE 66

1-(3-amino-2,4-difluorophenyl)-7-[(3S)-3-aminopyrrolidin-1-yl)-6-fluoro-1,4-dihydro-4-oxo-1,8-naphthyridine-3-carboxylic acid The title compound was obtained by the similar procedure as Example 48 except that 1-(3-amino-2,4-difluorophenyl)-7-chloro-6-fluoro-1,4-dihydro-4-oxo-1,8-naphthyridine-3-carboxylic acid was used.
Properties: pale brown powder
mp: 268–272° C. (decomposed)
$^1$H-NMR (d$_6$-DMSO) δ: 1.79 (m, 1H), 2.05 (m, 1H), 5.58 (s, 2H), 6.84 (m, 1H), 7.11 (t, J=10 Hz, 1H), 8.07 (d, J=13 Hz, 1H), 8.69 (s, 1H)

EXAMPLE 67

1-(3-amino-2,4-difluorophenyl)-7-[(3S,4S)-3-amino-4-methylpyrrolidin-1-yl)-6-fluoro-1,4-dihydro-4-oxo-1,8-naphthyridine-3-carboxylic acid The title compound was obtained by the similar procedure as Example 48 except that 1-(3-amino-2,4-difluorophenyl)-7-chloro-6-fluoro-1,4-dihydro-4-oxo-1,8-naphthyridine-3-carboxylic acid was used.
Properties: pale brown powder
$^1$H-NMR (d$_6$-DMSO) δ: 0.91 (brd, 1H), 2.14 (m, 1H), 5.58 (s, 2H), 6.83 (m, 1H), 7.10 (t, J=10 Hz, 1H), 8.02 (d, J=12 Hz, 1H), 8.65 (s, 1H)

EXAMPLE 68

1-(3-amino-4,5,6-trifluorophenyl)-7-[(3S)-3-aminopyrrolidin-1-yl)-6-fluoro-1,4-dihydro-4-oxo-1,8-naphthyridine-3-carboxylic acid The title compound was obtained by the similar procedure as Example 60 except that 1-(3-amino-4,5,6-trifluorophenyl)-7-chloro-6-fluoro-1,4-dihydro-4-oxo-1,8-naphthyridine-3-carboxylic acid was used.
Properties: brown powder
mp: >256° C. (decomposed)
$^1$H-NMR (d$_6$-DMSO) δ: 1.58–1.84 (m, 1H), 1.84–2.23 (m, 1H), 5.74 (s, 2H), 6.81 (t, J=5 Hz, 1H), 8.03 (d, J=12 Hz, 1H), 8.73 (s, 1H)

EXAMPLE 69

1-(3-amino-4,5,6-trifluorophenyl)-7-[(3S)-3-aminopyrrolidin-1-yl)-6-fluoro-1,4-dihydro-4-oxoquinoline-3-carboxylic acid The title compound was obtained by the similar procedure as Example 60 except that 1-(3-amino-4,5,6-trifluorophenyl)-6,7-difluoro-1,4-dihydro-4-oxoquinoline-3-carboxylic acid was used.
Properties: brown powder
mp: >270° C. (decomposed)
$^1$H-NMR (d$_6$-DMSO) δ: 1.61–1.81 (m, 1H), 1.89–2.15 (m, 1H), 5.88 (s, 2H), 6.88 (brs, 1H), 7.85 (d, J=15 Hz, 1H), 8.69 (s, 1H)

EXAMPLE 70

1-(3-amino-2,4,6-trifluorophenyl)-7-[(3S)-3-aminopyrrolidin-1-yl)-6-fluoro-1,4-dihydro-4-oxo-1,8-naphthyridine-3-carboxylic acid In 1 ml of dimethylsulfoxide was dissolved 70 mg of 1-(3-amino-2,4,6-trifluorophenyl)-7-chloro-6-fluoro-1,4-dihydro-4-oxo-1,8-naphthyridine-3-carboxylic acid. To the solution were added 0.018 ml of 3(S)-3-aminopyrrolidine and 0.04 ml of triethylamine. The solution was stirred at 80° C. for 1 hour. Diethyl ether was added to the reaction solution to repeat decantation twice. A small amount of ethanol was added to the residue. After 10 minutes of refluxing, the precipitated solid was collected by filtration and washed with diethyl ether to give 51 mg of the title compound.
Properties: pale brown powder
mp: 273–277° C.
$^1$H-NMR (d$_6$-DMSO) δ: 1.75–1.78 (m, 1H), 2.00–2.18 (m, 1H), 5.46 (brs, 1H), 7.39 (t, J=10 Hz, 1H), 8.08 (d, J=13 Hz, 1H), 8.97 (s, 1H)

EXAMPLE 71

1-(3-amino-6-chloro-4-fluorophenyl)-7-[(3S)-3-aminopyrrolidin-1-yl]-6-fluoro-1,4-dihydro-4-oxo-1,8-naphthyridine-3-carboxylic acid The title compound was obtained by the similar procedure as Example 70 except that 1-(3-amino-6-chloro-4-fluorophenyl)-7-chloro-6-fluoro-1,4-dihydro-4-oxo-1,8-naphthyridine-3-carboxylic acid was used.
Properties: pale yellowish brown powder
mp: 249–252° C.
$^1$H-NMR (d$_6$-DMSO) δ: 1.74–1.95 (m, 1H), 2.00–2.16 (m, 1H), 5.69 (brs, 2H), 7.00 (d, J=9 Hz, 1H), 7.47 (d, J=11 Hz, 1H), 8.02 (d, J=12 Hz, 1H), 8.61 (s, 1H)

EXAMPLE 72

1-(3-amino-6-chloro-4-fluorophenyl)-7-[(3S)-3-aminopyrrolidin-1-yl]-6-fluoro-1,4-dihydro-4-oxoquinoline-3-carboxylic acid The title compound was obtained by the similar procedure as Example 70 except that 1-(3-amino-6-chloro-4-fluorophenyl)-7-chloro-6-fluoro-1,4-dihydro-4-oxoquinoline-3-carboxylic acid was used.
Properties: pale red powder
mp: 177–182° C. (decomposed)
$^1$H-NMR (d$_6$-DMSO) δ: 1.59–1.75 (m, 1H), 1.86–2.07 (m, 1H), 5.78 (d, J=7 Hz, 1H), 5.89 (brs, 2H), 7.06 (d, J=9 Hz, 1H), 7.60 (d, J=11 Hz, 1H), 7.86 (d, J=14 Hz, 1H), 8.56 (s, 1H)

EXAMPLE 73

1-(3-amino-4-chloro-6-fluorophenyl)-7-[(3S)-3-aminopyrrolidin-1-yl]-6-fluoro-1,4-dihydro-4-oxo-1,8-naphthyridine-3-carboxylic acid The title compound was obtained by the similar procedure as Example 70 except that 1-(3-amino-4-chloro-6- fluorophenyl)-7-chloro-6-fluoro-1,4-dihydro-4-oxo-1,8-naphthyridine-3-carboxylic acid was used.

Properties: brown powder mp: >258° C. (decomposed)

$^1$H-NMR (d$_6$-DMSO) δ: 1.53–1.80 (m, 1H), 1.83–2.06 (m, 1H), 5.56 (brs, 2H), 6.99 (d, J=7 Hz, 1H), 7.48 (d, J=10 Hz, 1H), 8.02 (d, J=13 Hz, 1H), 8.68 (s, 1H)

EXAMPLE 74

1-(3-amino-4-fluoro-2-methylphenyl)-7-[(3S)-3-aminopyrrolidin-1-yl]-6-fluoro-1,4-dihydro-4-oxo-1,8-naphthyridine-3-carboxylic acid The title compound was obtained by the similar procedure as Example 70 except that 1-(3-amino-4-fluoro-2-methylphenyl)-7-chloro-6-fluoro-1,4-dihydro-4-oxo-1,8-naphthyridine-3-carboxylic acid was used.

Properties: pale brown powder mp: >165° C. (decomposed)

$^1$H-NMR (d$_6$-DMSO) δ: 1.53–1.73 (m, 1H), 1.74–1.98 (m, 1H), 1.83 (s, 3H), 5.25 (br, 2H), 6.75 (d, J=9 Hz, 1H), 7.09 (d, J=13 Hz, 1H), 8.02 (d, J=13 Hz, 1H), 8.48 (s, 1H)

EXAMPLE 75

7-[(3S)-3-aminopyrrolidin-1-yl]-1-(2,4-difluoro-5-formylaminophenyl)-6-fluoro-1,4-dihydro-4-oxo-1,8-naphthyridine-3-carboxylic acid The title compound was obtained by the similar procedure as Example 48 except that 7-chloro-1-(2,4-difluoro-5-formylaminophenyl)-6-fluoro-1,4-dihydro-4-oxo-1,8-naphthyridine-3-carboxylic acid was used.

Properties: pale brown powder mp: 218–225° C.

$^1$H-NMR (d$_6$-DMSO) δ: 1.62 (m, 1H), 1.90 (m, 1H), 7.72 (t, J=10 Hz, 1H), 8.01 (d, J=13 Hz, 1H), 8.34 (s, 1H), 8.38 (t, J=8 Hz, 1H), 8.71 (s, 1H)

EXAMPLE 76

7-[(3S,4S)-3-amino-4-methylpyrrolidin-1-yl]-1-(2,4-difluoro-5-formylaminophenyl)-6-fluoro-1,4-dihydro-4-oxo-1,8-naphthyridine-3-carboxylic acid The title compound was obtained by the similar procedure as Example 54 except that 7-chloro-1-(2,4-difluoro-5-formylaminophenyl)-6-fluoro-1,4-dihydro-4-oxo-1,8-naphthyridine-3-carboxylic acid was used.

Properties: colorless powder mp: 215–216° C.

$^1$H-NMR (d$_6$-DMSO) δ: 0.92 (brd, 3H), 2.15 (m, 1H), 7.71 (t, J=10 Hz, 1H), 8.01 (d, J=12 Hz, 1H), 8.34 (s, 1H), 8.38 (t, J=8 Hz, 1H), 8.78 (s, 1H)

EXAMPLE 77

7-[(3S)-3-aminopyrrolidin-1-yl]-1-(3-benzoylamino-4,6-difluorophenyl)-6-fluoro-1,4-dihydro-4-oxo-1,8-naphthyridine-3-carboxylic acid The title compound was obtained by the similar procedure as Example 48 except that 1-(3-benzoylamino-4,6-difluorophenyl)-7-chloro-6-fluoro-1,4-dihydro-4-oxo-1,8-naphthyridine-3-carboxylic acid was used.

Properties: pale brown powder mp: 197–200° C.

$^1$H-NMR (d$_6$-DMSO) δ: 1.65 (m, 3H), 1.92 (m, 1H), 7.51–7.63 (m, 3H), 7.72 (t, J=10 Hz, 1H), 7.94–8.07 (m, 4H), 8.78 (s, 1H)

EXAMPLE 78

7-[(3S)-3-aminopyrrolidin-1-yl]-1-(2,4-difluoro-5-methylaminophenyl)-6-fluoro-1,4-dihydro-4-oxo-1,8-naphthyridine-3-carboxylic acid The title compound was obtained by the similar procedure as Example 48 except that 7-chloro-1-(2,4-difluoro-5-methylaminophenyl)-6-fluoro-1,4-dihydro-4-oxo-1,8-naphthyridine-3-carboxylic acid was used.

Properties: pale brown powder mp: 256–258° C. (decomposed)

$^1$H-NMR (d$_6$-DMSO) δ: 1.63 (m, 1H), 1.91 (m, 1H), 2.70 (d, J=5 Hz, 3H), 5.79 (brs, 1H), 6.96 (t, J=8 Hz, 1H), 7.39 (t, J=10 Hz, 1H), 8.02 (d, J=12 Hz, 1H), 8.68 (s, 1H)

EXAMPLE 79

7-[(3S)-3-aminopyrrolidin-1-yl]-1-(2,4-difluoro-5-methylaminophenyl)-6-fluoro-1,4-dihydro-4-oxoquinoline-3-carboxylic acid The title compound was obtained by the similar procedure as Example 60 except that 1-(2,4-difluoro-5-methylaminophenyl)-6,7-difluoro-1,4-dihydro-4-oxoquinoline-3-carboxylic acid was used.

Properties: brown powder mp: 219–226° C. (decomposed)

$^1$H-NMR (d$_6$-DMSO) δ: 1.59–1.78 (m, 1H), 1.91–2.07 (m, 1H), 2.70 (d, J=5 Hz, 3H), 5.91–6.04 (m, 1H), 7.04 (t, J=8 Hz, 1H), 7.54 (t, J=11 Hz, 1H), 7.86 (d, J=14 Hz, 1H), 8.63 (s, 1H)

EXAMPLE 80

7-[(3S)-3-aminopyrrolidin-1-yl]-1-(3-dimethylamino-4,6-difluorophenyl)-6-fluoro-1,4-dihydro-4-oxo-1,8-naphthyridine-3-carboxylic acid The title compound was obtained by the similar procedure as Example 48 except that 7-chloro-1-(3-dimethylamino-4,6-difluorophenyl)-6-fluoro-1,4-dihydro-4-oxo-1,8-naphthyridine-3-carboxylic acid was used.

Properties: pale brown powder mp: 248–251° C. (decomposed)

$^1$H-NMR (d$_6$-DMSO) δ: 1.63 (m, 1H), 1.91 (m, 1H), 2.77 (s, 6H), 7.36 (t, J=8 Hz, 1H), 7.49 (t, J=10 Hz, 1H), 8.02 (d, J=13 Hz, 1H), 8.74 (s, 1H)

EXAMPLE 81

7-[(3S)-3-aminopyrrolidin-1-yl]-1-[2,4-difluoro-5-(L-glycylamino)phenyl]-6-fluoro-1,4-dihydro-4-oxo-1,8-naphthyridine-3-carboxylic acid To 2 ml of N,N-dimethylformamide were added 700 mg of 1-(3-amino-4,6-difluorophenyl)-7-chloro-6-fluoro-4-oxo-1,4-dihydro-1,8-naphthyridine-3-carboxylic acid, 450 mg of (3S)-3-(t-butoxycarbonylamino)pyrrolidine, and 400 mg of triethylamine. The mixture was stirred at 70° C. for 30 minutes. To the solution was added 30 ml of diisopropyl ether. The solution was stirred and allowed to stand. The supernatant was decanted off. The remainder was ready for the subsequent reaction.

To 10 ml of dichloromethane were added 350 mg of N-Boc-glycine and 210 mg of N-methylmorpholine. With stirring at −20° C., 270 μl of isobutyl chloroformate was added to the solution, which was stirred for 20 minutes. This solution was cooled to −60° C., and the entire amount of the above-prepared 1-(3-amino-4,6-difluorophenyl)-7-[(3S)-3-(t-butoxycarbonylamino)pyrrolidinyl]-6-fluoro-4-oxo-1,4-dihydro-1,8-naphthyridine-3-carboxylic acid in 10 ml of dichloromethane was added thereto. The solution was allowed to slowly warm up to room temperature and then heated at reflux for 2 hours. The solution was allowed to stand at room temperature overnight and 50 ml of chloroform and 10 ml of distilled water were added thereto. The solution was separated, dried over anhydrous magnesium sulfate, and concentrated in vacua. A ⅓ fraction of the bubbly solidified residue was dissolved in 6 ml of acetonitrile, 1.5 ml of a dioxane solution of 4N hydrogen chloride was added thereto, and the solution was stirred at room temperature. A precipitate formed in about 1 minute. The solution as such was stirred overnight. The precipitate was collected by filtration and dissolved in about 4 ml of distilled water. The solution was neutralized to about pH 8 by adding a 10% sodium hydroxide aqueous solution little by little, causing a precipitate to form. The solution was heated at reflux for 1 hour and allowed to cool down. The precipitate was collected by filtration, and successively washed with distilled water, ethanol and diisopropyl ether to give 193 mg of the title compound in the form of a colorless powder.

Properties: colorless powder mp: >270° C.

$^1$H-NMR ($d_6$-DMSO) δ: 1.65 (m, 1H), 1.92 (m, 1H), 7.73 (t, J=11 Hz, 1H), 8.04 (d, J=13 Hz, 1H), 8.38 (m, 1H), 8.78 (s, 1H)

EXAMPLE 82

1-(3-amino-4,6-difluorophenyl)-6-fluoro-7-[(3S)-3-(L-valyl-amino)pyrrolidin-1-yl]-1,4-dihydro-4-oxo-1,8-naphthyridine-3-carboxylic acid To 5 ml of dichloromethane were added 220 mg of N-Boc-L-valine and 106 mg of N-methylmorpholine. With stirring at −20° C., 140 μl of isobutyl chloroformate was added to the solution, which was stirred for 20 minutes. This solution was cooled to −60° C., and a dispersion of 475 mg of ethyl 7-[(3S)-3-aminopyrrolidin-1-yl]-1-(2,4-difluoro-5-formylaminophenyl)- 6-fluoro-4-oxo-1,4-dihydro-1,8-naphthyridine-3-carboxylate in 10 ml of dichloromethane was added thereto. The solution was allowed to slowly warm up to room temperature and then stirred at 40° C. for 30 minutes. To the solution was added 20 ml of chloroform and 10 ml of distilled water. The solution was separated, dried over anhydrous magnesium sulfate, and concentrated in vacua. A half fraction of the bubbly solidified residue was dissolved in a mixture of 3 ml of 1N hydrochloric acid and 3 ml of ethanol, and the solution was stirred at 100° C. for 1.5 hours. The solution was concentrated in vacua, 3 ml of 1N hydrochloric acid was added to the residue, and the solution was stirred at 100° C. for 40 minutes. The solution was concentrated in vacua and the residue was dissolved in 2 ml of distilled water. The solution was neutralized to about pH 8 by adding a 10% sodium hydroxide aqueous solution little by little, causing a precipitate to form. With 2 ml of ethanol added, the solution was heated at reflux for 30 minutes and allowed to stand. The precipitate was collected by filtration, and washed with ethanol and then diisopropyl ether to give 141 mg of the title compound.

Properties: colorless powder mp: 162–167° C.

$^1$H-NMR ($d_6$-DMSO) δ: 0.78 (d, J=7 Hz, 3H), 0.80 (d, J=7 Hz, 3H), 1.71–1.92 (m, 2H), 1.95–2.10 (m, 1H), 2.88 (d, J=6 Hz, 1H), 4.32 (brs, 1H), 5.35 (s, 2H), 6.95 (t, J=8 Hz, 1H), 7.35 (t, J=10 Hz, 1H), 8.06 (d, J=12 Hz, 1H), 8.69 (s, 1H)

EXAMPLE 83

1-(3-amino-4,6-difluorophenyl)-6-fluoro-7-[(3S)-3-(L-valyl-amino)pyrrolidin-1-yl]-1,4-dihydro-4-oxo-1,8-naphthyridine-3-carboxylic acid monomethanesulfonic acid salt To 4 ml of ethanol were added 215 mg of 1-(3-amino-4,6-difluorophenyl)-6-fluoro-7-[(3S)-3-(L-valylamino)pyrrolidin- 1-yl]-1,4-dihydro-4-oxo-1,8-naphthyridine-3-carboxylic acid and 24 mg of methanesulfonic acid. The mixture was stirred and heated at reflux for 30 minutes. The solution was allowed to cool down and the precipitate was collected by filtration, washed with ethanol and then diisopropyl ether, and air dried to give 211 mg of the title compound.

Properties: colorless powder mp: >270° C.

$^1$H-NMR ($d_6$-DMSO) δ: 0.87 (d, J=7 Hz, 6H), 1.84–2.18 (m, 3H), 2.31 (s, 3H), 3.45 (brs, 1H), 4.36 (brs, 1H), 5.36 (s, 2H), 6.96 (t, J=8 Hz, 1H), 7.32 (m, 1H), 8.06 (brs, 2H), 8.09 (d, J=12 Hz, 1H), 8.64 (d, J=7 Hz, 1H), 8.71 (s, 1H)

EXAMPLE 84

1-(3-amino-4,6-difluorophenyl)-6-fluoro-7-[(3S)-3-(L-leucylamino)pyrrolidin-1-yl]-1,4-dihydro-4-oxo-1,8-naphthyridine-3-carboxylic acid The title compound was obtained by the similar procedure as in Example 82 except that N-Boc-L-leucine was used.

Properties: pale brown powder mp: 149–154° C.

$^1$H-NMR ($d_6$-DMSO) δ: 0.7 (d, J=7 Hz, 3H), 0.82 (d, J=7 Hz, 3H), 1.14–1.37 (m, 2H), 1.54–1.65 (m, 1H), 1.79–1.94 (m, 1H), 1.95–2.10 (m, 2H), 3.10 (t, J=7 Hz, 1H), 4.28 (brd, 1H), 5.35 (s, 2H), 6.96 (t, J=8 Hz, 1H), 7.34 (t, J=10 Hz, 1H), 8.05 (d, J=12 Hz, 1H), 8.69 (s, 1H)

EXAMPLE 85

1-(3-amino-4,6-difluorophenyl)-7-(3-methylaminopiperidino)-6-fluoro-1,4-dihydro-4-oxo-1,8-naphthyridine-3-carboxylic acid The title compound was obtained by the similar procedure as in Example 48 except that 3-methylaminopiperidine dihydrochloride was used.

Properties: pale brown powder mp: 240–242° C. (decomposed)

$^1$H-NMR ($d_6$-DMSO) δ: 1.23–1.46 (m, 2H), 1.62–1.87 (m, 2H), 2.11 (d, J=9 Hz, 3H), 3.82–4.18 (m, 2H), 5.36 (s, 2H), 6.98 (t, J=7 Hz, 1H), 7.39 (m, 1H), 8.09 (d, J=14 Hz, 1H), 8.71 (s, 1H)

EXAMPLE 86

1-(3-amino-4,6-difluorophenyl)-7-(3-methylaminopiperidin-1-yl)-6-fluoro-1,4-dihydro-4-oxoquinoline-3-carboxylic acid The title compound was obtained by the similar procedure as in Example 60 except that 3-methylaminopiperidine dihydrochloride was used.

Properties: colorless powder mp: 254–258° C. (decomposed)

$^1$H-NMR (d$_6$-DMSO) δ: 1.62 (m, 2H), 1.85 (m, 1H), 1.99 (m, 1H), 2.55 (s, 3H), 2.91 (m, 1H), 5.58 (s, 2H), 6.52 (d, J=7 Hz, 1H), 7.08 (t, J=8 Hz, 1H), 7.52 (t, J=10 Hz, 1H), 8.02 (d, J=13 Hz, 1H), 8.76 (s, 1H)

EXAMPLE 87

1-(3-amino-4,6-difluorophenyl)-7-piperazino-6-fluoro-1,4-dihydro-4-oxo-1,8-naphthyridine-3-carboxylic acid The title compound was obtained by the similar procedure as in Example 48 except that piperazine was used.

Properties: pale brown powder mp: 174–184° C. (decomposed)

$^1$H-NMR (d$_6$-DMSO) δ: 2.69 (m, 4H), 3.56 (m, 4H), 5.37 (s, 2H), 6.98 (t, J=7 Hz, 1H), 7.37 (t, J=10 Hz, 1H), 8.11 (d, J=13 Hz, 1H), 8.73 (s, 1H)

EXAMPLE 88

1-(3-amino-4,6-difluorophenyl)-7-(3,5-dimethylpiperazino)-6-fluoro-1,4-dihydro-4-oxo-1,8-naphthyridine-3-carboxylic acid The title compound was obtained by the similar procedure as in Example 48 except that piperazine was used.

Properties: pale brown powder mp: 251–256° C. (decomposed)

$^1$H-NMR (d$_6$-DMSO) δ: 0.96 (brs, 6H), 2.57–2.90 (m, 4H), 4.08 (m, 2H), 5.39 (brs, 2H), 6.98 (t, J=8 Hz, 1H), 7.41 (t, J=11 Hz, 1H), 8.16 (d, J=13 Hz, 1H), 8.78 (s, 1H)

EXAMPLE 89

1-(3-amino-4,6-difluorophenyl)-7-piperazino-6-fluoro-1,4-dihydro-4-oxoquinoline-3-carboxylic acid The title compound was obtained by the similar procedure as in Example 60 except that piperazine was used.

Properties: pale yellow powder mp: 192–200° C.

$^1$H-NMR (d$_6$-DMSO) δ: 3.14 (m, 4H), 3.25 (m, 4H), 5.58 (brs, 2H), 6.48 (d, J=7 Hz, 1H), 7.08 (t, J=8 Hz, 1H), 7.51 (t, J=10 Hz, 1H), 8.02 (d, J=13 Hz, 1H), 8.75 (s, 1H)

EXAMPLE 90

1-(3-amino-4,6-difluorophenyl)-7-(3-methylpiperazino)-6-fluoro-1,4-dihydro-4-oxoquinoline-3-carboxylic acid dihydrochloride To 1 ml of dimethylsulfoxide were added 35 mg of 3-methylpiperazine and 120 mg of triethylamine. After 10 minutes of stirring, 80 mg of 1-(3-amino-4,6-difluorophenyl)-6,7-difluoro-1,4-dihydro-4-oxoquinoline-3-carboxylic acid was added to the solution, which was heated and stirred at 100° C. for 2 hours. After the reaction solution was allowed to cool down, diethyl ether was added thereto and the supernatant was removed. Ethanol and hydrochloric acid were added to the residue and stirred at room temperature for 30 minutes. The solution was concentrated in vacua and diethyl ether was added to the residue. The solid was collected by filtration and washed with diethyl ether to give 30 mg of the title compound.

Properties: pale yellow powder mp: 206–213° C. (decomposed)

$^1$H-NMR (d$_6$-DMSO) δ: 1.26 (d, J=7 Hz, 3H), 2.85–3.02 (m, 1H), 6.51 (d, J=7 Hz, 1H), 7.08 (t, J=8 Hz, 1H), 7.52 (t, J=10 Hz, 1H), 8.04 (d, J=13 Hz, 1H), 8.76 (s, 1H)

EXAMPLE 91

1-(3-amino-4,6-difluorophenyl)-7-(3,5-dimethylpiperazino)-6-fluoro-1,4-dihydro-4-oxoquinoline-3-carboxylic acid The title compound was obtained by the similar procedure as in Example 60 except that 3,5-dimethylpiperazine was used.

Properties: colorless powder mp: 202–210° C. (decomposed)

$^1$H-NMR (d$_6$-DMSO) δ: 1.17 (brs, 6H), 2.74 (m, 1H), 3.54 (m, 2H), 5.57 (s, 2H), 6.50 (d, J=7 Hz, 1H), 7.08 (t, J=8 Hz, 1H), 7.52 (t, J=10 Hz, 1H), 8.02 (d, J=13 Hz, 1H), 8.75 (s, 1H)

EXAMPLE 92

1-(3-amino-6-chloro-4-fluorophenyl)-6-fluoro-7-piperazino-1,4-dihydro-4-oxo-1,8-naphthyridine-3-carboxylic acid In 8 ml of dimethylsulfoxide was dissolved 100 mg of 1-(3-amino-6-chloro-4-fluorophenyl)-7-chloro-6-fluoro-1,4-dihydro-4-oxo-1,8-naphythyridine-3-carboxylic acid. 120 mg of piperazine was added to the solution, which was stirred at 80° C. for 1.5 hours. Diethyl ether was added to the reaction solution to repeat decantation twice. A small amount of ethanol was added to the residue. After 10 minutes of refluxing, the precipitated solid was collected by filtration and washed with diethyl ether to give 19 mg of the title compound.

Properties: brown powder mp: 190° C. (decomposed)

$^1$H-NMR (d$_6$-DMSO) δ: 2.88 (s, 4H), 3.65 (s, 4H), 5.72 (s, 2H), 7.01 (d, J=5 Hz, 1H), 7.46 (d, J=11 Hz, 1H), 8.17 (d, J=13 Hz, 1H), 8.71 (s, 1H)

EXAMPLE 93

1-(3-amino-6-chloro-4-fluorophenyl)-6-fluoro-7-piperazino-1,4-dihydro-4-oxoquinoline-3-carboxylic acid The title compound was obtained by the similar procedure as in Example 92 except that 1-(3-amino-6-chloro-4-fluorophenyl)-7-chloro-6-fluoro-1,4-dihydro-4-oxoquinoline-3-carboxylic acid was used.

Properties: pale yellow powder mp: 228–237° C.

$^1$H-NMR (d$_6$-DMSO) δ: 2.81 (s, 4H), 5.91 (brs, 2H), 6.30 (d, J=7 Hz, 1H), 7.10 (d, J=10 Hz, 1H), 7.61 (d, J=11 Hz, 1H), 7.97 (d, J=12 Hz, 1H), 8.69 (s, 1H)

EXAMPLE 94

1-(3-amino-4-chloro-6-fluorophenyl)-6-fluoro-7-piperazino-1,4-dihydro-4-oxo-1,8-naphthyridine-3-carboxylic acid The title compound was obtained by the similar procedure as in Example 92 except that 1-(3-amino-4-chloro-6-fluorophenyl)-7-chloro-6-fluoro-1,4-dihydro-4-oxo-1,8-naphthyridine-3-carboxylic acid was used.

Properties: yellowish brown powder mp: 270° C.

$^1$H-NMR (d$_6$-DMSO) δ: 2.87 (brs, 4H), 5.59 (brs, 2H), 7.00 (d, J=7 Hz, 1H), 7.55 (d, J=10 Hz, 1H), 8.12 (d, J=13 Hz, 1H), 8.75 (s, 1H)

EXAMPLE 95

1-(3-amino-4-fluoro-6-methylphenyl)-6-fluoro-7-piperazino-1,4-dihydro-4-oxo-1,8-naphthyridine-3-carboxylic acid The title compound was obtained by the similar procedure as in Example 92 except that 1-(3-amino-4-fluoro-6-methylphenyl)-7-chloro-6-fluoro-1,4-dihydro-4-oxo-1,8-naphthyridine-3-carboxylic acid was used.

Properties: yellowish brown powder mp: 239° C. (decomposed)

$^1$H-NMR (d$_6$-DMSO) δ: 1.08 (s, 3H), 2.68 (brs, 4H), 3.48 (brs, 4H), 5.28 (brs, 2H), 6.77 (d, J=8 Hz, 1H), 7.09 (d, J=12 Hz, 1H), 8.11 (d, J=14 Hz, 1H), 8.55 (s, 1H)

EXAMPLE 96

1-(3-amino-2,4-difluorophenyl)-7-[(3S)-3-(formylamino)-pyrrolidin-1-yl]-6-fluoro-4-oxo-1,4-dihydro-1,8-naphthyridine-3-carboxylic acid To 600 mg of N,N-dimethylformamide were added 210 mg of 1-(3-amino-2,4-difluorophenyl)-7-[(3S)-3-aminopyrrolidin-1-yl]- 6-fluoro-4-oxo-1,4-dihydro-1,8-naphthyridine-3-carboxylic acid and 40 mg of formic acid. The solution was stirred at 120° C. for 1 hour. After 8 ml of diisopropyl ether was added and stirred, the solution was allowed to stand. The supernatant was decanted off. Then 2 ml of ethanol was added, and the solution was heated at reflux for 20 minutes and allowed to cool down. The precipitate was collected by filtration and washed with ethanol and then diisopropyl ether to give 180 mg of the title compound.

Properties: pale brown powder mp: 214–216° C.

$^1$H-NMR (d$_6$-DMSO) δ: 1.83 (m, 1H), 2.09 (m, 1H), 4.36 (m, 1H), 5.36 (s, 1H), 6.96 (t, J=8 Hz, 1H), 7.36 (t, J=10 Hz, 1H), 7.96 (d, J=4 Hz, 1H), 8.07 (d, J=13 Hz, 1H), 8.38 (m, 1H), 8.70 (s, 1H)

REFERENCE EXAMPLE 6

Ethyl 8-chloro-6,7-difluoro-1-(2,4-difluorophenyl)-1,4-dihydro-4-oxoquinoline-3-carboxylate To 3.9 g of ethyl ortho-formate and 5.5 g of acetic anhydride was added 5 g of ethyl 3-chloro-2,4,5-trifluorobenzoylacetate. The solution was heated at reflux for 3 hours, allowed to cool down, and concentrated in vacua. To the residue was added 20 ml of chloroform. With ice cooling, 2.3 ml of 2,4-difluoroaniline was added dropwise. After the completion of addition, the solution was stirred at room temperature for 2 hours. The reaction solution was concentrated in vacua, and hexane was added to the residue. The solid was collected by filtration to give ethyl 2-(3-chloro-2,4,5,6-tetrafluorobenzoyl)-3-(2,4-difluoroamino)acrylate. To 6.3 g of this ethyl 2-(3-chloro-2,4,5,6-tetrafluorobenzoyl)-3-(2,4-difluoroamino)acrylate were added 2.5 g of potassium carbonate and 20 ml of N,N-dimethylformamide. The solution was heated and stirred at 90° C. for 1 hour and allowed to cool down. The reaction solution was poured into ice water and the precipitate was collected by filtration and washed with water. The precipitate was dissolved in chloroform and washed with water. The solution was dried over magnesium sulfate and concentrated in vacua. Diethyl ether was added to the residue. The solid was collected by filtration and washed with ethanol and diethyl ether to give 5.1 g of the title compound.

Properties: colorless powder mp: 211–212° C.

$^1$H-NMR (CDCl$_3$) δ: 1.40 (t, J=7 Hz, 3H), 4.40 (q, J=7 Hz, 2H), 7.02–7.12 (m, 2H), 7.44 (m, 1H), 8.31–8.37 (m, 1H), 8.33 (s, 1H)

REFERENCE EXAMPLE 7

Ethyl 5,6,7,8-tetrafluoro-1-(2,4-difluorophenyl)-1,4-dihydro-4-oxoquinoline-3-carboxylate The title compound was obtained by the similar procedure as in Reference Example 6 except that ethyl 2,3,4,5,6-pentafluorobenzoylacetate was used.

Properties: colorless powder mp: 172–173° C.

$^1$H-NMR (CDCl$_3$) δ: 1.38 (t, J=7 Hz, 3H), 4.37 (q, J=7 Hz, 2H), 7.08 (m, 2H), 7.50 (m, 1H), 8.18 (s, 1H)

REFERENCE EXAMPLE 8

N-Ethoxycarbonyl-2,4-difluoro-m-phenylenediamine methane-sulfonic acid salt

To 500 ml of conc. sulfuric acid was added 151 g of 2,4-difluorobenzoic acid. With ice cooling and stirring, 114 g of potassium nitrate powder was added thereto in portions over 30 minutes. Stirring was continued for a further 1 hour, yielding a sherbet-like precipitate. The reaction solution was poured into 1.5 L of ice water and stirred for 30 minutes. The precipitate was collected by filtration, washed with 1 L of distilled water, air dried, and then dried in vacua over phosphorus pentoxide to give 164.5 g of 2,4-difluoro-5-nitrobenzoic acid as colorless crystals.

To 20 ml of dichloromethane was added 6.1 g of 2,4-difluoro-5-nitrobenzoic acid. With 3 ml of oxalyl chloride and 4 drops of N,N-dimethylformamide added, the solution was stirred for 2 hours. The solvent and the excess of the reagents were distilled off in vacua. The residue was dissolved in 6 ml of dichloromethane and then added dropwise to a solution of 2.1 g of sodium azide in 5 ml of N,N-dimethylformamide while ice cooling and stirring. The mixture was stirred for 10 minutes, then warmed to room temperature, stirred for a further 5 minutes, combined with 45 ml of ethyl ether, 15 ml of n-hexane and 100 ml of distilled water. After shaking, the mixture was separated into layers. The organic layer was washed with 100 ml of distilled water, dried over anhydrous magnesium sulfate, and concentrated in vacua. A ⅔ fraction of the residue was combined with 6 ml of ethanol and heated in a hot water bath at 80° C. for 2 hours to give an ethanol solution of crude N-ethoxycarbonyl-2,4-difluoro-5-nitroaniline.

To the solution was added 14 ml of ethanol. With 2.0 g of methanesulfonic acid and 0.2 g of 10% palladium on carbon added, hydrogenation was carried out overnight (15 hours) at room temperature. Since a precipitate formed, 20 ml of methanol was added to dissolve the precipitate. The catalyst was filtered off. The filtrate was concentrated in vacua, and the precipitated plates were collected by filtration and washed with a mixture of ethanol and diisopropyl ether to give 4.0 g of the title compound as slightly red crystals.

REFERENCE EXAMPLE 9

N-benzyloxycarbonyl-2,4-difluoro-m-phenylenediamine

To 60 ml of dichloromethane was added 20.3 g of 2,4-difluoro-5-nitrobenzoic acid. With 10 ml of oxalyl chloride and 15 drops of N,N-dimethylformamide added, the solution was stirred overnight. The solvent and the excess of the reagents were distilled off in vacua. The residue was dissolved in 30 ml of dichloromethane and then added to 15 ml of N,N-dimethylformamide. While ice cooling and stirring, 7.5 g of sodium azide was added in portions to the solution. The mixture was stirred for 10 minutes, then warmed to room temperature, stirred for a further 10 minutes, and combined with 100 ml of ethyl ether, 50 ml of n-hexane and 400 ml of distilled water. After shaking, the mixture was separated into layers. The organic layer was washed twice with 400 ml of distilled water, dried over anhydrous magnesium sulfate, and concentrated in vacua. To the residue was added 12.0 g of benzyl alcohol. The solution was concentrated in vacua, and 150 ml of toluene was added to the residue. After the solution was heated in a warm water bath at 40° C. for 2 hours, then in a hot water bath at 60° C. for 25 hours, and then in a hot water bath at 100° C. for 1 hour, it was concentrated in vacua to give crude N-benzyloxycarbonyl-2,4-difluoro-5-nitroaniline as a slowly solidifying residue.

To a mixture of 300 ml of distilled water and 200 ml of ethanol was added 84 g of iron powder. With stirring at 80° C., 7 ml of conc. hydrochloric acid was added to the solution in portions, and stirring was continued for 5 minutes. The entire amount of the above-prepared N-benzyloxycarbonyl-2,4-difluoro-5-nitroaniline was dissolved in 100 ml of ethanol and added to the dispersion in portions such that mild reflux might occur. The dispersion was stirred at 80° C. for 15 minutes. After 500 ml of benzene was added, stirring was continued for 5 minutes. After the iron powder was filtered off, the filtrate was washed with ethanol, combined with 200 ml of distilled water, and shaken for separation. The organic layer was dried over anhydrous magnesium sulfate, passed through a thin layer of silica gel powder, and concentrated in vacua. The precipitated colorless plates were dispersed in diisopropyl ether and collected by filtration to give 18.2 g of the title compound.

EXAMPLE 97

Ethyl 8-chloro-6,7-difluoro-1-(2,4-difluoro-5-nitrophenyl)-1,4-dihydro-4-oxoquinoline-3-carboxylate To 15 ml of sulfuric acid was added 2.5 g of ethyl 8-chloro-6,7-difluoro-1-(2,4-difluorophenyl)-1,4-dihydro-4-oxoquinoline-3-carboxylate. With ice cooling, 950 mg of potassium nitrate was added in portions and the solution was stirred overnight at room temperature. The reaction solution was poured into ice water and stirred overnight at room temperature. The precipitate was collected by filtration and washed with water, ethanol and diethyl ether to give 2.4 g of the title compound.

Properties: colorless powder mp: 209–210+ C.

$^1$H-NMR (CDCl$_3$) δ: 1.40 (t, J=7 Hz, 3H), 4.40 (q, J=7 Hz, 2H), 7.43 (t, J=9 Hz, 1H), 8.30 (s, 1H), 8.36 (m, 2H)

EXAMPLE 98

Ethyl 8-chloro-6,7-difluoro-1-(2,4-difluoro-5-formylaminophenyl)-1,4-dihydro-4-oxoquinoline-3-carboxylate To 20 ml of dichloroethane and 10 ml of formic acid were added 2 g of ethyl 8-chloro-6,7-difluoro-1-(2,4-difluoro-5-nitrophenyl)-1,4-dihydro-4-oxoquinoline-3-carboxylate and 200 mg of 10% palladium on carbon. Under a hydrogen atmosphere, the solution was stirred at room temperature for 3 hours and after addition of acetic anhydride, further stirred overnight. The catalyst was removed by a membrane filter and the filtrate was concentrated in vacua. Diethyl ether was added to the residue whereupon the solid was collected by filtration and washed with ethanol and diethyl ether to give 1.9 g of the title compound.

Properties: yellow powder mp: 223–229° C.

$^1$H-NMR (d$_6$-DMSO) δ: 1.27 (t, J=7 Hz, 3H), 4.23 (q, J=7 Hz, 2H), 7.76 (t, J=10 Hz, 1H), 8.23 (t, J=10 Hz, 1H), 8.33 (s, 1H), 8.47–8.60 (m, 1H), 8.51 (s, 1H)

EXAMPLE 99

1-(3-amino-4,6-difluorophenyl)-8-chloro-6,7-difluoro-1,4-dihydro-4-oxoquinoline-3-carboxylic acid Ethyl 8-chloro-6,7-difluoro-1-(2,4-difluoro-5-formylaminophenyl)-1,4-dihydro-4-oxoquinoline-3-carboxylate (1.8 g) was added to 5 ml of hydrochloric acid and 20 ml of acetic acid. The solution was heated at reflux for 3 hours. The reaction solution was allowed to cool down and concentrated in vacua, and ethanol was added to the residue. The solid was collected by filtration and washed with diethyl ether to give 1.4 g of the title compound.

Properties: pale yellow powder mp: 225–226.5° C.

$^1$H-NMR (d$_6$-DMSO) δ: 7.09 (t, J=8 Hz, 1H), 7.43 (t, J=11 Hz, 1H), 8.40 (t, J=9 Hz, 1H), 8.69 (s, 1H)

EXAMPLE 100

Ethyl 5-benzyloxy-1-(3-ethoxycarbonylamino-4,6-difluorophenyl)-6,7-difluoro-1,4-dihydro-4-oxoquinoline-3-carboxylate Ethyl 2-benzyloxy-3,4,6-trifluorobenzoylacetate (1.35 g) was added to 860 mg of ethyl ortho-formate and 1.2 g of acetic anhydride and the solution was heated and stirred for 4 hours. The reaction solution was allowed to cool down and concentrated in vacua. To the residue was added 20 ml of chloroform. With ice cooling, a solution of 1.2 g of N-ethoxycarbonyl-2,4-difluoro-m-phenylenediamine methansulfonate of Reference Example 8 and 0.51 ml of triethylamine in 20 ml of methanol was added dropwise. After the completion of addition, the solution was stirred at room temperature for 2 hours. The reaction solution was concentrated in vacua. To the residue were added 630 mg of potassium carbonate and 5 ml of N,N-dimethylformamide. The solution was heated and stirred at 90° C. for 1 hour. The reaction solution was allowed to cool down and poured into ice water. The precipitated solid was collected by filtration and dissolved in chloroform. The organic layer was separated and dried over magnesium sulfate, and the solvent was distilled off. Ethanol and diethyl ether were added to the residue. The solid was collected by filtration and washed with diethyl ether to give 1.2 g of the title compound.

Properties: yellow powder mp: 130–134° C.

$^1$H-NMR (CDCl$_3$) δ: 1.33 (t, J=7 Hz, 3H), 1.38 (t, J=7 Hz, 3H), 4.26 (q, J=7 Hz, 2H), 4.38 (q, J=7 Hz, 2H), 5.32 (s, 2H), 6.41 (m, 1H), 6.97 (d, J=3 Hz, 1H), 7.19 (dd, J=9 Hz, 10 Hz, 1H), 7.26–7.42 (m, 3H), 7.64 (m, 2H), 8.25 (s, 1H), 8.38 (t, J=8 Hz, 1H)

EXAMPLE 101

1-(3-amino-4,6-difluorophenyl)-6,7-difluoro-5-hydroxy-1,4-dihydro-4-oxoquinoline-3-carboxylic acid Ethyl 5-benzyloxy-1-(3-ethoxycarbonylamino-4,6-difluorophenyl)-6,7-difluoro-1,4-dihydro-4-oxoquinoline-3-carboxylate (500 mg) was added to 5 ml of 48% hydrobromic acid and 5 ml of acetic acid. The solution was heated at reflux overnight. The reaction solution was allowed to cool down and concentrated in vacua, and ethanol was added to the residue. The solid was collected by filtration and washed with diethyl ether to give 130 mg of the title compound.

Properties: pale yellow powder mp: >270° C.

$^1$H-NMR (d$_6$-DMSO) δ: 6.64 (dd, J=6 Hz, 12 Hz, 1H), 6.99 (dd, J=8 Hz, 9 Hz, 1H), 7.49 (dd, J=10 Hz, 11 Hz, 1H), 8.77 (s, 1H)

EXAMPLE 102

Ethyl 1-(3-benzyloxycarbonylamino-4,6-difluorophenyl)-6,7-difluoro-5-methyl-1,4-dihydro-4-oxoquinoline-3-carboxylate Ethyl 2-methyl-3,4,6-trifluorobenzoylacetate (2.6 g) was added to 2.2 mg of ethyl ortho-formate and 3.1 g of acetic anhydride and the solution was heated and stirred for 2 hours. The reaction solution was allowed to cool down and concentrated in vacua. To the residue was added 20 ml of chloroform. With ice cooling, a solution of 2.78 g of N-benzyloxycarbonyl-2,4-difluoro-m-phenylenediamine of Reference Example 9 in 10 ml of chloroform was added dropwise. After the completion of addition, the solution was stirred at room temperature for 1 hour. The reaction solution was concentrated in vacua. To the residue were added 1.65 g of potassium carbonate-and 10 ml of N,N-dimethylformamide. The solution was heated and stirred at 90° C. for 1 hour. The reaction solution was allowed to cool down and poured into ice water. The precipitated solid was collected by filtration and dissolved in chloroform. The organic layer was separated and dried over magnesium sulfate, and the solvent was distilled off. Ethanol and diethyl ether were added to the residue. The solid was collected by filtration and washed with diethyl ether to give 2.4 g of the title compound.

Properties: yellow powder mp: 202–204° C.

$^1$H-NMR (CDCl$_3$) δ: 1.38 (t, J=7 Hz, 3H), 2.92 (d, J=3 Hz, 3H), 4.38 (q, J=7 Hz, 2H), 5.21 (s, 2H), 6.50 (t, J=9 Hz, 1H), 7.08 (brs, 1H), 7.19 (t, J=10 Hz, 1H), 7.39 (brs, 5H), 8.27 (s, 1H), 8.38 (t, J=8 Hz, 1H)

EXAMPLE 103

1-(3-amino-4,6-difluorophenyl)-6,7-difluoro-5-methyl-1,4-dihydro-4-oxoquinoline-3-carboxylic acid Ethyl 1-[3-(benzyloxycarbonylamino-4,6-difluorophenyl)]-6,7-difluoro-5-methyl-1,4-dihydro-4-oxoquinoline-3-carboxylate (2 g) was added to 10 ml of hydrochloric acid and 20 ml of acetic acid. The solution was heated at reflux for 3 hours. The solution was allowed to cool down and concentrated in vacua. Ethanol was added to the residue. The solid was collected by filtration and washed with diethyl ether to give 940 mg of the title compound.

Properties: colorless powder mp: >270° C.

$^1$H-NMR (d$_6$-DMSO) δ: 2.86 (brs, 3H), 7.07 (t, J=8 Hz, 1H), 7.20 (m, 1H), 7.52 (t, J=11 Hz, 1H), 8.81 (s, 1H)

EXAMPLE 104

Ethyl 5,6,7,8-tetrafluoro-1-(2,4-difluoro-5-nitrophenyl)-1,4-dihydro-4-oxoquinoline-3-carboxylate The title compound was obtained by the similar procedure as Example 97 except that ethyl 5,6,7,8-tetrafluoro-1-(2,4-difluorophenyl)-1,4-dihydro-4-oxoquinoline-3-carboxylate was used.

Properties: colorless powder mp: 235–238° C.

$^1$H-NMR (d$_6$-DMSO) δ: 1.26 (t, J=7 Hz, 3H), 4.23 (q, J=7 Hz, 2H), 8.15 (t, J=10 Hz, 1H), 8.54 (s, 1H), 8.95 (t, J=8 Hz, 1H)

EXAMPLE 105

Ethyl 5,6,7,8-tetrafluoro-1-(2,4-difluoro-5-formylaminophenyl)-1,4-dihydro-4-oxoquinoline-3-carboxylate The title compound was obtained by the similar procedure as Example 98 except that ethyl 5,6,7,8-tetrafluoro-1-(2,4-difluoro-5-nitrophenyl)-1,4-dihydro-4-oxoquinoline-3-carboxylate was used.

Properties: pale brown powder mp: 179–182° C.

$^1$H-NMR (d$_6$-DMSO) δ: 1.25 (t, J=7 Hz, 3H), 4.22 (q, J=7 Hz, 2H), 7.78 (t, J=10 Hz, 1H), 8.34 (s, 1H), 8.44 (s, 1H), 8.55 (t, J=8 Hz, 1H)

EXAMPLE 106

Ethyl 5-benzylamino-6,7,8-trifluoro-1-(2,4-difluoro-5-formylaminophenyl)-1,4-dihydro-4-oxoquinoline-3-carboxylate To 30 ml of toluene were added 800 mg of ethyl 5,6,7,8-tetrafluoro-1-(2,4-difluoro-5-formylaminophenyl)-1,4-dihydro-4-oxoquinoline-3-carboxylate, 0.21 ml of benzylamine, and 240 mg of anhydrous potassium carbonate. The solution was heated at reflux overnight. The reaction solution was allowed to cool down and concentrated in vacua. The residue was combined with chloroform and washed with water. The solution was dried over magnesium sulfate and the solvent was distilled off. Diethyl ether was added to the residue. The solid was collected by filtration and washed with diethyl ether to give 600 mg of the title compound.

Properties: yellow powder mp: 151–156° C.

$^1$H-NMR (d$_6$-DMSO) δ: 1.24 (t, J=7 Hz, 3H), 4.19 (q, J=7 Hz, 2H), 4.66 (m, 2H), 7.29 (m, 2H), 7.36 (s, 3H), 7.73 (t, J=11 Hz, 1H), 8.33 (s, 2H), 8.50 (t, J=8 Hz, 1H)

EXAMPLE 107

Ethyl 5-amino-6,7,8-trifluoro-1-(2,4-difluoro-5-formylaminophenyl)-1,4-dihydro-4-oxoquinoline-3-carboxylate To 20 ml of ethanol and 10 ml of acetic acid were added 600 mg of ethyl 5-benzylamino-6,7,8-trifluoro-1-(2,4- difluoro-5-formylaminophenyl)-1,4-dihydro-4-oxoquinoline-3-carboxylate and 100 mg of 10% palladium on carbon. Under a hydrogen atmosphere, the solution was stirred at room temperature for 2 days. The catalyst was removed by a membrane filter and the filtrate was concentrated in vacua. Diethyl ether was added to the residue whereupon the solid was collected by filtration and washed with diethyl ether to give 420 mg of the title compound.

Properties: yellow powder mp: >230° C. (decomposed)

$^1$H-NMR (d$_6$-DMSO) δ: 1.25 (t, J=7 Hz, 3H), 4.20 (q, J=7 Hz, 2H), 7.73 (t, J=11 Hz, 1H), 7.88 (brs, 2H), 8.30 (s, 1H), 8.34 (s, 1H), 8.49 (t, J=8 Hz, 1H)

EXAMPLE 108

5-amino-1-(3-amino-4,6-difluorophenyl)-6,7,8-trifluoro-1,4-dihydro-4-oxoquinoline-3-carboxylic acid The title compound was obtained by the similar procedure as Example 99 except that ethyl 5-amino-6,7,8-trifluoro-1-(2,4-difluoro-5-formylaminophenyl)-1,4-dihydro-4-oxoquinoline-3-carboxylate was used.

Properties: yellow powder mp: >270° C.

$^1$H-NMR (d$_6$-DMSO) δ: 7.14 (t, J=8 Hz, 1H), 7.42 (t, J=10 Hz, 1H), 8.50 (s, 1H)

EXAMPLE 109

Ethyl 1-(3-benzyloxycarbonylamino-4,6-difluorophenyl)-7-chloro-1,4-dihydro-4-oxo-1,8-naphthyridine-3-carboxylate Ethyl 2,6-dichloronicotinoylacetate (11.8 g) was added to 8.8 ml of ethyl ortho-formate and 13 ml of acetic anhydride and the solution was heated at reflux for 2 hours. The reaction solution was concentrated in vacua. To 3.2 g of this compound was added 20 ml of toluene. A solution of 3.1 g of N-benzyloxycarbonyl-2,4-difluoro-m-phenylenediamine of Reference Example 9 in 10 ml of toluene and 10 ml of ethanol was added dropwise. After the completion of addition, the solution was stirred at room temperature overnight. The reaction solution was concentrated in vacua to give ethyl 2-(2,6-dichloronicotinoyl)-3-(3-benzyloxycarbonylamino-4,6-difluorophenylamino)acrylate. Its entire amount was dissolved in 10 ml of N,N-dimethylformamide and 1.39 g of potassium carbonate was added. The solution was stirred at room temperature overnight. The reaction solution was poured into ice water. The solid was collected by filtration and washed with ethanol and then diethyl ether to give 3.4 grams of the title compound.

Properties: colorless powder mp: 242–243° C.

$^1$H-NMR (CDCl$_3$) δ: 1.41 (t, J=7 Hz, 3H), 4.41 (q, J=7 Hz, 2H), 5.22 (s, 2H), 7.01 (brs, 1H), 7.13 (t, J=9 Hz, 1H), 7.37 (s, 2H), 7.40 (s, 3H), 7.50 (m, 1H), 8.35 (m, 1H), 8.54 (s, 1H), 8.72 (d, J=8 Hz, 1H)

EXAMPLE 110

1-(3-amino-4,6-difluorophenyl)-7-chloro-1,4-dihydro-4-oxo-1,8-naphthyridine-3-carboxylic acid To 1.0 g of ethyl 1-(3-benzyloxycarbonylamino-4,6-difluorophenyl)-7-chloro-1,4-dihydro-4-oxo-1,8-naphthyridine-3-carboxylate were added 4 ml of 12N hydrochloric acid and 8 ml of acetic acid. The solution was heated at reflux for 3 hours and stirred at room temperature overnight. The solid precipitated in the reaction solution was collected by filtration and successively washed with ethanol, chloroform and diethyl ether to give 550 mg of the title compound.

Properties: colorless powder mp: >270° C.

$^1$H-NMR (d$_6$-DMSO) δ: 7.07 (t, J=8 Hz, 1H), 7.44 (t, J=10 Hz, 1H), 7.80 (d, J=8 Hz, 1H), 8.78 (d, J=8 Hz, 1H) 8.96 (s, 1H)

EXAMPLE 111

7-chloro-6-fluoro-1-(4-fluoro-3-nitrophenyl)-1,4-dihydro-4-oxo-1,8-naphthyridine-3-carboxylic acid To 10 ml of conc. sulfuric acid was added 1.5 g of 7-chloro-6-fluoro-1-(4-fluorophenyl)-1,4-dihydro-4-oxo-1,8-naphthyridine-3-carboxylic acid. Potassium nitrate (1.4 g) was added in portions to the solution, which was heated and stirred at 80° C. for 2 hours. The reaction solution was allowed to cool down, poured into ice water, and stirred overnight. The precipitated solid was collected by filtration and successively washed with water, ethanol, and diethyl ether to give 1.1 grams of the title compound.

Properties: pale yellow powder mp: >270° C.

$^1$H-NMR (d$_6$-DMSO) δ: 7.89 (t, J=10 Hz, 1H), 8.09–8.17 (m, 1H), 8.59–8.66 (m, 1H), 8.80 (d, J=7 Hz, 1H) 9.08 (s, 1H)

EXAMPLE 112

Methyl 7-chloro-6-fluoro-1-(4-fluoro-3-nitrophenyl)-1,4-dihydro-4-oxo-1,8-naphthyridine-3-carboxylate To 25 ml of methanol was added dropwise 1 g of thionyl chloride. To the solution was added 1.1 g of 7-chloro-6-fluoro-1-(4-fluoro-3-nitrophenyl)-1,4-dihydro-4-oxo-1,8-naphthyridine-3-carboxylic acid. The solution was heated at reflux overnight. The reaction solution was allowed to cool down and concentrated in vacua. Diethyl ether was added to the residue. The solid was collected by filtration to give 1.4 g of the title compound.

Properties: yellow powder mp: 207–212° C.

$^1$H-NMR (d$_6$-DMSO) δ: 3.78 (s, 3H), 7.87 (d, J=9 Hz, 1H), 8.10–8.17 (m, 1H), 8.54–8.62 (m, 2H), 8.78 (s, 1H)

EXAMPLE 113

1-(3-amino-4-fluorophenyl)-7-chloro-6-fluoro-1,4-dihydro-4-oxo-1,8-naphthyridine-3-carboxylic acid Methyl 7-chloro-6-fluoro-1-(4-fluoro-3-nitrophenyl)-1,4-dihydro-4-oxo-1,8-naphthyridine-3-carboxylate (600 mg) was dissolved in 30 ml of methanol, 10 ml of acetic acid and 30 ml of dichloroethane, and 100 mg of 10% palladium on carbon was added thereto. Under a hydrogen atmosphere, the solution was stirred at room temperature overnight. The catalyst was removed by a membrane filter and the filtrate was concentrated in vacua. To the residue were added 4 ml of acetic acid and 1 ml of hydrochloric acid. The solution was heated and stirred at 100° C. overnight. The reaction solution was concentrated in vacua. Diethyl ether was added to the residue whereupon the solid was collected by filtration and washed with diethyl ether to give 160 mg of the title compound.

Properties: pale yellow powder mp: >270° C.

$^1$H-NMR (d$_6$-DMSO) δ: 6.74–6.83 (m, 1H), 6.96 (dd, J=3 Hz, 8 Hz, 1H), 7.23 (dd, J=9 Hz, 11 Hz, 1H), 8.76 (t, J=8 Hz, 1H), 8.79 (s, 1H)

EXAMPLE 114

Ethyl 7-chloro-1-(3-ethoxycarbonylamino-4,6-difluorophenyl)-6-fluoro-4-oxo-1,4-dihydro-1,8-naphthyridine-3-carboxylate Ethyl 3-ethoxy-2-(2',6'-dichloro-5'-fluoronicotinoyl)-acrylate prepared from 1.25 g of ethyl 2,6-dichloro-5-fluoronicotinoylacetate by a conventional process was dissolved in 10 ml of methanol. To the methanol solution, 1.30 g of N-ethoxycarbonyl-2,4-difluoro-m-phenylenediamine methansulfonate of Reference Example 8 was added together with 500 mg of triethylamine. The reaction solution was concentrated in vacua. To the residue were added 50 ml of chloroform and 50 ml of distilled water. After shaking, the mixture was separated into layers. The organic layer was dried over anhydrous magnesium sulfate and concentrated in vacua. To the residue were added 2.1 g of anhydrous potassium carbonate and 4 ml of N,N-dimethylformamide. The solution was heated and stirred at 90° C. for 15 minutes. The reaction solution was allowed to cool down and 50 ml of chloroform and 300 ml of distilled water were added, followed by separation. The chloroform layer was washed twice with 300 ml of distilled water, dried over anhydrous magnesium sulfate, and concentrated in vacua. The precipitate was dispersed in ethanol, collected by filtration and washed with ethanol and then diisopropyl ether to give 647 mg of the title compound.

Properties: pale brown powder mp: 209–212° C.

$^1$H-NMR (d$_6$-DMSO) δ: 1.24 (t, J=7 Hz, 3H), 1.28 (t, J=7 Hz, 3H), 4.13 (q, J=7 Hz, 2H), 4.24 (q, J=7 Hz, 2H), 7.70 (t, J=10 Hz, 1H), 8.03 (t, J=8 Hz, 1H), 8.54 (d, J=8 Hz, 1H), 8.76 (s, 1H)

EXAMPLE 115

7-chloro-1-(3-ethoxycarbonylamino-4,6-difluorophenyl)-6-fluoro-4-oxo-1,4-dihydro-1,8-naphthyridine-3-carboxylic acid Ethyl 7-chloro-1-(3-ethoxycarbonylamino-4,6-difluorophenyl)-6-fluoro-4-oxo-1,4-dihydro-1,8-naphthyridine-3-carboxylate (200 mg) was added to a mixture of 1.5 ml of 3N hydrochloric acid and 1 ml of acetic acid. The solution was heated at reflux for 3 hours and 40 minutes. The reaction solution was allowed to cool down whereupon the precipitate was collected by filtration and washed with ethanol and then diisopropyl ether to give 149 mg of the title compound.

Properties: pale yellow powder mp: 233–235° C.

$^1$H-NMR (d$_6$-DMSO) δ: 1.24 (t, J=7 Hz, 3H), 4.13 (q, J=7 Hz, 2H), 7.71 (t, J=10 Hz, 1H), 8.08 (t, J=8 Hz, 1H), 8.77 (d, J=7 Hz, 1H), 9.06 (s, 1H) 9.65 (s, 1H)

EXAMPLE 116

Synthesis by another process of 1-(3-amino-4,6-difluorophenyl)-7-chloro-6-fluoro-4-oxo-1,4-dihydro-1,8-naphthyridine-3-carboxylic acid Ethyl 7-chloro-1-(3-ethoxycarbonylamino-4,6-difluorophenyl)-6-fluoro-4-oxo-1,4-dihydro-1,8-naphthyridine-3-carboxylate (200 mg) was added to a mixture of 2 ml of 6N hydrochloric acid and 2 ml of acetic acid. The solution was stirred and heated at reflux for 4 days. The reaction solution was allowed to cool down whereupon the precipitate was collected by filtration. The filtrate was concentrated in vacua and 6 ml of 6N hydrochloric acid was added to the residue. The solution was stirred and heated at reflux for 18 hours. The reaction solution was concentrated in vacua and 1 ml of ethanol was added to the residue. The solution was allowed to stand whereupon the precipitate was collected by filtration and washed with ethanol and then diisopropyl ether to give 29 mg of the title compound as a pale yellow powder.

EXAMPLE 117

7-(3-aminoazetidin-1-yl)-1-(3-amino-4,6-difluorophenyl)-6-fluoro-1,4-dihydro-4-oxo-1,8-naphthyridine-3-carboxylic acid To 200 ml of acetonitrile were added 3.7 g of 1-(3-amino-4,6-difluorophenyl)-7-chloro-6-fluoro-1,4-dihydro-4-oxo-1,8-naphthyridine-3-carboxylic acid, 2.18 g of 3-aminoazetidine dihydrochloride, and 6.06 g of triethylamine. The solution was stirred at 80° C. for 15 hours. The reaction solution was cooled whereupon the precipitated solid was collected by filtration and washed with ethanol and isopropyl ether to give 3.7 g of the title compound.

Properties: pale yellow powder mp: 168.5–170.5° C.

$^1$H-NMR (d$_6$-DMSO) δ: 3.60–4.60 (m, 5H), 5.35 (brs, 2H), 6.95 (t, J=8 Hz, 1H), 7.35 (t, J=10 Hz, 1H), 8.03 (d, J=11.5 Hz, 1H), 8.68 (s, 1H)

EXAMPLE 118

1-(3-amino-4,6-difluorophenyl)-6-fluoro-7-(3-hydroxyazetidin-1-yl)-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-hydroxyazetidine hydrochloride, and triethylamine were used.

Properties: pale yellow powder mp: >253° C. (decomposed)

$^1$H-NMR (d$_6$-DMSO) δ: 3.60–4.65 (m, 5H), 5.35 (brs, 2H), 5.82 (brs, 1H), 6.95 (t, J=8 Hz, 1H), 7.35 (t, J=10 Hz, 1H), 8.03 (d, J=11.5 Hz, 1H), 8.68 (s, 1H)

EXAMPLE 119

1-(3-amino-4,6-difluorophenyl)-6-fluoro-7-(3-methylaminoazetidin-1-yl)-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid and 3-methylaminoazetidine dihydrochloride, and triethylamine were used.

Properties: colorless powder mp: 135.5–140.5° C.

$^1$H-NMR (d$_6$-DMSO) δ: 2.53 (s, 3H), 3.80–4.90 (m, 5H), 5.38 (brs, 2H), 6.97 (t, J=8 Hz, 1H), 7.36 (t, J=10 Hz, 1H), 8.11 (d, J=10.7 Hz, 1H), 8.70 (s, 1H)

EXAMPLE 120

1-(3-amino-4,6-difluorophenyl)-7-(3-ethylaminoazetidin-1-yl)-6-fluoro-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-ethylaminoazetidine dihydrochloride, and triethylamine were used.

Properties: colorless powder mp: 122.5–124° C.

$^1$H-NMR (d$_6$-DMSO) δ: 0.98 (t, J=7 Hz, 3H), 2.45 (q, J=7 Hz, 2H), 3.20–4.80 (m, 5H), 5.34 (brs, 2H), 6.94 (t, J=8 Hz, 1H), 7.35 (t, J=10 Hz, 1H), 8.01 (d, J=10.7 Hz, 1H), 8.67 (s, 1H)

EXAMPLE 121

1-(3-amino-4,6-difluorophenyl)-7-(3-dimethylaminoazetidin-1-yl)-6-fluoro-1,4-dihydro-4-oxo-1,8-naphthyridine-3-carboxylic acid hydrochloride The title compound in a free form was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-dimethylaminoazetidine dihydrochloride, and triethylamine were used. This solid (110 mg) was dissolved in 5 ml of chloroform and 2 ml of 4N hydrochloric acid/1,4-dioxane was added thereto. The solvent was distilled off and 2 ml of ethanol was added to the residue. The precipitated solid was collected by filtration to give 60 mg of the title compound.

Properties: pale yellow powder mp: >242° C. (decomposed)

$^1$H-NMR (d$_6$-DMSO) δ: 2.72 (s, 6H), 3.90–4.80 (m, 5H), 5.20–6.70 (br, 2H), 7.18 (t, J=8 Hz, 1H), 7.45 (t, J=10 Hz, 1H), 8.13 (d, J=11.1 Hz, 1H), 8.73 (s, 1H)

EXAMPLE 122

1-(3-amino-4,6-difluorophenyl)-6-fluoro-7-(trans-2-methyl-3-aminoazetidin-1-yl)-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, trans-2-methyl-3-aminoazetidine dihydrochloride, and triethylamine were used.

Properties: pale yellow powder mp: >237° C. (decomposed)

$^1$H-NMR (d$_6$-DMSO) δ: 0.90–1.35 (m, 3H), 3.20–3.55 (m, 2H), 3.80–4.60 (m, 2H), 5.37 (brs, 2H), 6.85–7.05 (m, 1H), 7.25–7.50 (m, 1H), 8.09 (d, J=9 Hz, 1H), 8.72 (s, 1H)

EXAMPLE 123

7-(3-aminoazetidin-1-yl)-1-(3-amino-4,6-difluorophenyl)-6-fluoro-1,4-dihydro-4-oxo-1,8-naphthyridine-3-carboxylic acid p-toluenesulfonic acid salt The title compound was obtained by the similar procedure as Example 52 except that Compound 117 was used.

Properties: pale red powder mp: 179–184° C.

$^1$H-NMR (d$_6$-DMSO) δ: 2.28 (s, 3H), 3.50–4.80 (m, 5H), 6.96 (t, J=8 Hz, 1H), 7.11 (d, J=8 Hz, 1H), 7.37 (t, J=10 Hz, 1H), 7.48 (d, J=8 Hz, 1H), 8.12 (d, J=11.1 Hz, 1H), 8.30 (brs, 3H), 8.74 (s, 1H)

EXAMPLE 124

7-(3-aminoazetidin-1-yl)-1-(3-amino-4,6-difluorophenyl)-6-fluoro-1,4-dihydro-4-oxo-1,8-naphthyridine-3-carboxylic acid methanesulfonic acid salt The title compound was obtained by the similar procedure as Example 52 except that Compound 117 and methanesulfonic acid were used.

Properties: pale red powder mp: >214° C. (decomposed)

$^1$H-NMR (d$_6$-DMSO) δ: 2.34 (s, 3H), 3.80–4.80 (m, 5H), 6.96 (t, J=8 Hz, 1H), 7.37 (t, J=10 Hz, 1H), 8.14 (d, J=11.2 Hz, 1H), 8.31 (brs, 3H), 8.74 (s, 1H)

EXAMPLE 125

7-(3-amino-3-methylazetidin-1-yl)-1-(3-amino-4,6-difluorophenyl)-6-fluoro-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-amino-3-methylazetidine dihydrochloride, and triethylamine were used.

Properties: colorless powder mp: 244–246.5° C.

$^1$H-NMR (d$_6$-DMSO) δ: 1.42 (s, 3H), 3.20–4.55 (m, 4H), 5.37 (brs, 2H), 6.95 (t, J=8 Hz, 1H), 7.36 (t, J=10 Hz, 1H), 8.07 (d, J=11.1 Hz, 1H), 8.71 (s, 1H)

EXAMPLE 126

7-(3-L-alanylaminoazetidin-1-yl)-1-(3-amino-4,6-difluorophenyl)-6-fluoro-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-L-alanylaminoazetidine dihydrochloride, and triethylamine were used.

Properties: pale yellow powder mp: 208.5–214° C.

$^1$H-NMR (d$_6$-DMSO) δ: 1.28 (d, J=6.8 Hz, 3H), 3.55–3.75 (m, 1H), 3.70–4.80 (m, 5H), 5.38 (brs, 2H), 6.97 (t, J=8 Hz, 1H), 7.36 (t, J=10 Hz, 1H), 8.07 (d, J=11.1 Hz, 1H), 8.70 (s, 1H), 9.07 (brs, 1H)

EXAMPLE 127

1-(3-amino-4,6-difluorophenyl)-6-fluoro-7-(3-L-valylaminoazetidin-1-yl)-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-L-valylaminoazetidine dihydrochloride, and triethylamine were used.

Properties: colorless powder mp: 262.5–264.5° C.

$^1$H-NMR (d$_6$-DMSO) δ: 0.78 (d, J=7 Hz, 3H), 0.85 (d, J=7 Hz, 3H), 1.70–1.95 (m, 1H), 2.91 (d, J=5.5 Hz, 1H), 3.70–4.80 (m, 5H), 5.35 (brs, 2H), 6.95 (t, J=8 Hz, 1H), 7.35 (t, J=10 Hz, 1H), 8.06 (d, J=11.1 Hz, 1H), 8.52 (brs, 1H), 8.69 (s, 1H)

EXAMPLE 128

1-(3-amino-4,6-difluorophenyl)-6-fluoro-7-(3-methylaminopyrrolidin-1-yl)-4-oxo-1,4-dihydro-1,8-naphthyridine-3-carboxylic acid The title compound was obtained by the similar procedure as Example 48 except that 3-methylaminopyrrolidine dihydrochloride was used.

Properties: colorless powder mp: 273–276° C. (decomposed)

$^1$H-NMR (d$_6$-DMSO) δ: 1.79 (m, 1H), 1.93 (m, 1H), 2.24 (s, 3H), 5.35 (brs, 2H), 6.96 (t, J=8 Hz, 1H), 7.36 (t, J=10 Hz, 1H), 8.03 (d, J=12 Hz, 1H), 8.68 (s, 1H)

EXAMPLE 129

1-(3-amino-4,6-difluorophenyl)-6-fluoro-7-[(3S)-3-(methylamino)pyrrolidin-1-yl]-4-oxo-1,4-dihydro-1,8-naphthyridine-3-carboxylic acid The title compound was obtained by the similar procedure as Example 48 except that (3S)-3-(methylamino)pyrrolidine dihydrochloride was used.

Properties: pale brown powder mp: 246–248° C. (decomposed)

$^1$H-NMR (d$_6$-DMSO) δ: 1.79 (m, 1H), 1.92 (m, 1H), 2.23 (s, 3H), 3.18 (m, 2H), 5.35 (brs, 2H) 6.97 (t, J=8 Hz, 1H), 7.36 (t, J=10 Hz, 1H), 8.02 (d, J=13 Hz, 1H), 8.68 (s, 1H)

EXAMPLE 130

1-(3-amino-4,6-difluorophenyl)-6-fluoro-7-[(3S)-3-(ethylamino)pyrrolidin-1-yl]-4-oxo-1,4-dihydro-1,8-naphthyridine-3-carboxylic acid The title compound was obtained by the similar procedure as Example 48 except that (3S)-3-(ethylamino)pyrrolidine dihydrochloride was used.

Properties: pale brown powder mp: 248–251° C. (decomposed)

$^1$H-NMR (d$_6$-DMSO) δ: 0.98 (t, J=7 Hz, 3H), 1.75 (m, 1H), 1.95 (m, 1H), 5.35 (brs, 2H) 6.96 (t, J=8 Hz, 1H), 7.36 (t, J=11 Hz, 1H), 8.01 (d, J=12 Hz, 1H), 8.67 (s, 1H)

EXAMPLE 131

1-(3-amino-4,6-difluorophenyl)-7-(3-amino-3-methylpyrrolidin-1-yl)-6-fluoro-4-oxo-1,4-dihydro-1,8-naphthyridine-3-carboxylic acid The title compound was obtained by the similar procedure as Example 48 except that 3-amino-3-methylpyrrolidine dihydrochloride was used.

Properties: colorless powder mp: 223–225° C.

$^1$H-NMR (d$_6$-DMSO) δ: 1.20 (d, J=3 Hz, 3H), 1.60 (m, 1H), 1.71 (m, 1H), 5.35 (brs, 2H), 6.96 (t, J=8 Hz, 1H), 7.36 (t, J=10 Hz, 1H), 7.99 (d, J=13 Hz, 1H), 8.63 (s, 1H)

EXAMPLE 132

1-(3-amino-4,6-difluorophenyl)-7-(3-aminomethyl pyrrolidin-1-yl)-6-fluoro-4-oxo-1,4-dihydro-1,8-naphthyridine-3-carboxylic acid The title compound was obtained by the similar procedure as Example 48 except that 3-aminomethylpyrrolidine dihydrochloride was used.

Properties: colorless powder mp: 205–210° C.

$^1$H-NMR (d$_6$-DMSO) δ: 1.42–1.98 (m, 2H), 2.60 (d, J=7 Hz, 2H), 5.34 (s, 2H), 6.96 (t, J=8 Hz, 1H), 7.35 (t, J=10 Hz, 1H), 8.01 (d, J=12 Hz, 1H), 8.66 (s, 1H)

EXAMPLE 133

1-(3-amino-4,6-difluorophenyl)-7-(4-aminopiperidin-1-yl)-6-fluoro-4-oxo-1,4-dihydro-1,8-naphthyridine-3-carboxylic acid The title compound was obtained by the similar procedure as Example 48 except that 4-aminopiperidine dihydrochloride was used.

Properties: colorless powder mp: 212–215° C.

$^1$H-NMR (d$_6$-DMSO) δ: 1.28 (m, 2H), 1.74 (m, 2H), 2.95 (m, 1H), 3.10 (m, 2H), 4.06 (m, 2H), 5.39 (s, 2H), 6.97 (t, J=8 Hz, 1H), 7.36 (t, J=10 Hz, 1H), 8.06 (d, J=12 Hz, 1H), 8.67 (s, 1H)

EXAMPLE 134

1-(3-amino-4,6-difluorophenyl)-7-(cis-3-amino-4-methoxypyrrolidin-1-yl)-6-fluoro-1,4-dihydro-4-oxo-1,8-naphthyridine-3-carboxylic acid The title compound was obtained by the similar procedure as Example 48 except that cis-3-amino-4-methoxypyrrolidine was used.

Properties: pale yellow powder mp: >164° C. (decomposed)

$^1$H-NMR (d$_6$-DMSO) δ: 3.13 (s, 3H), 3.73 (m, 2H), 3.93 (m, 1H), 5.38 (brs, 2H), 6.97 (m, 1H), 7.37 (m, 1H), 8.10 (d, J=12 Hz, 1H), 8.71 (s, 1H)

EXAMPLE 135

1-(3-amino-4,6-difluorophenyl)-6-fluoro-7-(3-(2-hydroxyethylamino)-pyrrolidine)-1,4-dihydro-4-oxo-1,8-naphthyridine-3-carboxylic acid The title compound was obtained by the similar procedure as Example 48 except that 3-(2-hydroxyethylamino) pyrrolidine dihydrochloride was used.

Properties: pale yellow powder mp: >235° C. (decomposed)

$^1$H-NMR (d$_6$-DMSO) δ: 1.65–2.13 (m, 2H), 2.52–2.70 (m, 2H), 3.42–3.58 (m, 2H), 4.55–4.73 (m, 1H), 5.36 (brs, 2H), 6.97 (t, J=8 Hz, 1H), 7.36 (t, J=11 Hz, 1H), 8.04 (d, J=13 Hz, 1H), 8.69 (s, 1H)

EXAMPLE 136

1-(3-amino-4,6-difluorophenyl)-7-(7-amino-5-azaspiro[2.4]-heptan-5-yl)-6-fluoro-1,4-dihydro-4-oxo-1,8-naphthyridine-3-carboxylic acid hydrochloride To 2 ml of dimethylsulfoxide were added 173 mg of 7-tert-butyloxycarbonylamino-5-azaspiro[2.4]heptane B form and 164 mg of triethylamine. With heating and stirring at 80° C., 200 mg of 1-(3-amino-4,6-difluorophenyl)-7-chloro-6-fluoro-4-oxo-1,4-dihydro-1,8-naphthyridine-3-carboxylic acid was added to the solution, which was stirred at the temperature overnight. After the reaction solution was allowed to cool down, diethyl ether was added thereto. The diethyl ether layer was concentrated in vacua. The residue was combined with chloroform, washed with water, and dried over magnesium sulfate. The solvent was distilled off. Diethyl ether was added to the residue whereupon the solid was collected by filtration. To the solid were added 30 ml of chloroform and 5 ml of 4N hydrochloric acid/dioxane. After stirring at room temperature for 2 hours, the reaction solution was concentrated in vacua. Diethyl ether was added to the residue whereupon the solid was collected by filtration and washed with diethyl ether to give 120 mg of the title compound.

Properties: yellow powder mp: >222° C. (decomposed)

$^1$H-NMR (d$_6$-DMSO) δ: 0.78 (m, 4H), 3.26–4.44 (m, 6H), 7.09 (m, 1H), 7.41 (m, 1H), 8.12 (d, J=13 Hz, 1H), 8.35 (brs, 3H), 8.73 (s, 1H)

EXAMPLE 137

7-(3-aminoazetidin-1-yl)-6-fluoro-1-(2,4-difluoro-5-methylaminophenyl)-1,4-dihydro-4-oxo-1,8-naphthyridine-3-carboxylic acid The title compound was obtained by the similar procedure as Example 117 except that 7-chloro-6-fluoro-1-(2,4-difluoro-5-methylaminophenyl)-1,4-dihydro-4-oxo-1,8-naphthyridine-3-carboxylic acid, 3-aminoazetidine dihydrochloride and triethylamine were used.

Properties: pale yellow powder mp: >231° C. (decomposed)

$^1$H-NMR (d$_6$-DMSO) δ: 2.69 (d, J=4.3 Hz, 3H), 3.80–4.80 (m, 5H), 5.83 (brs, 1H), 6.96 (t, J=8 Hz, 1H), 7.41 (t, J=11 Hz, 1H), 8.14 (d, J=12 Hz, 1H), 8.20–8.60 (br, 2H), 8.76 (s, 1H)

EXAMPLE 138

7-[(3S)-3-aminopyrrolidin-1-yl]-1-(3-ethoxycarbonylamino-4,6-difluorophenyl)-6-fluoro-4-oxo-1,4-dihydro-1,8-naphthyridine-3-carboxylic acid To 350 μl of N,N-dimethylformamide were added 68 mg of 1-(3-ethoxycarbonylamino-4,6-difluorophenyl)-7-chloro-6-fluoro-4-oxo-1,4-dihydro-1,8-naphthyridine-3-carboxylic acid and 70 mg of (3S)-3-aminopyrrolidine. The solution was stirred at 80° C. for 20 minutes. Then 0.5 ml of ethanol was added. The reaction solution was allowed to cool down whereupon the precipitate was collected by filtration and washed with ethanol and then diisopropyl ether to give 73 mg of the title compound.

Properties: colorless powder mp: >280° C.

$^1$H-NMR (d$_6$-DMSO) δ: 1.23 (t, J=7 Hz, 3H), 1.34 (m, 1H), 1.53–1.95 (m, 3H), 2.42 (m), 2.74 (m), 4.12 (q, J=7 Hz, 2H), 7.63 (t, J=10 Hz, 1H), 7.95 (t, J=8 Hz, 1H), 7.99 (d, J=7 Hz, 1H), 8.63 (s, 1H)

EXAMPLE 139

7-(3-aminoazetidin-1-yl)-1-(3-amino-4,6-difluorophenyl)-1,4-dihydro-4-oxo-1,8-naphthyridine-3-carboxylic acid With stirring at 80° C., 100 mg of 1-(3-amino-4,6-difluorophenyl)-7-chloro-1,4-dihydro-4-oxo-1,8-naphthyridine-3-carboxylic acid was added to a solution of 61 mg of 3-aminoazetidine dihydrochloride and 119 mg of N-methylpyrrolidine in 3 ml of acetonitrile. The solution was stirred at 80° C. for 2 hours and 50 minutes. After the reaction solution was allowed to cool down, decantation with diethyl ether was carried out. The solid was dispersed by adding a small amount of ethanol and collected by filtration. The solid was washed with ethanol and then diethyl ether to give 63 mg of the title compound.

Properties: pale yellow powder mp: >240° C. (decomposed)

$^1$H-NMR (d$_6$-DMSO) δ: 3.50–4.48 (br, 5H), 5.35 (brs, 2H), 6.73 (d, J=9 Hz, 1H), 6.96 (t, J=9 Hz, 1H), 7.35 (t, J=10 Hz, 1H), 8.32 (d, J=9 Hz, 1H), 8.69 (s, 1H)

EXAMPLE 140

1-(3-amino-4,6-difluorophenyl)-7-[(3S)-3-aminopyrrolidin-1-yl]-1,4-dihydro-4-oxo-1,8-naphthyridine-3-carboxylic acid The title compound was obtained by the similar procedure as Example 139 except that (3S)-3-aminopyrrolidine as used.

Properties: pale red brown powder mp: >261° C. (decomposed)

$^1$H-NMR (d$_6$-DMSO) δ: 1.53–1.84 (m, 1H), 1.84–2.15 (m, 1H), 5.33 (brs, 2H), 6.82 (t, J=10 Hz, 1H), 6.97 (t, J=8 Hz, 1H), 7.35 (t, J=10 Hz, 1H), 8.28 (d, J=10 Hz, 1H), 8.65 (s, 1H)

EXAMPLE 141

1-(3-amino-6-chloro-4-fluorophenyl)-7-(3-aminoazetidin-1-yl)-6-fluoro-1,4-dihydro-4-oxo-1,8-naphthyridine-3-carboxylic acid The title compound was obtained by the similar procedure as Example 139 except that 1-(3-amino-6-chloro-4-fluorophenyl)-7-chloro-6-fluoro-1,4-dihydro-4-oxo-1,8-naphthyridine-3-carboxylic acid was used.

Properties: pale yellow powder mp: 200–203° C.

$^1$H-NMR (d$_6$-DMSO) δ: 3.70–4.48 (br, 3H), 5.69 (brs, 2H), 6.96 (d, J=8 Hz, 1H), 7.46 (d, J=12 Hz, 1H), 8.04 (d, J=12 Hz, 1H), 8.62 (s, 1H)

EXAMPLE 142

1-(3-amino-6-methyl-4-fluorophenyl)-7-(3-aminoazetidin-1-yl)-6-fluoro-1,4-dihydro-4-oxo-1,8-naphthyridine-3-carboxylic acid The title compound was obtained by the similar procedure as Example 117 except that 1-(3-amino-6-methyl-4-fluorophenyl)-7-chloro-6-fluoro-1,4-dihydro-4-oxo-1,8-naphthyridine-3-carboxylic acid was used.

Properties: pale yellow powder mp: >238° C. (decomposed)

$^1$H-NMR (d$_6$-DMSO) δ: 1.82 (s, 3H), 2.94–4.28 (br, 5H), 5.27 (brs, 3H), 6.74 (d, J=9 Hz, 1H), 7.09 (d, J=12 Hz, 1H), 8.09 (d, J=10 Hz, 1H), 8.52 (s, 1H)

EXAMPLE 143

1-(3-amino-4-fluorophenyl)-7-[(3S)-3-aminopyrrolidin-1-yl]-6-fluoro-1,4-dihydro-4-oxo-1,8-naphthyridine-3-carboxylic acid The title compound was obtained by the similar procedure as Example 60 except that 1-(3-amino-4-fluorophenyl)-7- chloro-6-fluoro-1,4-dihydro-4-oxo-1,8-naphthyridine-3-carboxylic acid and (3S)-3-aminopyrrolidine were used.

Properties: brown powder mp: 262–265° C.

¹H-NMR (d₆-DMSO) δ: 1.56–1.83 (m, 1H), 1.86–2.09 (m, 1H), 5.50 (brs, 2H), 6.67–6.78 (m, 1H), 6.92 (d, J=9 Hz, 1H), 7.17 (t, J=12 Hz, 1H), 8.03 (d, J=13 Hz, 1H), 8.53 (s, 1H)

EXAMPLE 144

1-(3-amino-4-fluorophenyl)-7-[(3S,4S)-3-amino-4-methylpyrrolidin-1-yl]-6-fluoro-1,4-dihydro-4-oxo-1,8-naphthyridine-3-carboxylic acid The title compound was obtained by the similar procedure as Example 60 except that 1-(3-amino-4-fluorophenyl)-7-chloro-6-fluoro-1,4-dihydro-4-oxo-1,8-naphthyridine-3-carboxylic acid and (3S,4S)-3-amino-4-methylpyrrolidine were used.

Properties: brown powder mp: >270° C.

¹H-NMR (d₆-DMSO) δ: 0.96 (d, J=7 Hz, 3H), 2.12 (brs, 1H), 5.50 (s, 2H), 6.68–6.76 (m, 1H), 6.89–7.01 (m, 1H), 7.19 (t, J=11 Hz, 1H), 8.03 (d, J=13 Hz, 1H), 8.53 (s, 1H)

EXAMPLE 145

1-(3-amino-4,6-difluorophenyl)-7-(cis-3-hydroxy-4-methylpyrrolidin-1-yl)-6-fluoro-1,4-dihydro-4-oxoquinoline-3-carboxylic acid The title compound was obtained by the similar procedure as Example 60 except that 1-(3-amino-4,6-difluorophenyl)-6,7-difluoro-1,4-dihydro-4-oxoquinoline-3-carboxylic acid and cis-3-hydroxy-4-methylpyrrolidine were used.

Properties: brown powder mp: 174–180° C.

¹H-NMR (d₆-DMSO) δ: 0.94 (d, J=7 Hz, 3H), 2.11 (m, 1H), 2.86–3.81 (m, 4H), 3.86 (m, 1H), 5.18 (brs, 2H), 5.93 (d, J=6 Hz, 1H), 7.04 (t, J=8 Hz, 1H), 7.50 (t, J=10 Hz, 1H), 7.86 (d, J=13 Hz, 1H), 8.62 (s, 1H)

EXAMPLE 146

1-(3-amino-4,6-difluorophenyl)-7-(trans-3-amino-4-methylpyrrolidin-1-yl)-6-fluoro-1,4-dihydro-4-oxoquinoline-3-carboxylic acid The title compound was obtained by the similar procedure as Example 60 except that 1-(3-amino-4,6-difluorophenyl)-6,7-difluoro-1,4-dihydro-4-oxoquinoline-3-carboxylic acid and trans-3-amino-4-methylpyrrolidine dihydrochloride were used.

Properties: pale yellow powder mp: >164° C. (decomposed)

¹H-NMR (d₆-DMSO) δ: 1.09 (d, J=7 Hz, 3H), 2.28 (m, 1H), 2.97–3.91 (m, 5H), 5.58 (brs, 2H), 5.96 (d, J=7 Hz, 1H), 7.05 (t, J=8 Hz, 1H), 7.52 (t, J=10 Hz, 1H), 7.92 (d, J=14 Hz, 1H), 8.66 (s, 1H)

EXAMPLE 147

1-(3-amino-4,6-difluorophenyl)-6-fluoro-7-[(3S)-3-methylaminopyrrolidin-1-yl]-1,4-dihydro-4-oxoquinoline-3-carboxylic acid The title compound was obtained by the similar procedure as Example 60 except that 1-(3-amino-4,6-difluorophenyl)-6,7-difluoro-1,4-dihydro-4-oxoquinoline-3-carboxylic acid and (3S)-3-methylaminopyrrolidine were used.

Properties: pale yellow powder mp: 188–199° C.

¹H-NMR (d₆-DMSO) δ: 1.86 (brs, 1H), 2.00 (brs, 1H), 2.30 (s, 3H), 3.11–3.66 (m, 5H), 5.54 (brs, 2H), 5.95 (d, J=7 Hz, 1H), 7.04 (t, J=8 Hz, 1H), 7.50 (t, J=11 Hz, 1H), 7.86 (d, J=14 Hz, 1H), 8.63 (s, 1H)

EXAMPLE 148

7-(3-aminoazetidin-1-yl)-1-(3-amino-4,6-difluorophenyl)-6-fluoro-1,4-dihydro-4-oxoquinoline-3-carboxylic acid The title compound was obtained by the similar procedure as Example 60 except that 1-(3-amino-4,6-difluorophenyl)-6,7-difluoro-1,4-dihydro-4-oxoquinoline-3-carboxylic acid and 3-aminoazetidine dihydrochloride were used.

Properties: colorless powder mp: >183° C. (decomposed)

¹H-NMR (d₆-DMSO) δ: 3.76 (brs, 2H), 3.91 (m, 1H), 4.24 (brs, 2H), 5.55 (brs, 2H), 5.77 (d, J=7 Hz, 1H), 7.02 (t, J=8 Hz, 1H), 7.50 (t, J=10 Hz, 1H), 7.88 (d, J=12 Hz, 1H), 8.64 (s, 1H)

EXAMPLE 149

1-(3-amino-4,6-difluorophenyl)-7-(trans-3-amino-4-hydroxypyrrolidin-1-yl)-6,8-difluoro-1,4-dihydro-4-oxoquinoline-3-carboxylic acid The title compound was obtained by the similar procedure as Example 60 except that 1-(3-amino-4,6-difluorophenyl)-6,7,8-trifluoro-1,4-dihydro-4-oxoquinoline-3-carboxylic acid and trans-3-amino-4-hydroxypyrrolidine dihydrochloride were used.

Properties: brown powder mp: >145° C. (decomposed)

¹H-NMR (d₆-DMSO) δ: 3.92–4.26 (m, 4H), 5.46 (brs, 2H), 7.10 (t, J=9 Hz, 1H), 7.40 (t, J=11 Hz, 1H), 7.86 (d, J=14 Hz, 1H), 8.52 (s, 1H)

EXAMPLE 150

7-(3-aminoazetidin-1-yl)-1-(3-amino-4,6-difluorophenyl)-6,8-difluoro-1,4-dihydro-4-oxoquinoline-3-carboxylic acid The title compound was obtained by the similar procedure as Example 60 except that 1-(3-amino-4,6-difluorophenyl)-6,7,8-trifluoro-1,4-dihydro-4-oxoquinoline-3-carboxylic acid and 3-aminoazetidine dihydrochloride were used.

Properties: colorless powder mp: >203° C. (decomposed)

¹H-NMR (d₆-DMSO) δ: 3.90 (m, 1H), 4.10 (m, 1H), 4.49 (m, 2H), 5.46 (brs, 2H), 7.08 (t, J=9 Hz, 1H), 7.39 (t, J=10 Hz, 1H), 7.81 (d, J=13 Hz, 1H), 8.48 (s, 1H)

EXAMPLE 151

1-(3-amino-4,6-difluorophenyl)-6,8-difluoro-7-(3-hydroxyazetidin-1-yl)-1,4-dihydro-4-oxoquinoline-3-carboxylic acid The title compound was obtained by the similar procedure as Example 60 except that 1-(3-amino-4,6-difluorophenyl)-

6,7,8-trifluoro-1,4-dihydro-4-oxoquinoline-3-carboxylic acid and 3-hydroxyazetidine hydrochloride were used.

Properties: colorless powder mp: 218–225° C.

¹H-NMR (d₆-DMSO) δ: 4.13 (brs, 2H), 4.50 (brs, 3H), 5.44 (brs, 2H), 5.72 (brs, 1H), 7.08 (t, J=8 Hz, 1H), 7.39 (t, J=10 Hz, 1H), 7.79 (d, J=13 Hz, 1H), 8.46 (s, 1H)

EXAMPLE 152

7-(3-aminoazetidin-1-yl)-1-(3-amino-4,6-difluorophenyl)-8-chloro-6-fluoro-1,4-dihydro-4-oxoquinoline-3-carboxylic acid The title compound was obtained by the similar procedure as Example 60 except that 1-(3-amino-4,6-difluorophenyl)-8-chloro-6,7-difluoro-1,4-dihydro-4-oxoquinoline-3-carboxylic acid and 3-aminoazetidine dihydrochloride were used.

Properties: pale yellow powder mp: >270° C.

¹H-NMR (d₆-DMSO) δ: 3.75 (m, 1H), 4.10 (m, 2H), 4.66 (m, 2H), 5.43 (brs, 2H), 6.97 (t, J=8 Hz, 1H), 7.36 (t, J=11 Hz, 1H), 7.87 (d, J=14 Hz, 1H), 8.44 (s, 1H)

EXAMPLE 153

1-(3-amino-4,6-difluorophenyl)-7-[(3S)-3-aminopyrrolidin-1-yl]-8-chloro-6-fluoro-1,4-dihydro-4-oxoquinoline-3-carboxylic acid The title compound was obtained by the similar procedure as Example 60 except that 1-(3-amino-4,6-difluorophenyl)-8-chloro-6,7-difluoro-1,4-dihydro-4-oxoquinoline-3-carboxylic acid and (3S)-3-aminopyrrolidine were used.

Properties: pale yellow powder mp: >205° C. (decomposed)

¹H-NMR (d₆-DMSO) δ: 1.17 (m, 1H), 2.09 (m, 1H), 3.02–3.81 (m, 5H), 5.41 (brs, 2H), 6.97 (m, 1H), 7.38 (t, J=11 Hz, 1H), 7.94 (d, J=14 Hz, 1H), 8.50 (s, 1H)

EXAMPLE 154

1-(3-amino-4,6-difluorophenyl)-8-chloro-6-fluoro-7-(3-hydroxyazetidin-1-yl)-1,4-dihydro-4-oxoquinoline-3-carboxylic acid The title compound was obtained by the similar procedure as Example 60 except that 1-(3-amino-4,6-difluorophenyl)-8-chloro-6,7-difluoro-1,4-dihydro-4-oxoquinoline-3-carboxylic acid and 3-hydroxyazetidine hydrochloride were used.

Properties: pale yellow powder mp: 145–150° C.

¹H-NMR (d₆-DMSO) δ: 4.18 (brs, 2H), 4.47 (brs, 1H), 4.71 (brs, 2H), 5.41 (brs, 2H), 5.71 (d, J=5 Hz, 1H), 6.96 (t, J=8 Hz, 1H), 7.37 (t, J=10 Hz, 1H), 7.88 (d, J=14 Hz, 1H), 8.44 (s, 1H)

EXAMPLE 155

1-(3-amino-4,6-difluorophenyl)-8-chloro-6-fluoro-7-piperazino-1,4-dihydro-4-oxoquinoline-3-carboxylic acid The title compound was obtained by the similar procedure as Example 60 except that 1-(3-amino-4,6-difluorophenyl)-8-chloro-6,7-difluoro-1,4-dihydro-4-oxoquinoline-3-carboxylic acid and piperazine were used.

Properties: pale yellow powder mp: >232° C. (decomposed)

¹H-NMR (d₆-DMSO) δ: 2.87 (brs, 4H), 3.19 (brs, 4H), 5.43 (brs, 2H), 6.97 (t, J=8 Hz, 1H), 7.37 (t, J=11 Hz, 1H), 8.07 (d, J=12 Hz, 1H), 8.54 (s, 1H)

EXAMPLE 156

1-(3-amino-4,6-difluorophenyl)-7-(3-amino-3-methylazetidin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and 3-amino-3-methylazetidine were used.

Properties: yellow powder mp: 252–257° C.

¹H-NMR (d₆-DMSO) δ: 1.35 (s, 3H), 4.17 (brs, 2H), 4.30 (brs, 2H), 5.42 (brs, 2H), 6.96 (t, J=8 Hz, 1H), 7.36 (t, J=10 Hz, 1H), 7.87 (d, J=14 Hz, 1H), 8.43 (s, 1H)

EXAMPLE 157

1-(3-amino-4,6-difluorophenyl)-8-chloro-6-fluoro-7-(3-methylaminoazetidin-1-yl)-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and 3-methylaminoazetidine were used.

Properties: pale yellow powder mp: 220–224° C.

¹H-NMR (d₆-DMSO) δ: 2.20 (s, 3H), 3.45 (brs, 1H), 4.12 (brs, 2H), 4.63 (brs, 2H), 5.42 (brs, 2H), 6.96 (t, J=8 Hz, 1H), 7.36 (t, J=10 Hz, 1H), 7.86 (d, J=14 Hz, 1H), 8.43 (s, 1H)

EXAMPLE 158

1-(3-amino-4,6-difluorophenyl)-8-chloro-6-fluoro-7-(3,5-dimethylpiperazino)-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and 2,6-dimethylpiperazine were used.

Properties: pale yellow powder mp: >270° C.

¹H-NMR (d₆-DMSO) δ: 0.96 (d, J=6 Hz, 6H), 2.80 (m, 2H), 2.91 (m, 2H), 3.08 (m, 2H), 5.43 (brs, 2H), 6.97 (t, J=8 Hz, 1H), 7.38 (t, J=11 Hz, 1H), 8.07 (d, J=12 Hz, 1H), 8.56 (s, 1H)

EXAMPLE 159

7-(3-aminoazetidin-1-yl)-1-(3-amino-4,6-difluorophenyl)-6-fluoro-5-hydroxy-1,4-dihydro-4-oxoquinoline-3-carboxylic acid The title compound was obtained by the similar procedure as Example 60 except that 1-(3-amino-4,6-difluorophenyl)-6,7-difluoro-5-hydroxy-1,4-dihydro-4-oxoquinoline-3-carboxylic acid and 3-aminoazetidine dihydrochloride were used.

Properties: pale yellow powder mp: >262° C. (decomposed)

$^1$H-NMR (d$_6$-DMSO) δ: 3.75–4.02 (m, 3H), 4.24 (brs, 2H), 5.25 (d, J=7 Hz, 1H), 5.54 (brs, 2H), 6.98 (t, J=8 Hz, 1H), 7.49 (t, J=10 Hz, 1H), 8.48 (s, 1H)

EXAMPLE 160

1-(3-amino-4,6-difluorophenyl)-7-[(3S)-3-aminopyrrolidin-1-yl]-6-fluoro-5-hydroxy-1,4-dihydro-4-oxoquinoline-3-carboxylic acid The title compound was obtained by the similar procedure as Example 60 except that 1-(3-amino-4,6-difluorophenyl)-6,7-difluoro-5-hydroxy-1,4-dihydro-4-oxoquinoline-3-carboxylic acid and (3S)-3-aminopyrrolidine were used.

Properties: pale yellow powder mp: >237° C. (decomposed)

$^1$H-NMR (d$_6$-DMSO) δ: 2.01 (m, 1H), 2.21 (m, 1H), 3.34–4.97 (m, 5H), 5.46 (d, J=7 Hz, 1H), 6.98 (t, J=8 Hz, 1H), 7.50 (t, J=10 Hz, 1H), 8.64 (s, 1H)

EXAMPLE 161

7-(3-aminoazetidin-1-yl)-1-(3-amino-4,6-difluorophenyl)-6-fluoro-5-methyl-1,4-dihydro-4-oxoquinoline-3-carboxylic acid The title compound was obtained by the similar procedure as Example 60 except that 1-(3-amino-4,6-difluorophenyl)-6,7-difluoro-5-methyl-1,4-dihydro-4-oxoquinoline-3-carboxylic acid and 3-aminoazetidine dihydrochloride were used.

Properties: pale yellow powder mp: >270° C.

$^1$H-NMR (d$_6$-DMSO) δ: 2.75 (brs, 3H), 3.90 (brs, 2H), 4.01 (brs, 1H), 4.26 (brs, 2H), 5.55 (brs, 2H), 5.65 (d, J=7 Hz, 1H), 6.99 (t, J=8 Hz, 1H), 7.49 (t, J=11 Hz, 1H), 8.59 (s, 1H)

EXAMPLE 162

1-(3-amino-4,6-difluorophenyl)-7-[(3S)-3-aminopyrrolidin-1-yl]-6-fluoro-5-methyl-1,4-dihydro-4-oxoquinoline-3-carboxylic acid The title compound was obtained by the similar procedure as Example 60 except that 1-(3-amino-4,6-difluorophenyl)-6,7-difluoro-5-methyl-1,4-dihydro-4-oxoquinoline-3-carboxylic acid and (3S)-3-aminopyrrolidine were used.

Properties: pale brown powder mp: >197° C. (decomposed)

$^1$H-NMR (d$_6$-DMSO) δ: 1.68 (m, 1H), 1.96 (m, 1H), 3.01–3.65 (m, 5H), 5.53 (brs, 2H), 5.81 (d, J=7 Hz, 1H), 6.99 (t, J=8 Hz, 1H), 7.49 (t, J=11 Hz, 1H), 8.55 (s, 1H)

EXAMPLE 163

5-amino-1-(3-amino-4,6-difluorophenyl)-7-[(3S)-3-aminopyrrolidin-1-yl]-6,8-difluoro-1,4-dihydro-4-oxoquinoline-3-carboxylic acid The title compound was obtained by the similar procedure as Example 60 except that 5-amino-1-(3-amino-4,6-difluorophenyl)-6,7,8-trifluoro-1,4-dihydro-4-oxoquinoline-3-carboxylic acid and (3S)-3-aminopyrrolidine were used.

Properties: pale yellow powder mp: >247° C. (decomposed)

$^1$H-NMR (d$_6$-DMSO) δ: 1.62 (m, 1H), 1.89 (m, 1H), 3.22 (m, 1H), 3.39–3.78 (m, 4H), 5.38 (brs, 2H), 7.02 (t, J=8 Hz, 1H), 7.23 (brs, 2H), 7.34 (t, J=10 Hz, 1H), 8.23 (s, 1H)

EXAMPLE 164

5-amino-7-(3-aminoazetidin-1-yl)-1-(3-amino-4,6-difluorophenyl)-6,8-difluoro-1,4-dihydro-4-oxoquinoline-3-carboxylic acid The title compound was obtained by the similar procedure as Example 60 except that 5-amino-1-(3-amino-4,6-difluorophenyl)-6,7,8-trifluoro-1,4-dihydro-4-oxoquinoline-3-carboxylic acid and 3-aminoazetidine dihydrochloride were used.

Properties: yellow powder mp: >237° C. (decomposed)

$^1$H-NMR (d$_6$-DMSO) δ: 4.04 (brs, 1H), 4.28 (brs, 2H), 4.48 (brs, 2H), 5.41 (brs, 2H), 7.05 (t, J=8 Hz, 1H), 7.30 (m, 1H), 8.25 (s, 1H)

EXAMPLE 165

7-(3-aminoazetidin-1-yl)-1-(3-amino-6-chloro-4-fluorophenyl)-6-fluoro-1,4-dihydro-4-oxoquinoline-3-carboxylic acid The title compound was obtained by the similar procedure as Example 139 except that 1-(3-amino-6-chloro-4-fluorophenyl)-6,7-difluoro-1,4-dihydro-4-oxoquinoline-3-carboxylic acid was used.

Properties: pale yellow powder mp: >208° C. (decomposed)

$^1$H-NMR (d$_6$-DMSO) δ: 3.88–4.58 (br, 5H), 5.69 (d, J=8 Hz, 1H), 5.92 (brs, 2H), 7.08 (d, J=8 Hz, 1H), 7.59 (d, J=10 Hz, 1H), 7.93 (d, J=13 Hz, 1H), 8.61 (s, 1H)

EXAMPLE 166

Synthesis by another process of ethyl 7-chloro-1-(2,4-difluoro-5-formylaminophenyl)-6-fluoro-1,4-dihydro-4-oxo-1,8-naphthyridine-3-carboxylate Ethyl 7-chloro-6-fluoro-1-(2,4-difluoro-5-nitrophenyl)-4-oxo-1,4-dihydro-1,8-naphthyridine-3-carboxylate (305 mg) was added to 1.5 ml of formic acid together with 400 mg of iron powder. The mixture was stirred at 80° C. for 3 hours. The insoluble was removed by filtration through celite whereupon the filtrate was concentrated in vacua. The precipitate was dispersed in ethanol, collected by filtration and washed with ethanol and then with diisopropyl ether to give 295 mg of the title compound as a pale yellow powder.

REFERENCE EXAMPLE 10

N-(t-butoxycarbonyl)-2,4-difluoro-m-phenylenediamine

N-(t-butoxycarbonyl)-2,4-difluoro-5-nitroaniline was obtained as colorless crystals by the similar procedure as Reference Example 8 except that t-butanol was used instead of ethanol.

This product (3.8 g) was added to 50 ml of methanol together with 360 mg of 10% palladium on carbon. Hydrogenation was carried out at room temperature for 4 days. After the catalyst was filtered off, the solvent was distilled off in vacua. The precipitate was dispersed in diisopropyl ether and collected by filtration to give 3.2 g of the title compound as pale brown crystals.

REFERENCE EXAMPLE 11

Ethyl 8-chloro-1-(2-chloro-4-fluorophenyl)-6,7-difluoro-1,4-dihydro-4-oxoquinoline-3-carboxylate The title compound was obtained by the similar procedure as Reference Example 6 except that 2-chloro-4-fluoroaniline was used.

Properties: colorless powder mp: 208–212° C.

$^1$H-NMR (CDCl$_3$) δ: 1.40 (t, J=7 Hz, 3H), 4.40 (q, J=7 Hz, 2H), 7.16–7.23 (m, 1H), 7.34 (dd, J=3 Hz, J=8 Hz, 1H), 7.48 (dd, J=5 Hz, J=9 Hz, 1H), 8.27 (s, 1H), 8.35 (t, J=9 Hz, 1H)

REFERENCE EXAMPLE 12

Ethyl 8-chloro-6,7-difluoro-1-(4-fluorophenyl)-1,4-dihydro-4-oxoquinoline-3-carboxylate The title compound was obtained by the similar procedure as Reference Example 6 except that 4-fluoroaniline was used.

Properties: colorless powder mp: 226–231° C.

$^1$H-NMR (CDCl$_3$) δ: 1.39 (t, J=7 Hz, 3H), 4.39 (q, J=7 Hz, 2H), 7.20–7.24 (m, 2H), 7.34–7.35 (m, 2H), 8.34 (t, J=9 Hz, 1H), 8.42 (s, 1H)

REFERENCE EXAMPLE 13

Ethyl 8-chloro-6,7-difluoro-1-(4-fluoro-2-methylphenyl)-1,4-dihydro-4-oxoquinoline-3-carboxylate The title compound was obtained by the similar procedure as Reference Example 6 except that 2-methyl-4-fluoroaniline was used.

Properties: pale yellow powder mp: 180–182° C.

$^1$H-NMR (CDCl$_3$) δ: 1.40 (t, J=7 Hz, 3H), 2.10 (s, 3H), 4.40 (q, J=7 Hz, 2H),.7.02–7.10 (m, 2H), 7.22–7.36 (m, 1H), 8.31 (s, 1H), 8.37 (t, J=9 Hz, 1H)

REFERENCE EXAMPLE 14

Ethyl 1-(2-bromo-4-fluorophenyl)-8-chloro-6,7-difluoro-1,4-dihydro-4-oxoquinoline-3-carboxylate The title compound was obtained by the similar procedure as Reference Example 6 except that 2-bromo-4-fluoroaniline was used.

Properties: pale yellow powder mp: 183–188° C.

$^1$H-NMR (CDCl$_3$) δ: 1.40 (t, J=7 Hz, 3H), 4.40 (q, J=7 Hz, 2H), 7.18–7.32 (m, 1H), 7.48–7.55 (m, 2H) 8.27 (s, .1H), 8.36 (t, J=9 Hz, 1H)

REFERENCE EXAMPLE 15

Ethyl 1-(2-methoxy-4-fluorophenyl)-8-chloro-6,7-difluoro-1,4-dihydro-4-oxoquinoline-3-carboxylate The title compound was obtained by the similar procedure as Reference Example 6 except that 2-methoxy-4-fluoroaniline was used.

Properties: colorless powder mp: 240–246° C. (decomposed)

$^1$H-NMR (CDCl$_3$) δ: 1.40 (t, J=7 Hz, 3H), 3.77 (s, 3H), 4.39 (q, J=7 Hz, 2H), 6.72–6.89 (m, 2H), 7.31 (dd, J=6 Hz, J=9 Hz, 1H) 8.30 (s, 1H), 8.34 (t, J=10 Hz, 1H)

REFERENCE EXAMPLE 16

Ethyl 8-chloro-1-(4-chloro-2-fluorophenyl)-6,7-difluoro-1,4-dihydro-4-oxoquinoline-3-carboxylate The title compound was obtained by the similar procedure as Reference Example 6 except that 4-chloro-2-fluoroaniline was used.

Properties: colorless powder mp: 159–160° C.

$^1$H-NMR (CDCl$_3$) δ: 1.40 (t, J=7 Hz, 3H), 4.39 (q, J=7 Hz, 2H), 7.31–7.47 (m, 2H), 8.32–8.40 (m, 2H)

REFERENCE EXAMPLE 17

Ethyl 8-chloro-6,7-difluoro-1-(2,4,6-trifluorophenyl)-1,4-dihydro-4-oxoquinoline-3-carboxylate The title compound was obtained by the similar procedure as Reference Example 6 except that 2,4,6-trifluoroaniline was used.

Properties: pale yellow powder mp: 135–149° C. (decomposed)

$^1$H-NMR (CDCl$_3$) δ: 1.40 (t, J=7 Hz, 3H), 4.40 (q, J=7 Hz, 2H), 6.93 (t, J=7 Hz, 1H), 8.25 (s, 1H), 8.34 (t, J=10 Hz, 1H)

REFERENCE EXAMPLE 18

8-chloro-6,7-difluoro-1-(2,4,6-trifluorophenyl)-1,4-dihydro-4-oxoquinoline-3-carboxylic acid Ethyl 8-chloro-6,7-difluoro-1-(2,4,6-trifluorophenyl)-1,4-dihydro-4-oxoquinoline-3-carboxylate (1.2 g) was added to 5 ml of conc. hydrochloric acid and 1 ml of acetic acid. The solution was heated at reflux for 3 hours. The reaction solution was allowed to cool down whereupon the precipitated solid was collected by filtration and washed with ethanol and diethyl ether to give 750 mg of the title compound.

Properties: pale red powder mp: >158° C. (decomposed)

$^1$H-NMR (d$_6$-DMSO) δ: 7.60–7.72 (m, 2H), 8.41 (t, J=9 Hz, 1H), 9.01 (s, 1H)

EXAMPLE 167

1-(3-amino-4,6-difluorophenyl)-7-(trans-3-amino-2-methylazetidin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and trans-3-amino-2-methylazetidine were used.

Properties: brown powder mp: >211° C. (decomposed)

$^1$H-NMR (d$_6$-DMSO) δ: 1.38 (brs, 3H), 3.73–3.90 (m, 1H), 4.69–4.82 (m, 1H), 4.82–4.97 (m, 1H), 5.32–5.48 (m, 1H), 5.49 (s, 1H), 6.70–7.59 (m, 2H), 7.94 (d, J=14.Hz, 1H), 8.48 (s, 1H)

EXAMPLE 168

1-(3-amino-4,6-difluorophenyl)-7-(4-methylpiperazin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and 4-methylpiperazine were used.

Properties: yellow powder mp: 198–205° C. (decomposed)

$^1$H-NMR (d$_6$-DMSO) δ: 2.54 (s, 3H), 2.81 (brs, 4H), 3.42 (brs, 4H), 7.01 (t, J=7 Hz, 1H), 7.40 (t, J=11 Hz, 1H), 8.15 (d, J=12 Hz, 1H), 8.62 (s, 1H)

EXAMPLE 169

1-(3-amino-4,6-difluorophenyl)-7-[(3S,4R)-3-amino-4-methylpyrrolidin-1-yl]-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and (3S,4R)-3-amino-4-methylpyrrolidine were used.

Properties: yellow powder mp: 170–179° C. (decomposed)

$^1$H-NMR (d$_6$-DMSO) δ: 0.95–1.11 (m, 3H), 1.88–2.09 (m, 1H), 2.60–3.72 (m, 5H), 5.38 (s, 1H), 5.46 (s, 1H), 6.82–7.52 (m, 2H), 7.96 (d, J=14 Hz, 1H), 8.40 (brs, 1H)

EXAMPLE 170

1-(3-amino-4,6-difluorophenyl)-7-[(3R)-3-aminopyrrolidin-1-yl]-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid and (3R)-3-aminopyrrolidine were used.

Properties: brown powder mp: 169–179° C. (decomposed)

$^1$H-NMR (d$_6$-DMSO) δ: 1.52–1.80 (m, 1H), 1.84–2.07 (m, 1H), 2.71–3.82 (m, 5H), 5.40 (brs, 2H), 6.93 (m, 1H), 7.36 (t, J=10 Hz, 1H), 7.88 (d, J=14 Hz, 1H), 8.40 (s, 1H)

EXAMPLE 171

1-(3-amino-4,6-difluorophenyl)-7-(3-aminoazetidin-1-yl)-8-chloro-6-fluoro-1,4-dihydro-4-oxoquinoline-3-carboxylic acid p-toluenesulfonic acid salt To 0.5 ml of N,N-dimethylformamide was added 440 mg of 1-(3-amino-4,6-difluorophenyl)-7-(3-aminoazetidin-1-yl)-8-chloro-6-fluoro-1,4-dihydro-4-oxoquinoline-3-carboxylic acid and then 191 mg of p-toluenesulfonic acid monohydrate. The solution was stirred at room temperature. Diethyl ether was added to the reaction solution and the supernatant was removed. Ethanol was added to the residue whereupon the solid was collected by filtration and washed with diethyl ether to give 340 mg of the title compound.

Properties: yellow powder mp: 211–220° C. (decomposed)

$^1$H-NMR (d$_6$-DMSO) δ: 2.28 (s, 3H), 4.04 (brs, 1H), 4.42 (brs, 2H), 4.76 (brs, 2H), 6.99 (t, J=8 Hz, 1H), 7.11 (d, J=7 Hz, 2H), 7.37 (t, J=11 Hz, 1H), 7.48 (d, J=8 Hz, 2H), 7.94 (d, J=15 Hz, 1H), 8.33 (brs, 3H), 8.44 (s, 1H)

EXAMPLE 172

1-(3-amino-4,6-difluorophenyl)-7-(3-aminoazetidin-1-yl)-8-chloro-6-fluoro-1,4-dihydro-4-oxoquinoline-3-carboxylic acid methanesulfonic acid salt The title compound was obtained by the similar procedure as Example 171 except that methanesulfonic acid was used.

Properties: pale yellow powder mp: 180–190° C. (decomposed)

$^1$H-NMR (d$_6$-DMSO) δ: 2.35 (s, 3H), 4.04 (brs, 1H), 4.43 (brs, 2H), 4.75 (brs, 2H), 6.99 (t, J=8 Hz, 1H), 7.37 (t, J=11 Hz, 11), 7.95 (d, J=14 Hz, 11), 8.36 (brs, 3H), 8.48 (s, 1H)

EXAMPLE 173

Ethyl 8-chloro-6,7-difluoro-1-(2-chloro-4-fluoro-5-nitrophenyl)-1,4-dihydro-4-oxoquinoline-3-carboxylate The title compound was obtained by the similar procedure as Example 97 except that ethyl 8-chloro-6,7-difluoro-1-(2-chloro-4-fluorophenyl)-1,4-dihydro-4-oxoquinoline-3-carboxylate was used.

Properties: brown powder mp: 197–201° C.

$^1$H-NMR (d$_6$-DMSO) δ: 1.27 (t, J=7 Hz, 3H), 4.25 (q, J=7 Hz, 2H), 8.23–8.32 (m, 2H), 8.55 (s, 1H), 8.94 (d, J=7 Hz, 1H)

EXAMPLE 174

1-(3-amino-6-chloro-4-fluorophenyl)-8-chloro-6,7-difluoro-1,4-dihydro-4-oxoquinoline-3-carboxylic acid To 5 ml of formic acid were added 1.5 g of ethyl 8-chloro-6,7-difluoro-1-(2-chloro-4-fluoro-5-nitrophenyl)-1,4-dihydro-4-oxoquinoline-3-carboxylate and 2 g of iron. The solution was heated and stirred at 60° C. for 2 hours. The insoluble was removed by filtration through celite and washed with formic acid and chloroform. The filtrate was concentrated in vacua. Ethanol was added to the residue whereupon the solid was collected by filtration and washed with diethyl ether. To the solid were added 4 ml of conc. hydrochloric acid and 4 ml of acetic acid. The solution was heated at reflux for 1 hour and allowed to cool down. The precipitated was collected by filtration and washed with ethanol and diethyl ether to give 970 mg of the title compound.

Properties: pale yellow powder mp: 237–242° C.

$^1$H-NMR (d$_6$-DMSO) δ: 7.12 (d, J=8 Hz, 1H), 7.50 (d, J=12 Hz, 1H), 8.41 (t, J=9 Hz, 1H), 8.60 (s, 1H)

EXAMPLE 175

7-(3-aminoazetidin-1-yl)-1-(3-amino-6-chloro-4-fluorophenyl)-8-chloro-6-fluoro-1,4-dihydro-4-oxoquinoline-3-carboxylic acid The title compound was obtained by the similar procedure as Example 117 except that 8-chloro-6,7-difluoro-1-(3-amino-6-chloro-4-fluorophenyl)-1,4-dihydro-4-oxoquinoline-3-carboxylic acid was used.

Properties: colorless powder
mp: >265° C. (decomposed)
¹H-NMR (d$_6$-DMSO) δ: 3.70 (brs, 1H), 4.06 (brs, 2H), 4.67 (brs, 2H), 5.76 (s, 2H), 6.99 (d, J=8 Hz, 1H), 7.46 (d, J=11 Hz, 1H), 7.88 (d, J=14 Hz, 1H), 8.48 (s, 1H)

EXAMPLE 176

1-(3-amino-6-chloro-4-fluorophenyl)-7-[(3S)-3-aminopyrrolidin-1-yl]-8-chloro-6-fluoro-1,4-dihydro-4-oxoquinoline-3-carboxylic acid The title compound was obtained by the similar procedure as Example 117 except that 8-chloro-6,7-difluoro- 1-(3-amino-6-chloro-4-fluorophenyl)-1,4-dihydro-4-oxoquinoline-3-carboxylic acid and (3S)-3-aminopyrrolidine were used.

Properties: pale yellow powder
mp: >195° C. (decomposed)
¹H-NMR (d$_6$-DMSO) δ: 1.52–1.74 (m, 1H), 1.91–2.15 (m, 1H), 2.71–3.80 (m, 5H), 5.75 (brs, 2H), 6.99 (t, J=8 Hz, 1H), 7.46 (t, J=11 Hz, 1H), 7.92 (d, J=14 Hz, 1H), 8.35 (s, 1H)

EXAMPLE 177

Ethyl 8-chloro-6,7-difluoro-1-(4-fluoro-5-nitrophenyl)-1,4-dihydro-4-oxoquinoline-3-carboxylate The title compound was obtained by the similar procedure as Example 97 except that ethyl 8-chloro-6,7-difluoro-1-(4-fluorophenyl)-1,4-dihydro-4-oxoquinoline-3-carboxylate was used.

Properties: colorless powder
mp: 249–256° C.
¹H-NMR (d$_6$-DMSO) δ: 1.26 (t, J=7 Hz, 3H), 4.23 (q, J=7 Hz, 2H), 7.84 (t, J=10 Hz, 1H), 8.14–8.19 (m, 1H), 8.23 (t, J=9 Hz, 1H), 8.50 (s, 1H), 8.65–8.68 (m, 1H)

EXAMPLE 178

8-chloro-6,7-difluoro-1-(3-amino-4-fluorophenyl)-1,4-dihydro-4-oxoquinoline-3-carboxylic acid The title compound was obtained by the similar procedure as Example 174 except that ethyl 8-chloro-5,6,7-trifluoro-1-(4-fluoro-5-nitrophenyl)-1,4-dihydro-4-oxoquinoline-3-carboxylate was used.

Properties: colorless powder
mp: 238–243° C.
¹H-NMR (d$_6$-DMSO) δ: 6.74–6.89 (m, 1H), 6.95–7.07 (m, 1H), 7.21 (t, J=8 Hz, 1H), 8.40 (t, J=9 Hz, 1H), 8.56 (s, 1H)

EXAMPLE 179

7-(3-aminoazetidin-1-yl)-1-(3-amino-4-fluorophenyl)-8-chloro-6-fluoro-1,4-dihydro-4-oxoquinoline-3-carboxylic acid The title compound was obtained by the similar procedure as Example 117 except that 8-chloro-6,7-difluoro-1-(3-amino-4-fluorophenyl)-1,4-dihydro-4-oxoquinoline-3-carboxylic acid was used.

Properties: yellow powder
mp: 236–246° C. (decomposed)
¹H-NMR (d$_6$-DMSO) δ: 3.77 (brs, 1H), 4.12 (brs, 2H), 4.66 (brs, 2H), 5.58 (s, 2H), 6.60–6.72 (m, 1H), 6.87 (d, J=8 Hz, 1H), 7.16 (t, J=10 Hz, 1H), 7.87 (d, J=14 Hz, 1H), 8.39 (s, 1H)

EXAMPLE 180

Ethyl 8-chloro-6,7-difluoro-1-(4-fluoro-2-methyl-5-nitrophenyl)-1,4-dihydro-4-oxoquinoline-3-carboxylate The title compound was obtained by the similar procedure as Example 97 except that ethyl 8-chloro-6,7-difluoro-1-(2-methyl-4-fluorophenyl)-1,4-dihydro-4-oxoquinoline-3-carboxylate was used.

Properties: red powder
mp: 187–191° C.
¹H-NMR (CDCl$_3$) δ: 1.40 (t, J=7 Hz, 3H), 2.25 (s, 3H), 4.20 (q, J=7 Hz, 2H), 7.36 (d, J=11 Hz, 1H), 8.11 (d, J=7 Hz, 1H), 8.26 (s, 1H), 8.38 (t, J=9 Hz, 1H)

EXAMPLE 181

8-chloro-6,7-difluoro-1-(3-amino-4-fluoro-6-methylphenyl)-1,4-dihydro-4-oxoquinoline-3-carboxylic acid The title compound was obtained by the similar procedure as Example 174 except that ethyl 8-chloro-6,7-difluoro-1-(4-fluoro-2-methyl-5-nitrophenyl)-1,4-dihydro-4-oxoquinoline-3-carboxylate was used.

Properties: colorless powder
mp: 225–230° C.
¹H-NMR (d$_6$-DMSO) δ: 1.89 (s, 3H), 7.00 (d, J=8 Hz, 1H), 7.16 (d, J=12 Hz, 1H), 8.42 (t, J=9 Hz, 1H), 8.51 (s, 1H)

EXAMPLE 182

1-(3-amino-4-fluoro-6-methylphenyl)-7-(3-aminoazetidin-1-yl)-8-chloro-6-fluoro-1,4-dihydro-4-oxoquinoline-3-carboxylic acid The title compound was obtained by the similar procedure as Example 117 except that 8-chloro-6,7-difluoro-1-(3-amino-4-fluoro-6-methylphenyl)-1,4-dihydro-4-oxoquinoline-3-carboxylic acid was used.

Properties: brown powder
mp: >251° C. (decomposed)
¹H-NMR (d$_6$-DMSO) δ: 1.88 (s, 3H), 3.71 (brs, 1H), 4.06 (brs, 2H), 4.65 (brs, 2H), 5.38 (s, 2H), 6.79 (d, J=7 Hz, 1H), 7.06 (d, J=11 Hz, 1H), 7.91 (d, J=13 Hz, 1H), 8.29 (s, 1H)

EXAMPLE 183

Ethyl 1-(2-bromo-4-fluoro-5-nitrophenyl)-8-chloro-6,7-difluoro-1,4-dihydro-4-oxoquinoline-3-carboxylate The title compound was obtained by the similar procedure as Example 97 except that ethyl 1-(2-bromo-4-fluorophenyl)-8-chloro-6,7-difluoro-1,4-dihydro-4-oxoquinoline-3-carboxylate was used.

Properties: brown powder
mp: 205–214° C.
¹H-NMR (d$_6$-DMSO) δ: 1.27 (t, J=7 Hz, 3H), 4.25 (q, J=7 Hz, 2H), 8.27 (t, J=9 Hz, 1H), 8.41 (d, J=11 Hz, 1H), 8.53 (s, 1H), 8.91 (d, J=8 Hz, 1H)

EXAMPLE 184

8-chloro-6,7-difluoro-1-(3-amino-6-bromo-4-fluorophenyl)-1,4-dihydro-4-oxoquinoline-3-carboxylic acid The title compound was obtained by the similar procedure as Example 117 except that ethyl 1-(2-bromo-4-fluoro-5-nitrophenyl)-8-chloro-6,7-difluoro-1,4-dihydro-4-oxoquinoline-3-carboxylate was used.

Properties: pale yellow powder mp: 231–239° C.

$^1$H-NMR (d$_6$-DMSO) δ: 7.14 (d, J=9 Hz, 1H), 7.58 (d, J=11 Hz, 1H), 8.43 (t, J=9 Hz, 1H), 8.58 (s, 1H)

EXAMPLE 185

7-(3-aminoazetidin-1-yl)-1-(3-amino-6-bromo-4-fluorophenyl)-8-chloro-6-fluoro-1,4-dihydro-4-oxoquinoline-3-carboxylic acid The title compound was obtained by the similar procedure as Example 117 except that 8-chloro-6,7-difluoro-1-(3-amino-6-bromo-4-fluorophenyl)-1,4-dihydro-4-oxoquinoline-3-carboxylic acid was used.

Properties: pale yellow powder mp: >200° C. (decomposed)

$^1$H-NMR (d$_6$-DMSO) δ: 3.89 (brs, 1H), 4.27 (brs, 2H), 4.71 (brs, 2H), 5.81 (s, 2H), 7.03 (d, J=8 Hz, 1H), 7.55 (d, J=11 Hz, 1H), 7.93 (d, J=14 Hz, 1H), 8.33 (s, 1H)

EXAMPLE 186

Ethyl 1-(2-methoxy-4-fluoro-5-nitrophenyl)-8-chloro-6,7-difluoro-1,4-dihydro-4-oxoquinoline-3-carboxylate The title compound was obtained by the similar procedure as Example 97 except that ethyl 1-(2-methoxy-4-fluorophenyl)-8-chloro-6,7-difluoro-1,4-dihydro-4-oxoquinoline-3-carboxylate was used.

Properties: pale yellow powder mp: 220–225° C.

$^1$H-NMR (CDCl$_3$) δ: 1.40 (t, J=7 Hz, 3H), 3.92 (s, 3H), 4.40 (q, J=7 Hz, 2H), 6.94 (d, J=12 Hz, 1H), 8.21–8.30 (m, 1H), 8.26 (s, 1H), 8.34 (t, J=9 Hz, 1H)

EXAMPLE 187

8-chloro-6,7-difluoro-1-(3-amino-6-methoxy-4-fluorophenyl)-1,4-dihydro-4-oxoquinoline-3-carboxylic acid The title compound was obtained by the similar procedure as Example 174 except that ethyl 1-(2-methoxy-4-fluoro-5-nitrophenyl)-8-chloro-6,7-difluoro-1,4-dihydro-4-oxoquinoline-3-carboxylate was used.

Properties: pale yellow powder mp: 143–151° C.

$^1$H-NMR (d$_6$-DMSO) δ: 3.70 (s, 3H), 7.19–7.37 (m, 2H), 8.40 (t, J=9 Hz, 1H), 8.56 (s, 1H)

EXAMPLE 188

1-(3-amino-6-methoxy-4-fluorophenyl)-7-(3-aminoazetidin-1-yl)-8-chloro-6-fluoro-1,4-dihydro-4-oxoquinoline-3-carboxylic acid The title compound was obtained by the similar procedure as Example 117 except that 8-chloro-6,7-difluoro-1-(3-amino-6-methoxy-4-fluorophenyl)-1,4-dihydro-4-oxoquinoline-3-carboxylic acid was used.

Properties: pale yellow powder mp: >244° C. (decomposed)

$^1$H-NMR (d$_6$-DMSO) δ: 3.68 (brs, 4H), 4.05 (brs, 2H), 4.65 (brs, 2H), 5.01 (s, 2H), 6.87 (brs, 1H), 7.09 (d, J=12 Hz, 1H), 7.86 (d, J=14 Hz, 1H), 8.29 (s, 1H)

EXAMPLE 189

Ethyl 1-(3-benzyloxycarbonylamino-4,6-difluorophenyl)-8-chloro-6,7-difluoro-5-nitro-1,4-dihydro-4-oxoquinoline-3-carboxylate The title compound was obtained by the similar procedure as Example 102 except that ethyl 3-chloro-2,4,5-trifluoro-6-nitrobenzoylacetate was used.

Properties: brown powder mp: 233–241° C.

$^1$H-NMR (d$_6$-DMSO) δ: 1.38 (t, J=7 Hz, 3H), 4.38 (q, J=7 Hz, 2H), 5.21 (s, 2H), 7.01–7.15 (m, 2H), 7.40 (s, 5H), 8.32–8.40 (m, 1H), 8.36 (s, 1H)

EXAMPLE 190

5-amino-1-(3-amino-4,6-difluorophenyl)-8-chloro-6,7-difluoro-1,4-dihydro-4-oxoquinoline-3-carboxylic acid The title compound was obtained by the similar procedure as Example 174 except that ethyl 1-(3-benzyloxycarbonylamino-4,6-difluorophenyl)-8-chloro-6,7-difluoro-5-nitro-1,4-dihydro-4-oxoquinoline-3-carboxylate was used.

Properties: yellow powder mp: >270° C.

$^1$H-NMR (d$_6$-DMSO) δ: 7.02 (t, J=8 Hz, 1H), 7.39 (t, J=10 Hz, 1H), 8.46 (s, 1H)

EXAMPLE 191

5-amino-1-(3-amino-4,6-difluorophenyl)-7-(3-aminoazetidin-1-yl)-8-chloro-6-fluoro-1,4-dihydro-4-oxoquinoline-3-carboxylic acid The title compound was obtained by the similar procedure as Example 117 except that 5-amino-1-(3-amino-4,6-difluorophenyl)-8-chloro-6,7-difluoro-1,4-dihydro-4-oxoquinoline-3-carboxylic acid was used.

Properties: brown powder mp: >229° C. (decomposed)

$^1$H-NMR (d$_6$-DMSO) δ: 3.98 (brs, 1H), 4.38 (brs, 2H), 4.67 (brs, 2H), 5.39 (s, 2H), 6.90 (t, J=8 Hz, 1H), 7.34 (t, J=11 Hz, 1H), 8.29 (s, 1H)

EXAMPLE 192

Ethyl 1-(3-benzyloxycarbonylamino-4,5,6-trifluorophenyl)-8-chloro-6,7-difluoro-1,4-dihydro-4-oxoquinoline-3-carboxylate The title compound was obtained by the similar procedure as Example 102 except that ethyl 3-chloro-2,4,5-trifluorobenzoylacetate and N-benzyloxycarbonyl-4,5,6-trifluoro-m-phenylenediamine were used.

$^1$H-NMR (d$_6$-DMSO) δ: 1.42 (t, J=7 Hz, 3H), 4.40 (q, J=7 Hz, 2H), 5.21 (s, 2H), 7.05 (brs, 1H), 7.39 (s, 5H), 8.19 (brs, 1H), 8.31 (s, 1H), 8.34 (t, J=8 Hz, 1H)

EXAMPLE 193

1-(3-amino-4,5,6-trifluorophenyl)-8-chloro-6,7-difluoro-1,4-dihydro-4-oxoquinoline-3-carboxylic acid The title compound was obtained by the similar procedure as Example 103 except that ethyl 1-(3-benzyloxycarbonylamino-4,5,6-trifluorophenyl)-8-chloro-6,7-difluoro-1,4-dihydro-4-oxoquinoline-3-carboxylate was used.

Properties: colorless powder
mp: 232–238° C.
$^1$H-NMR (d$_6$-DMSO) δ: 6.88 (dd, J=4 Hz, J=9 Hz, 1H), 8.40 (t, J=9 Hz, 1H), 8.79 (s, 1H)

EXAMPLE 194

7-(3-aminoazetidin-1-yl)-1-(3-amino-4,5,6-trifluorophenyl)-8-chloro-6-fluoro-1,4-dihydro-4-oxoquinoline-3-carboxylic acid The title compound was obtained by the similar procedure as Example 117 except that 1-(3-amino-4,5,6-trifluorophenyl)-8-chloro-6,7-difluoro-1,4-dihydro-4-oxoquinoline-3-carboxylic acid was used.

Properties: pale yellow powder
mp: >224° C. (decomposed)
$^1$H-NMR (d$_6$-DMSO) δ: 3.73 (brs, 1H), 4.08 (brs, 2H), 4.68 (brs, 2H), 5.78 (s, 2H), 6.78 (t, J=6 Hz, 1H), 7.87 (d, J=14 Hz, 1H), 8.55 (s, 1H)

EXAMPLE 195

Ethyl 1-(3-tert-butyloxycarbonylamino-4,6-difluorophenyl)-8-bromo-6,7-difluoro-1,4-dihydro-4-oxoquinoline-3-carboxylate The title compound was obtained by the similar procedure as Example 102 except that ethyl 3-bromo-2,4,5-trifluorobenzoylacetate and N-(t-butoxycarbonyl)-2,4-difluoro-m-phenylenediamine of Reference Example 10 were used.

$^1$H-NMR (CDCl$_3$) δ: 1.40 (t, J=7 Hz, 3H), 1.54 (s, 9H), 4.40 (q, J=7 Hz, 2H), 6.81 (brs, 1H), 7.07 (t, J=10 Hz, 1H), 8.25–8.48 (m, 2H), 8.38 (s, 1H)

EXAMPLE 196

1-(3-amino-4,6-difluorophenyl)-8-bromo-6,7-difluoro-1,4-dihydro-4-oxoquinoline-3-carboxylic acid The title compound was obtained by the similar procedure as Example 103 except that ethyl 1-(3-tert-butyloxycarbonylamino-4,6-difluorophenyl)-8-bromo-6,7-difluoro-1,4-dihydro-4-oxoquinoline-3-carboxylate was used.

Properties: yellow powder
mp: 228–232° C.
$^1$H-NMR (d$_6$-DMSO) δ: 7.05 (t, J=8 Hz, 1H), 7.43 (t, J=11 Hz, 1H), 8.43 (t, J=9 Hz, 1H), 8.69 (s, 1H)

EXAMPLE 197

7-(3-aminoazetidin-1-yl)-1-(3-amino-4,6-difluorophenyl)-8-bromo-6-fluoro-1,4-dihydro-4-oxoquinoline-3-carboxylic acid The title compound was obtained by the similar procedure as Example 117 except that 1-(3-amino-4,6-difluorophenyl)-8-bromo-6,7-difluoro-1,4-dihydro-4-oxoquinoline-3-carboxylic acid was used.

Properties: pale yellow powder
mp: >206° C. (decomposed)
$^1$H-NMR (d$_6$-DMSO) δ: 3.76 (brs, 1H), 4.07 (brs, 2H), 4.68 (brs, 2H), 5.41 (s, 2H), 6.92 (t, J=8 Hz, 1H), 7.38 (t, J=11 Hz, 1H), 7.90 (d, J=14 Hz, 1H), 8.46 (s, 1H)

EXAMPLE 198

Ethyl 1-[3-(N-t-butoxycarbonyl-N-methylamino)-4,6-difluorophenyl]-8-chloro-6,7-difluoro-4-oxo-1,4-dihydroquinoline-3-carboxylic acid Ethyl 3-ethoxy-2-(3'-chloro-2',4',5'-trifluorobenzoyl)acrylate prepared from 1.40 g of ethyl 3-chloro-2,4,5-trifluorobenzoylacetate by a conventional process was dissolved in 10 ml of chloroform. To the chloroform solution, N-(t-butoxycarbonyl)-4,6-difluoro-m-phenylenediamine was added while the end of reaction was tracked by TLC. The reaction solution was concentrated in vacua. To the residue were added 1.4 g of anhydrous potassium carbonate and 6 ml of N,N-dimethylformamide. The mixture was stirred at 90° C. for 10 minutes. The solution was allowed to cool down, further combined with 1.4 g of anhydrous potassium carbonate and 5.0 g of methyl iodide, and stirred at 60° C. for 2 hours. To the solution, 50 ml of chloroform and 500 ml of distilled water were added for separation. The chloroform layer was washed twice with 500 ml of distilled water, dried over anhydrous magnesium sulfate and concentrated in vacua. To the residue was added 3 ml of ethanol. The solution was allowed to stand. The precipitate was collected by filtration and washed with ethanol and then diisopropyl ether to give 1.38 grams of the title compound.

Properties: pale yellow powder
mp: 192–194° C.
$^1$H-NMR (CDCl$_3$) δ: 1.43 (t, J=7 Hz, 3H), 1.44 (s, 9H), 3.22 (s, 3H), 4.41 (q, J=7 Hz, 2H), 7.10 (t, J=9 Hz, 1H), 7.38 (t, J=8 Hz, 1H), 8.34 (dd, J=8 Hz, 10 Hz, 1H), 8.58 (s, 1H)

EXAMPLE 199

1-(3-methylamino-4,6-difluorophenyl)-8-chloro-6,7-difluoro-4-oxo-1,4-dihydroquinoline-3-carboxylic acid To 4 ml of a mixture of 4N hydrochloric acid and acetic acid (1/1 vol/vol) was added 1.26 g of ethyl 1-[3-(N-t-butoxycarbonyl-N-methylamino)-4,6-difluorophenyl]-8-chloro-6,7-difluoro-4-oxo-1,4-dihydroquinoline-3-carboxylate. The solution was stirred and heated at reflux for 1.5 hours. After 5 ml of distilled water was added, the reaction solution was allowed to cool down. The precipitate was collected by filtration and washed with ethanol and then diisopropyl ether to give 890 mg of the title compound.

Properties: pale yellow powder
mp: 217–220° C.
$^1$H-NMR (d$_6$-DMSO) δ: 2.67 (d, J=5 Hz, 3H), 5.95 (brs, 1H), 7.06 (t, J=8 Hz, 1H), 7.45 (dd, J=10 Hz, 12 Hz, 1H), 8.41 (dd, J=9 Hz, 10 Hz, 1H), 8.72 (S, 1H)

EXAMPLE 200

7-(3-aminoazetidinyl)-1-(3-methylamino-4,6-difluorophenyl)-8-chloro-6-fluoro-4-oxo-1,4-dihydroquinoline-3-carboxylic acid To 650 mg of N,N-dimethylformamide were added 150 mg of 1-(3-methylamino-4,6-difluorophenyl)-8-chloro-6,7- difluoro-4-oxo-1,4-dihydroquinoline-3-carboxylic acid, 110 mg of 3-aminoazetidine dihydrochloride, and 250 mg of N-methylpyrrolidine. The solution was stirred at 90° C. for 1 hour. After 0.5 ml of ethanol was added, the reaction solution was allowed to cool down. The precipitate was collected by filtration and washed with ethanol and then diisopropyl ether to give 130 mg of the title compound.

Properties: colorless powder mp: 209–212° C.

$^1$H-NMR (d$_6$-DMSO) δ: 2.68 (d, J=5 Hz, 3H), 3.69 (m, 1H), 4.02 (m, 2H), 4.65 (m, 2H), 5.89 (brs, 1H), 6.96 (t, J=8 Hz, 1H), 7.40 (t, J=10 Hz, 1H), 7.88 (d, J=14 Hz, 1H), 8.48 (s, 1H)

EXAMPLE 201

Ethyl 1-(3-amino-4,6-difluorophenyl)-6,7-difluoro-8-methoxy-1,4-dihydro-4-oxoquinoline-3-carboxylate To 4.1 g of ethyl 2,4,5-trifluoro-3-methoxybenzoylacetate were added 8.6 ml of acetic anhydride, and 3.2 ml of triethyl ortho-formate. After the solution was heated at reflux for 2 hours, the solvent was distilled off. Toluene was added to the residue, followed by azeotropic distillation. To the residue was added 10 ml of chloroform. A solution of 1.81 g of N-benzyloxycarbonyl-2,4-difluoro-m-phenylenediamine in 10 ml of chloroform was added dropwise to the solution at 0° C. and stirred at room temperature for 3 days. The reaction solution was distilled of the solvent and passed through a silica gel column chromatograph (eluting solvent, ethyl acetate/hexane=1/8) for purification to give 2.4 g of an oily product. To a solution of 580 mg of the oily product in 4 ml of N,N-dimethylformamide was added 138 mg of potassium carbonate. The solution was stirred at 100° C. for 25 minutes. The reaction solution was poured into ice water, to which ice water and ethyl acetate were added. The organic layer was separated, washed with water, dried over magnesium sulfate, and distilled of the solvent. The residue was passed through a silica gel column chromatograph (eluting solvent, chloroform/methanol=10/1). The thus obtained solid was collected by filtration and washed with diethyl ether to give 250 mg of the title compound.

Properties: pale yellow powder mp: 159–162° C.

$^1$H-NMR (CDCl$_3$) δ: 1.39 (t, J=7 Hz, 3H), 3.57 (s, 3H), 4.37 (q, J=7 Hz, 2H), 6.84 (t, J=8 Hz, 1H), 7.00 (t, J=9 Hz, 1H), 8.08 (t, J=9 Hz, 1H), 8.26 (s, 1H)

EXAMPLE 202

1-(3-amino-4,6-difluorophenyl)-6,7-difluoro-8-methoxy-1,4-dihydro-4-oxoquinoline-3-carboxylic acid The title compound was obtained by the similar procedure as Example 103 except that ethyl 1-(3-amino-4,6-difluorophenyl)-6,7-difluoro-8-methoxy-1,4-dihydro-4-oxoquinoline-3-carboxylate was used.

Properties: colorless powder mp: >277° C. (decomposed)

$^1$H-NMR (d$_6$-DMSO) δ: 3.12 (s, 3H), 6.71 (t, J=9 Hz, 1H), 7.00 (t, J=10 Hz, 1H), 7.73 (t, J=9 Hz, 1H), 8.20 (s, 1H)

EXAMPLE 203

7-(3-aminoazetidin-1-yl)-1-(3-amino-4,6-difluorophenyl)-6-fluoro-8-methoxy-1,4-dihydro-4-oxoquinoline-3-carboxylic acid In 4 ml of diethyl ether was suspended 170 mg of 1-(3-amino-4,6-difluorophenyl)-6,7-difluoro-8-methoxy-1,4-dihydro-4-oxoquinoline-3-carboxylic acid. With ice cooling, 9 ml of boron trifluoride diethyl ether complex was added to the suspension, which was stirred at room temperature for 1.5 hours. Diethyl ether was added to the reaction solution whereupon the precipitated solid was collected by filtration and washed with ethanol and then diethyl ether to give a pale yellow powder.

While a solution of 70 mg of 3-aminoazetidine dihydrochloride and 0.17 ml of triethylamine in 1 ml of dimethylsulfoxide was stirred at 70° C., 100 mg of the above-obtained compound was added. Stirring was continued at the temperature for 2 hours. Diethyl ether was added to the reaction solution, followed by decantation. To the residue were added 5 ml of 80% methanol and 5 ml of triethylamine. The mixture was refluxed overnight. Ethanol was added to the reaction solution whereupon the solid was collected by filtration to give 34 mg of the title compound as a yellowish brown powder.

Properties: yellow powder mp: >290° C.

$^1$H-NMR (d$_6$-DMSO) δ: 3.11 (s, 3H), 3.74–3.89 (m, 2H), 3.90–4.02 (m, 1H), 4.38–4.48 (m, 2H), 5.36 (brs, 2H), 7.14 (t, J=9 Hz, 1H), 7.30 (t, J=10 Hz, 1H), 7.76 (d, J=12 Hz, 1H), 8.39 (s, 1H)

EXAMPLE 204

8-chloro-6,7-difluoro-1-(2,4,6-trifluoro-3-nitrophenyl)-1,4-dihydro-4-oxoquinoline-3-carboxylic acid The title compound was obtained by the similar procedure as Example 9 except that 8-chloro-6,7-difluoro-1-(2,4,6-trifluorophenyl)-1,4-dihydro-4-oxoquinoline-3-carboxylic acid was used.

Properties: pale yellow powder mp: 157–159° C.

$^1$H-NMR (d$_6$-DMSO) δ: 8.16 (t, J=11 Hz, 1H), 8.40 (t, J=9 Hz, 1H), 9.06 (s, 1H)

EXAMPLE 205

Ethyl 8-chloro-6,7-difluoro-1-(2,4,6-trifluoro-3-nitrophenyl)-1,4-dihydro-4-oxoquinoline-3-carboxylate To 830 mg of 8-chloro-6,7-difluoro-1-(2,4,6-trifluoro-3-nitrophenyl)-1,4-dihydro-4-oxoquinoline-3-carboxylic acid was added 2 ml of thionyl chloride. The solution was stirred at 80° C. overnight. With ice cooling, 4 ml of ethanol was slowly added dropwise to the reaction solution. The reaction solution was distilled of the solvent whereupon the precipitated solid was collected by filtration to give 310 mg of the title compound.

Properties: pale yellow powder mp: 167–169° C.

$^1$H-NMR (CDCl$_3$) δ: 1.41 (t, J=7 Hz, 3H), 4.41 (q, J=7 Hz, 2H), 7.19 (t, J=9 Hz, 1H), 8.22 (s, 1H), 8.35 (t, J=9 Hz, 1H)

EXAMPLE 206

Ethyl 8-chloro-6,7-difluoro-1-(2,4,6-trifluoro-3-formylaminophenyl)-1,4-dihydro-4-oxoquinoline-3-carboxylate The title compound was obtained by the similar procedure as Example 166 except that ethyl 8-chloro-6,7-difluoro- 1-(2,4,6-trifluoro-3-nitrophenyl)-1,4-dihydro-4-oxoquinoline-3-carboxylate was used.

Properties: pale brown powder
mp: 197–199° C.

EXAMPLE 207

1-(3-amino-2,4,6-trifluorophenyl)-8-chloro-6,7-difluoro-1,4-dihydro-4-oxoquinoline-3-carboxylic acid The title compound was obtained by the similar procedure as Example 19 except that ethyl 8-chloro-6,7-difluoro-1-(2,4,6-trifluoro-3-formylaminophenyl)-1,4-dihydro-4-oxoquinoline-3-carboxylate was used.

Properties: pale yellow powder
$^1$H-NMR (d$_6$-DMSO) δ: 5.57 (brs, 2H), 7.42 (t, J=11 Hz, 1H), 8.40 (t, J=9 Hz, 1H), 8.91 (s, 1H)

EXAMPLE 208

7-(3-aminoazetidin-1-yl)-1-(3-amino-2,4,6-trifluorophenyl)-8-chloro-6-fluoro-1,4-dihydro-4-oxoquinoline-3-carboxylic acid The title compound was obtained by the similar procedure as Example 117 except that 1-(3-amino-2,4,6-trifluorophenyl)-8-chloro-6,7-difluoro-1,4-dihydro-4-oxoquinoline-3-carboxylate was used.

Properties: pale brown powder
mp: >290° C.
$^1$H-NMR (d$_6$-DMSO) δ: 3.77–3.86 (m, 1H), 4.15–4.27 (m, 2H), 4.64–4.75 (m, 1H), 5.52 (brs, 2H), 7.38 (t, J=10 Hz, 1H), 7.91 (d, J=13 Hz, 1H), 8.66 (s, 1H)

EXAMPLE 209

Ethyl 1-(3-benzyloxycarbonylamino-4,6-difluorophenyl)-6-chloro-7,8-difluoro-1,4-dihydro-4-oxoquinoline-3-carboxylate The title compound was obtained by the similar procedure as Example 102 except that ethyl 5-chloro-2,3,4-trifluorobenzoylacetate and 3-benzyloxycarbonyl-2,4-difluoro-m-phenylenediamine were used.

Properties: pale yellow powder
mp: 204–205° C.
$^1$H-NMR (CDCl$_3$) δ: 1.39 (t, J=7 Hz, 3H), 4.38 (q, J=7 Hz, 2H), 7.02 (brs, 1H), 7.11 (t, J=10 Hz, 1H), 7.39 (s, 5H), 8.28 (s, 1H), 8.35–8.50 (m, 2H)

EXAMPLE 210

1-(3-amino-4,6-difluorophenyl)-6-chloro-7,8-difluoro-1,4-dihydro-4-oxoquinoline-3-carboxylic acid The title compound was obtained by the similar procedure as Example 103 except that ethyl 1-(3-benzyloxycarbonylamino-4,6-difluorophenyl)-6-chloro-7,8-difluoro-1,4-dihydro-4-oxoquinoline-3-carboxylate was used.

Properties: colorless powder
mp: 276–278° C.
$^1$H-NMR (d$_6$-DMSO) δ: 7.15 (t, J=9 Hz, 1H), 7.45 (t, J=11 Hz, 1H), 8.38 (d, J=8 Hz, 1H), 8.73 (s, 1H)

EXAMPLE 211

1-(3-amino-4,6-difluorophenyl)-7-[(3S)-3-aminopyrrolidin-1-yl]-6-chloro-8-fluoro-1,4-dihydro-4-oxoquinoline-3-carboxylic acid The title compound was obtained by the similar procedure as Example 60 except that 1-(3-amino-4,6-difluorophenyl)-6-chloro-7,8-difluoro-1,4-dihydro-4-oxoquinoline-3-carboxylic acid was used.

Properties: pale yellow powder
mp: >240° C. (decomposed)
$^1$H-NMR (d$_6$-DMSO) δ: 1.51–1.68 (m, 1H), 1.88–2.04 (m, 1H), 5.44 (brs, 2H), 7.09 (t, J=8 Hz, 1H), 7.39 (t, J=11 Hz, 1H), 8.05 (s, 1H), 8.48 (s, 1H)

EXAMPLE 212

7-(3-aminoazetidin-1-yl)-1-(3-amino-4,6-difluorophenyl)-6-chloro-8-fluoro-1,4-dihydro-4-oxoquinoline-3-carboxylic acid The title compound was obtained by the similar procedure as Example 60 except that 1-(3-amino-4,6-difluorophenyl)-6-chloro-7,8-difluoro-1,4-dihydro-4-oxoquinoline-3-carboxylic acid and 3-aminoazetidine dihydrochloride were used.

Properties: pale yellow powder
mp: 190–193° C.
$^1$H-NMR (d$_6$-DMSO) δ: 3.65–3.77 (m, 1H), 3.97–4.10 (m, 2H), 4.52–4.68 (m, 2H), 5.44 (brs, 2H), 7.07 (t, J=8 Hz, 1H), 7.38 (t, J=11 Hz, 1H), 7.96 (s, 1H), 8.45 (s, 1H)

EXAMPLE 213

Ethyl 8-chloro-1-(4-chloro-2-fluoro-5-nitrophenyl)-6,7-difluoro-1,4-dihydro-4-oxoquinoline-3-carboxylate The title compound was obtained by the similar procedure as Example 97 except that ethyl 8-chloro-1-(4-chloro-2-fluorophenyl)-6,7-difluoro-1,4-dihydro-4-oxoquinoline-3-carboxylate was used.

Properties: colorless powder
mp: 206–208° C.
$^1$H-NMR (CDCl$_3$) δ: 1.40 (t, J=7 Hz, 3H), 4.40 (q, J=7 Hz, 2H), 7.57 (d, J=9 Hz, 1H), 8.16 (d, J=7 Hz, 1H), 8.30 (s, 1H), 8.34 (t, J=10 Hz, 1H)

EXAMPLE 214

Ethyl 8-chloro-1-(4-chloro-6-fluoro-3-formylaminophenyl)-6,7-difluoro-1,4-dihydro-4-oxoquinoline-3-carboxylate The title compound was obtained by the similar procedure as Example 166 except that ethyl 8-chloro-1-(4-chloro-2-fluoro-5-nitrophenyl)-6,7-difluoro-1,4-dihydro-4-oxoquinoline-3-carboxylate was used.

Properties: pale brown powder
mp: 241–244° C.

EXAMPLE 215

1-(3-amino-4-chloro-6-fluorophenyl)-8-chloro-6,7-difluoro-1,4-dihydro-4-oxoquinoline-3-carboxylic acid The title compound was obtained by the similar procedure as Example 19 except that ethyl 8-chloro-1-(4-chloro-6-fluoro-3-formylaminophenyl)-6,7-difluoro-1,4-dihydro-4-oxoquinoline-3-carboxylate was used.

Properties: pale yellow powder
mp: 255–258° C.
$^1$H-NMR (d$_6$-DMSO) δ: 7.08 (d, J=7 Hz, 1H), 7.55 (d, J=10 Hz, 1H), 8.40 (t, J=9 Hz, 1H), 8.70 (s, 1H)

EXAMPLE 216

7-(3-aminoazetidin-1-yl)-1-(3-amino-4-chloro-6-fluorophenyl)-8-chloro-6-fluoro-1,4-dihydro-4-oxoquinoline-3-carboxylic acid The title compound was obtained by the similar procedure as Example 60 except that 1-(3-amino-4-chloro-6-fluorophenyl)-8-chloro-6,7-difluoro-1,4-dihydro-4-oxoquinoline-3-carboxylic acid and 3-aminoazetidine dihydrochloride were used.

Properties: pale yellow powder mp: >290° C.

$^1$H-NMR (d$_6$-DMSO) δ: 3.66–3.79 (m, 1H), 4.00–4.15 (m, 2H), 4.60–4.74 (m, 2H), 5.61 (brs, 2H), 7.00 (d, J=10 Hz, 1H), 7.50 (d, J=10 Hz, 1H), 7.87 (d, J=14 Hz, 1H).

EXAMPLE 217

Ethyl 1-(3-t-butoxycarbonylamino-4-fluoro-2-methoxyphenyl)-6,7-difluoro-1,4-dihydro-4-oxoquinoline-3-carboxylate The title compound was obtained by the similar procedure as Example 102 except that ethyl 3-chloro-2,4,5-trifluorobenzoylacetate and 3-t-butoxycarbonylamino-4-fluoro-2-methoxyaniline were used.

Properties: pale yellow powder mp: 184–189° C.

$^1$H-NMR (CDCl$_3$) δ: 1.39 (t, J=7 Hz, 3H), 3.64 (s, 3H), 4.39 (q, J=7 Hz, 2H), 6.05 (brs, 1H), 7.06 (t, J=8 Hz, 1H), 7.21–7.29 (m, 1H), 8.31–8.40 (m, 2H)

EXAMPLE 218

1-(3-amino-4-fluoro-2-methoxyphenyl)-6,7-difluoro-1,4-dihydro-4-oxoquinoline-3-carboxylic acid The title compound was obtained by the similar procedure as Example 103 except that ethyl 1-(3-t-butoxycarbonylamino-4-fluoro-2-methoxyphenyl)-6,7-difluoro-1,4-dihydro-4-oxoquinoline-3-carboxylate was used.

Properties: pale yellow powder mp: 203–215° C. (decomposed)

$^1$H-NMR (d$_6$-DMSO) δ: 3.43 (s, 3H), 6.78–6.90 (m, 1H), 7.08 (t, J=8 Hz, 1H), 8.42 (t, J=7 Hz, 1H), 8.61 (s, 1H)

EXAMPLE 219

7-(3-aminoazetidin-1-yl)-1-(3-amino-4-fluoro-2-methoxyphenyl)-6-fluoro-1,4-dihydro-4-oxoquinoline-3-carboxylic acid The title compound was obtained by the similar procedure as Example 117 except that 1-(3-amino-4-fluoro-2-methoxyphenyl)-6,7-difluoro-1,4-dihydro-4-oxoquinoline-3-carboxylic acid, 3-aminoazetidine dihydrochloride, and N-methylpyrrolidine were used.

Properties: colorless powder mp: >179° C. (decomposed)

$^1$H-NMR (d$_6$-DMSO) δ: 3.42 (s, 3H), 3.96–4.13 (m, 2H), 4.55–4.72 (m, 2H), 5.40 (brs, 2H), 6.71–6.83 (m, 1H), 7.03 (t, J=7 Hz, 1H), 7.88 (d, J=14 Hz, 1H), 8.39 (s, 1H)

EXAMPLE 220

Ethyl 6,7,8-trichloro-1-(3-benzyloxycarbonylamino-4,6-difluorophenyl)-1,4-dihydro-4-oxoquinoline-3-carboxylate The title compound was obtained by the similar procedure as Example 102 except that ethyl 2,3,4,5-tetrachlorobenzoylacetate and 3-benzyloxycarbonyl-2,4-difluoro-m-phenylenediamine were used.

Properties: pale yellow powder mp: 128–129° C.

$^1$H-NMR (CDCl$_3$) δ: 1.40 (t, J=7 Hz, 3H), 4.40 (q, J=7 Hz, 2H), 7.03–7.14 (m, 2H), 7.40 (s, 5H), 8.27 (s, 1H), 8.60 (s, 1H)

EXAMPLE 221

1-(3-amino-4,6-difluorophenyl)-6,7,8-trichloro-1,4-dihydro-4-oxoquinoline-3-carboxylic acid The title compound was obtained by the similar procedure as Example 103 except that ethyl 6,7,8-trichloro-1-(3-benzyloxycarbonylamino-4,6-difluorophenyl)-1,4-dihydro-4-oxoquinoline-3-carboxylate was used.

Properties: colorless powder mp: 251–252° C.

$^1$H-NMR (d$_6$-DMSO) δ: 7.01 (t, J=8 Hz, 1H), 7.41 (t, J=10 Hz, 1H), 8.52 (s, 1H), 8.66 (s, 1H)

EXAMPLE 222

Ethyl 1-(3-amino-4,6-difluorophenyl)-6,7-difluoro-8-methyl-1,4-dihydro-4-oxoquinoline-3-carboxylate The title compound was obtained by the similar procedure as Example 201 except that ethyl 2,4,5-trifluoro-3-methylbenzoylacetate was used.

Properties: pale yellow powder mp: 221–223° C.

$^1$H-NMR (CDCl$_3$) δ: 1.38 (t, J=7 Hz, 3H), 1.85 (s, 3H), 3.98 (brs, 2H), 4.37 (q, J=7 Hz, 2H), 6.81 (t, J=8 Hz, 1H), 7.02 (t, J=10 Hz, 1H), 8.19 (t, J=10 Hz, 1H), 8.32 (s, 1H)

EXAMPLE 223

1-(3-amino-4,6-difluorophenyl)-6,7-difluoro-8-methyl-1,4-dihydro-4-oxoquinoline-3-carboxylic acid The title compound was obtained by the similar procedure as Example 103 except that ethyl 1-(3-amino-4,6-difluorophenyl)-6,7-difluoro-8-methyl-1,4-dihydro-4-oxoquinoline-3-carboxylate was used.

Properties: pale yellow powder mp: 264–267° C.

$^1$H-NMR (d$_6$-DMSO) δ: 1.86 (d, J=3 Hz, 1H), 7.12 (t, J=8 Hz, 1H), 7.47 (t, J=11 Hz, 1H), 8.25 (t, J=9 Hz, 1H), 8.69 (s, 1H)

EXAMPLE 224

1-(3-amino-4,6-difluorophenyl)-7-(3-aminomethyl-3-hydroxyazetidin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid, 3-aminomethyl-3-hydroxyazetidine dihydrochloride, and triethylamine were used.

Properties: pale yellow powder mp: >209° C. (decomposed)

$^1$H-NMR (d$_6$-DMSO) δ: 2.83 (brs, 2H), 4.21 (brs, 2H), 4.52 (brs, 2H), 5.42 (brs, 2H), 6.90–7.10 (m, 1H), 7.36 (t, 1H), 7.85 (d, J=14.5 Hz, 1H), 8.39 (s, 1H)

EXAMPLE 225

1-(3-amino-4,6-difluorophenyl)-7-(3-aminomethylazetidin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid, 3-aminomethylazetidine dihydrochloride, and triethylamine were used.

Properties: pale yellow powder
mp: >217° C. (decomposed)
$^1$H-NMR (d$_6$-DMSO+d-TFA) δ: 2.89 (brs, 1H), 3.11 (brs, 2H), 4.29 (brs, 2H), 4.58 (brs, 2H), 6.90–7.05 (m, 1H), 7.36 (t, 1H), 7.90 (d, J=13 Hz, 1H), 8.46 (s, 1H)

EXAMPLE 226

1-(3-amino-4,6-difluorophenyl)-8-chloro-7-(3-dimethylaminoazetidin-1-yl)-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid, 3-dimethylaminoazetidine dihydrochloride, and triethylamine were used.

Properties: yellow powder
mp: >256° C. (decomposed)
$^1$H-NMR (d$_6$-DMSO) δ: 2.07 (s, 6H), 3.03 (brs, 1H), 4.23 (brs, 2H), 4.54 (brs, 2H), 5.41 (brs, 2H), 6.98 (t, J=8 Hz, 1H), 7.37 (t, J=11 Hz, 1H), 7.87.(d, J=13 Hz, 1H), 8.45 (s, 1H)

EXAMPLE 227

1-(3-amino-4,6-difluorophenyl)-7-(3-aminomethylpyrrolidin-1-yl)-8-chloro-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid, 3-aminomethylpyrrolidine dihydrochloride, and triethylamine were used.

Properties: yellow powder
mp: 183.0–185.5° C.
$^1$H-NMR (d$_6$-DMSO) δ: 1.50–1.80 (br, 1H), 1.85–2.10 (br, 1H), 2.35–2.60 (m, 1H), 2.80 (brs, 2H), 3.00–3.65 (m, 4H), 5.45 (brs, 2H), 6.90–7.05 (m, 1H), 7.35 (t, 1H), 7.96 (d, J=12 Hz, 1H), 8.55 (s, 1H)

EXAMPLE 228

1-(3-amino-4,6-difluorophenyl)-8-chloro-7-(3-hydroxycarbonylazetidin-1-yl)-6-fluoro-1,4-dihydro-4-oxoquinoline-3-carboxylic acid The title compound was obtained by the similar procedure as Example 117 except that 1-(3-amino-4,6-difluorophenyl)-8-chloro-6,7-difluoro-1,4-dihydro-4-oxoquinoline-3-carboxylic acid, azetidine-3-carboxylic acid hydrochloride, and triethylamine were used.

Properties: pale yellow powder
mp: 227.0–231.0° C.
$^1$H-NMR (d$_6$-DMSO) δ: 3.25–3.60 (m, 1H), 4.50 (brs, 2H), 4.66 (brs, 2H), 5.42 (brs, 2H), 6.96 (t, J=8 Hz, 1H), 7.37 (t, J 10 Hz, 1H), 7.89 (d, J=13.7 Hz, 1H), 8.46 (s, 1H)

EXAMPLE 229

7-(3-acetylaminoazetidin-1-yl)-1-(3-amino-4,6-difluorophenyl)-6-fluoro-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, 3-acetylaminoazetidine hydrochloride, and triethylamine were used.

Properties: pale brown powder
mp: 289.0–295.0° C.
$^1$H-NMR (d$_6$-DMSO) δ: 1.81 (s, 3H), 3.60–4.90 (m, 5H), 5.35 (brs, 2H), 6.94 (t, 1H), 7.35 (t, J=10 Hz, 1H), 8.06 (d, J=10 Hz, 1H), 8.54 (brs, 1H), 8.69 (s, 1H)

EXAMPLE 230

1-(3-amino-4,6-difluorophenyl)-7-((1R,4R)-2,5-diazabicyclo-[2.2.1]heptan-2-yl)-6-fluoro-1,4-dihydro-4-oxo-1,8-naphthyridine-3-carboxylic acid The title compound was obtained by the similar procedure as Example 117 except that 1-(3-amino-4,6-difluorophenyl)-7-chloro-6-fluoro-1,4-dihydro-4-oxo-1,8-naphthyridine-3-carboxylic acid, (1R,4R)-2,5-diazabicyclo-[2.2.1]heptane dihydrochloride, and triethylamine were used.

Properties: pale yellow powder
mp: >284° C. (decomposed)
$^1$H-NMR (d$_6$-DMSO+d-TFA) δ: 1.90 (d, J=11 Hz, 1H), 2.11 (d, J=11 Hz, 1H), 3.15–3.90 (m, 5H), 4.45 (s, 1H), 5.20–6.10 (br, 2H), 6.98 (t, 1H), 7.36 (t, J=10 Hz, 1H), 8.18 (d, J=12 Hz, 1H), 8.76 (s, 1H), 9.15–9.30 (br, 2H)

EXAMPLE 231

1-(3-amino-4,6-difluorophenyl)-8-chloro-7-(3,7-diazabicyclo-[3.3.0]octan-3-yl)-6-fluoro-1,4-dihydro-4-oxoquinoline-3-carboxylic acid hydrochloride In 3 ml of acetonitrile were dissolved 100 mg of 1-(4-amino-4,6-difluorophenyl)-8-chloro-6,7-difluoro-1,4-dihydro-4-oxoquinoline-3-carboxylic acid, 104 mg of 3-t-butoxycarbonyl-3,7-diazabicyclo[3.3.0]octane, and 150 mg of triethylamine. The solution was stirred at 80° C. for 3 hours. The solvent was distilled off in vacua. The residue was extracted with 30 ml of chloroform. The organic layer was washed with 20 ml of 3% citric acid aqueous solution, dried, and then distilled. The residue was dissolved in 20 ml of dichloromethane, combined with 5 ml of 4N hydrochloric acid/dioxane, and stirred at room temperature for 2 hours. The solvent was distilled off in vacua. The residue was solidified with isopropyl ether and collected by filtration to give 120 mg of the title compound as a pale yellow powder.

Properties: pale yellow powder
mp: 199.5–204.0° C.
$^1$H-NMR (d$_6$-DMSO) δ: 2.85–3.10 (m, 4H), 3.30–3.70 (m, 6H), 7.02 (t, J=8 Hz, 1H), 7.41 (t, J=10 Hz, 1H), 8.08 (d, J=12.5 Hz, 1H), 8.59 (s, 1H), 9.13 (brs, 1H), 9.26 (brs, 1H)

EXAMPLE 232

1-(3-amino-4,6-difluorophenyl)-7-(3,7-diazabicyclo-[3.3.0]octan-3-yl)-6-fluoro-1,4-dihydro-4-oxo-1,8-naphthyridine-3-carboxylic acid hydrochloride The title compound was obtained by the similar procedure as Example 231 except that 1-(3-amino-4,6- difluorophenyl)-7-chloro-6-fluoro-1,4-dihydro-4-oxo-1,8-naphthyridine-3-carboxylic acid and 3-t-butoxycarbonyl-3,7-diazabicyclo[3.3.0]octane were used.

Properties: pale yellow powder
mp: 203.0–208.0° C.
$^1$H-NMR (d$_6$-DMSO) δ: 3.06 (brs, 4H), 3.36 (brs, 2H), 3.40–3.90 (m, 4H), 7.12 (t, 1H), 7.42 (t, J=11 Hz, 1H), 8.09 (d, J=13 Hz, 1H), 8.72 (s, 1H), 9.46 (brs, 2H)

EXAMPLE 233

1-(3-amino-4,6-difluorophenyl)-7-(3,7-diazabicyclo-[3.3.0]octan-3-yl)-6-fluoro-1,4-dihydro-4-oxoquinoline-3-carboxylic acid hydrochloride The title compound was obtained by the similar procedure as Example 231 except that 1-(3-amino-4,6-difluorophenyl)-6,7-difluoro-1,4-dihydro-4-oxoquinoline-3-carboxylic acid and 3-t-butoxycarbonyl-3,7-diazabicyclo-[3.3.0]octane were used.

Properties: yellow powder
mp: 221–224.5° C.
$^1$H-NMR (d$_6$-DMSO) δ: 2.95–3.20 (m, 4H), 3.25–3.65 (m, 6H), 6.06 (d, 1H), 7.12 (t, 1H), 7.53 (t, 1H), 7.91 (d, J=14 Hz, 1H), 8.67 (s, 1H), 9.30–9.76 (br, 2H)

EXAMPLE 234

1-(3-amino-4,6-difluorophenyl)-7-(3-aminoethylazetidin-1-yl)-8-chloro-6-fluoro-1,4-dihydro-4-oxoquinoline-3-carboxylic acid trifluoroacetic acid salt Reaction was carried out as in Example 231 except that 1-(3-amino-4,6-difluorophenyl)-8-chloro-6,7-difluoro-1,4-dihydro-4-oxoquinoline-3-carboxylic acid, 3-t-butoxycarbonylaminoethylazetidine, and triethylamine were used. For deprotection, trifluoroacetic acid was used rather than 4N hydrochloric acid/dioxane to give the title compound.

Properties: yellow powder
mp: 140.0–141.5° C.
$^1$H-NMR (d$_6$-DMSO) δ: 1.80–1.95 (m, 2H), 2.60–2.85 (m, 3H), 4.14 (brs, 2H), 4.57 (brs, 2H), 6.95 (dd, J=7 Hz, J=9 Hz, 1H), 7.36 (t, J=11 Hz, 1H), 7.70 (brs, 3H), 8.87 (d, J=13.5 Hz, 1H), 8.45 (s, 1H)

EXAMPLE 235

5-benzyloxy-1-(3-benzyloxycarbonylamino-4,6-difluorophenyl)-6,7,8-trifluoro-1,4-dihydro-4-oxoquinoline-3-carboxylic acid ethyl ester A mixture of 1.11 grams of ethyl 6-benzyloxy-2,3,4,5-tetrafluorobenzoylacetate, 0.75 ml of ethyl ortho-formate, and 0.85 ml of acetic anhydride was stirred at 130° C. for 1 hour. Distillation in vacua left a residue, to which 10 ml of dichloromethane was added. To the solution was added 0.8 g of N-benzyloxycarbonyl-2,4-difluoro-m-phenylenediamine. The solution was stirred at room temperature for 2 hours. The solvent was distilled off in vacua. The residue was dissolved in 3 ml of N,N-dimethylformamide. The solution was combined with 0.41 g of potassium carbonate and stirred at 100° C. for 10 minutes. To the reaction solution was added 50 ml of 5% citric acid. It was extracted with 50 ml of chloroform. The organic layer was washed with a saturated sodium chloride aqueous solution, and dried over magnesium sulfate. Distillation in vacua left a residue which was passed through a column chromatograph (silica gel, chloroform/ethyl acetate=20/1). There was obtained 1.4 g of the title compound as a red oily mass.

Properties: red oily mass
$^1$H-NMR (CDCl$_3$) δ: 1.37 (t, J=7 Hz, 3H), 4.38 (t, J=7 Hz, 2H), 5.21 (s, 1H), 5.26 (s, 1H), 7.01 (s, 1H), 7.08 (t, J=10 Hz, 1H), 7.25–7.55 (brs, 8H), 7.55–7.65 (m, 2H), 8.14 (s, 1H), 8.40 (brs, 1H)

EXAMPLE 236

1-(3-amino-4,6-difluorophenyl)-5-hydroxy-6,7,8-trifluoro-1,4-dihydro-4-oxoquinoline-3-carboxylic acid To 8 ml of acetic acid and 10 ml of 6N hydrochloric acid was added 1.3 g of the compound synthesized in Example 235. The solution was stirred at 100° C. for 4 hours. The solvent was distilled off in vacua. Water was added to the residue. The solid was collected by filtration and washed with water, ethanol, and isopropyl ether to give 0.55 g of the title compound as a yellow solid.

Properties: yellow powder
mp: >278.0° C. (decomposed)
$^1$H-NMR (d$_6$-DMSO) δ: 5.47 (brs, 2H), 7.08 (dd, J=8 Hz, J=9 Hz, 1H), 7.41 (dd, J=10 Hz, J=11 Hz, 1H), 8.59 (s, 1H)

EXAMPLE 237

1-(3-amino-4,6-difluorophenyl)-7-(3-aminoazetidin-1-yl)-6,8-difluoro-5-hydroxy-1,4-dihydro-4-oxoquinoline-3-carboxylic acid The title compound was obtained by the similar procedure as Example 117 except that 1-(3-amino-4,6-difluorophenyl)-5-hydroxy-6,7,8-trifluoro-1,4-dihydro-4-oxoquinoline-3-carboxylic acid, 3-aminoazetidine dihydrochloride, and triethylamine were used.

Properties: yellow powder
mp: >261° C. (decomposed)

Test 1
Antibacterial action

A minimum growth-inhibition concentration (MIC: μg/ml) was measured according to the standard method of the Japanese Chemotherapy Society (CHEMOTHERAPY, 29 (1), 76, 1981). The results are shown in Table 1.

TABLE 1

| Compound | S. aureus 209P | P. aeruginosa IFO3445 |
| --- | --- | --- |
| Compound of Example 48 | 0.025 | 0.1 |
| Compound of Example 56 | 0.025 | 0.1 |
| Compound of Example 60 | 0.013 | 0.1 |
| Compound of Example 117 | 0.05 | 0.1 |
| Compound of Example 150 | 0.025 | 0.2 |
| Compound of Example 152 | <0.013 | 0.05 |
| Compound of Example 156 | <0.013 | 0.1 |
| Compound of Example 157 | <0.013 | 0.1 |
| Compound of Example 160 | 0.025 | 0.2 |
| Compound of Example 162 | 0.013 | 0.2 |
| tosufloxacin | 0.05 | 0.39 |

Test 2
Cytotoxicity test

Each well of a 96 well tissue culture plate was incubated with Hela S3 cells and IMR 32 cells (5×10$^3$ cells/well and $4\times10^4$ cells/well, respectively) suspended in an Eagle's MEM medium having 10% bovine fetal serum and 0.1 mM non-essential amino acid added thereto. Agents were added in different concentrations. The cells were cultured at 37° C. for 6 hours in the presence of 5% $CO_2$, and at the end of culturing, the medium was fixed with 5% glutaraldehyde and stained with 0.05% methylene blue. The staining dye was extracted with 0.3N HCl. An absorbency was measured at a wavelength of 650 nm to calculate an $IC_{50}$ value. The results are shown in Table 2.

TABLE 2

| Compound | HeLa cells | IMR 32 cells |
| --- | --- | --- |
| Compound of Example 48 | 39.0 | 38.4 |
| Compound of Example 117 | 36.8 | >50.0 |
| Compound of Example 160 | >25.0 | >25.0 |
| tosufloxacin | 7.7 | 9.6 |

Test 3

Phototoxicity test

After a compound to be tested (40 mg/kg/10 ml) was intravenously administered to a female ICR mouse (5–6 weeks old), ultraviolet radiation (320 to 400 nm, 1.8 $mW/cm^2/sec.$) was irradiated for 4 hours. The ears were observed for abnormality after 24 and 48 hours, provided that the end of irradiation is 0 hour. Ear abnormality was rated point 0 for no abnormality, point 1 for light erythema, point 2 for medium erythema, and point 3 for heavy erythema or edema. The results are shown in Table 3.

TABLE 3

| | Rating frequency | | |
| --- | --- | --- | --- |
| Compound | 0 hour | 24 hours | 48 hours |
| Compound of Example 48 | 0, 0/3 | 0, 0/3 | 0, 0/3 |
| Compound of Example 117 | 0, 0/3 | 0, 0/3 | 0, 0/3 |
| Compound of Example 150 | 0, 0/3 | 0, 0/3 | 0, 0/3 |
| Compound of Example 152 | 0, 0/3 | 0, 0/3 | 0, 0/3 |
| Compound of Example 160 | 0, 0/3 | 0, 0/3 | 0, 0/3 |
| tosufloxacin | 1.8, 4/5 | 0.8, 4/5 | 0.2, 1/5 |

Test 4

Chromosomal aberration test

CHL cells (0.2 to $2\times10^5$ cells/well) suspended in an Eagle's MEM medium having 10% bovine fetal serum added thereto were incubated in a 60-mm dish. After the cells were cultured at 37° C. for 4 to 72 hours in the presence of 5% $CO_2$, the medium was replaced by a medium containing an agent in a different concentration and culturing was continued under the same conditions. In the case of a metabolic activation method (S9 added medium), after 6 hours of culturing, the medium was replaced by a medium free of an agent and S9 and culturing was continued for a further 18 hours. In the case of a direct method, the cells were cultured in two ways for 24 hours and 48 hours. At the end of culturing, a chromosome sample was prepared according to the method prescribed by the Japan Surrounding Mutagen society. Using a microscope, 100 metaphase images were observed to calculate a rate of structural aberration.

As a result, the compounds of Examples 48 and 117 were negative in a concentration of from 0 to 200 µg/ml.

We claim:

1. A pyridonecarboxylic acid derivative of the following general formula (1):

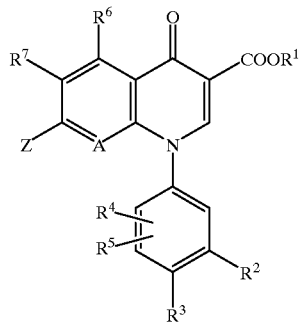

(1)

wherein $R^1$ is a hydrogen atom or carboxy protecting group, $R^2$ is a nitro or substituted or unsubstituted amino group, $R^3$ is a halogen atom, each of $R^4$ and $R^5$, which may be the same or different, is a hydrogen atom, halogen atom, lower alkyl group or lower alkoxy group with the proviso that both of $R^4$ and $R^5$ are not simultaneously hydrogen atoms, $R^6$ is a hydrogen atom, halogen atom, hydroxy group, lower alkyl group or amino group, $R^7$ is a hydrogen atom or halogen atom, A is a nitrogen atom or —CX= wherein X is a hydrogen atom, halogen atom, lower alkyl group or lower alkoxy group, and Z is a halogen atom or a saturated cyclic amino group which may have a substituent, or a salt thereof.

2. An antibacterial agent comprising a pyridonecarboxylic acid derivative or a salt thereof as set forth in claim 1 as an active ingredient and a pharmaceutically acceptable carrier therefor.

3. A method of treating a person infected with bacteria by administering an effective amount of the compound of claim 1 to a person in need thereof.

4. A method of treating an animal infected with bacteria by administering an effective amount of the compound of claim 1 to an animal in need thereof.

5. A method of treating a person infected with a virus by administering an effective amount of the compound of claim 1 to a person in need thereof.

6. A method of treating an animal infected with a virus by administering an effective amount of the compound of claim 1.

7. A pyridonecarboxylic acid derivative of the following general formula (1):

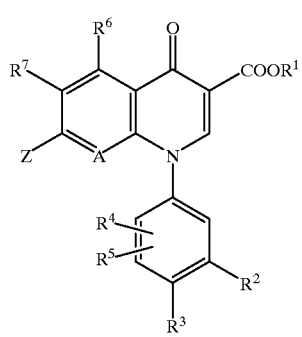

(1)

wherein $R^1$ is a hydrogen atom or carboxy protecting group, $R^2$ is a nitro or substituted or unsubstituted amino group, $R^3$ is a halogen atom, each of $R^4$ and $R^5$, which may be the same or different, is a hydrogen atom, halogen atom, lower alkyl group or lower alkoxy group, $R^6$ is a hydrogen atom, halogen atom, hydroxy group, lower alkyl group or amino group, $R^7$ is a hydrogen atom or halogen atom, A is a nitrogen atom or —CX= wherein X is a halogen atom, lower alkyl group or lower alkoxy group, and Z is a halogen atom or a saturated cyclic amino group which may have a substitutent, or a salt thereof.

8. An antibacterial agent comprising a pyridonecarboxylic acid derivative or a salt thereof as set forth in claim 7 as an active ingredient and a pharmaceutically acceptable carrier therefor.

9. A method of treating a person infected with bacteria by administering an effective amount of the compound of claim 7 to a person in need thereof.

10. A method of treating an animal infected with bacteria by administering an effective amount of the compound of claim 7 to an animal in need thereof.

11. A method of treating a person infected with a virus by administering an effective amount of the compound of claim 7 to a person in need thereof.

12. A method of treating an animal infected with a virus by administering an effective amount of the compound of claim 7.

* * * * *